(12) United States Patent
Ichihashi et al.

(10) Patent No.: US 11,447,484 B2
(45) Date of Patent: Sep. 20, 2022

(54) CYCLIC COMPOUND HAVING DOPAMINE D3 RECEPTOR ANTAGONISTIC EFFECT

(71) Applicant: Shionogi & Co., Ltd., Osaka (JP)

(72) Inventors: Yusuke Ichihashi, Osaka (JP); Masanao Inagaki, Osaka (JP); Koji Masuda, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 7 days.

(21) Appl. No.: 16/964,347

(22) PCT Filed: Jan. 25, 2019

(86) PCT No.: PCT/JP2019/002397
§ 371 (c)(1),
(2) Date: Jul. 23, 2020

(87) PCT Pub. No.: WO2019/146740
PCT Pub. Date: Aug. 1, 2019

(65) Prior Publication Data
US 2021/0047315 A1 Feb. 18, 2021

(30) Foreign Application Priority Data

Jan. 26, 2018 (JP) .............................. JP2018-011087

(51) Int. Cl.
| C07D 417/14 | (2006.01) |
| C07D 401/14 | (2006.01) |
| C07D 413/14 | (2006.01) |
| C07D 471/04 | (2006.01) |

(52) U.S. Cl.
CPC ......... *C07D 417/14* (2013.01); *C07D 401/14* (2013.01); *C07D 413/14* (2013.01); *C07D 471/04* (2013.01)

(58) Field of Classification Search
None
See application file for complete search history.

(56) References Cited

U.S. PATENT DOCUMENTS

| 4,988,699 | A | 1/1991 | Caprathe et al. |
| 8,921,397 | B2 * | 12/2014 | Rodriguez Sarmiento .................. C07D 405/04 514/320 |
| 10,899,758 | B2 * | 1/2021 | Cacatian ............. C07D 487/04 |
| 2007/0299091 | A1 | 12/2007 | Gmeiner et al. |
| 2009/0143398 | A1 | 6/2009 | Szalai et al. |
| 2011/0021490 | A1 | 1/2011 | De Nanteuil et al. |
| 2011/0319423 | A1 | 12/2011 | Li et al. |
| 2016/0096811 | A1 | 4/2016 | Li et al. |
| 2018/0297975 | A1 | 10/2018 | Huang et al. |

FOREIGN PATENT DOCUMENTS

| CN | 1948315 | 4/2007 |
| CN | 107793408 | 3/2018 |
| EP | 0 431 580 | 6/1991 |
| EP | 0 465 254 | 1/1992 |
| EP | 1 870 405 | 12/2007 |
| EP | 2 995 617 | 3/2016 |
| EP | 3 495 363 | 6/2019 |
| WO | 96/02249 | 2/1996 |
| WO | 02/066446 | 8/2002 |
| WO | 02/066468 | 8/2002 |
| WO | 02/066469 | 8/2002 |
| WO | 02/079151 | 10/2002 |
| WO | 03/029233 | 4/2003 |
| WO | 2004/091490 | 10/2004 |
| WO | 2005/012266 | 2/2005 |
| WO | 2005/080382 | 9/2005 |
| WO | 2006/050239 | 5/2006 |
| WO | 2006/050976 | 5/2006 |
| WO | 2006/082456 | 8/2006 |

(Continued)

OTHER PUBLICATIONS

Gamo, F.-J. et al., Nature 2010 vol. 465, pp. 305-310.*
International Search Report dated Mar. 19, 2019 in International (PCT) Application No. PCT/JP2019/002397 with English-language translation.
Joyce et al., "Dopamine D3 receptor antagonists as therapeutic agents," Drug Discovery Today, 2005, vol. 10, No. 13, pp. 917-925.
Joyce, J., "Dopamine D3 receptor as a therapeutic target for antipsychotic and antiparkinsonian drugs," Pharmacology & Therapeutics, 2001, vol. 90, pp. 231-259.
Arakawa et al., "Positron Emission Tomography Measurement of Dopamine D2 Receptor Occupancy in the Pituitary and Cerebral Cortex: Relation to Antipsychotic-Induced Hyperprolactinemia," Journal of Clinical Psychiatry, 2010, vol. 71, No. 9, pp. 1131-1137.

(Continued)

*Primary Examiner* — Heidi Reese
(74) *Attorney, Agent, or Firm* — Wenderoth, Lind & Ponack, L.L.P.

(57) ABSTRACT

Novel compounds having a D3 receptor antagonistic activity are provided.
The compound represented by Formula (I):

Formula (I):

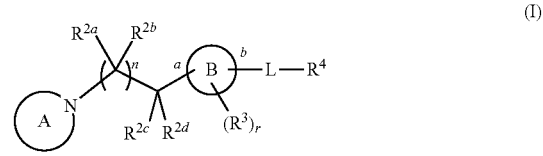

(I)

wherein Ring A is a non-aromatic heterocycle or the like substituted with substituted or unsubstituted aromatic heterocyclyl or the like; $R^{2a}$ to $R^{2d}$ are each independently a hydrogen atom or the like; n is an integer of 0 to 3; Ring B is a non-aromatic carbocycle or the like; $R^3$ is each independently halogen or the like; r is an integer of 0 to 4; -L- is $-N(R^{10})-C(=O)$, or the like; $R^{10}$ is a hydrogen atom or the like; $R^4$ is substituted or unsubstituted aromatic heterocyclyl or the like,
or a pharmaceutically acceptable salt thereof.

15 Claims, No Drawings

(56) References Cited

FOREIGN PATENT DOCUMENTS

| WO | 2006/108700 | 10/2006 |
|---|---|---|
| WO | 2006/108701 | 10/2006 |
| WO | 2006/133945 | 12/2006 |
| WO | 2006/133946 | 12/2006 |
| WO | 2006/136223 | 12/2006 |
| WO | 2007/022933 | 3/2007 |
| WO | 2007/022934 | 3/2007 |
| WO | 2007/022936 | 3/2007 |
| WO | 2007/022980 | 3/2007 |
| WO | 2007/113232 | 10/2007 |
| WO | 2007/113258 | 10/2007 |
| WO | 2007/113260 | 10/2007 |
| WO | 2007/148208 | 12/2007 |
| WO | 2008/022994 | 2/2008 |
| WO | 2008/125891 | 10/2008 |
| WO | 2009/013212 | 1/2009 |
| WO | 2009/043883 | 4/2009 |
| WO | 2009/043884 | 4/2009 |
| WO | 2009/056805 | 5/2009 |
| WO | 2009/095438 | 8/2009 |
| WO | 2009/112568 | 9/2009 |
| WO | 2010/025235 | 3/2010 |
| WO | 2010/031735 | 3/2010 |
| WO | 2010/034646 | 4/2010 |
| WO | 2010/034648 | 4/2010 |
| WO | 2010/034656 | 4/2010 |
| WO | 2011/161009 | 12/2011 |
| WO | 2012/004206 | 1/2012 |
| WO | 2012/080149 | 6/2012 |
| WO | 2012/110470 | 8/2012 |
| WO | 2012/117001 | 9/2012 |
| WO | 2012/121919 | 9/2012 |
| WO | 2012/150231 | 11/2012 |
| WO | 2014/059265 | 4/2014 |
| WO | 2014/064038 | 5/2014 |
| WO | 2014/086098 | 6/2014 |
| WO | 2014/140246 | 9/2014 |
| WO | 2014/180165 | 11/2014 |
| WO | 2016/067043 | 5/2016 |
| WO | 2017/021920 | 2/2017 |
| WO | 2017/064488 | 4/2017 |
| WO | 2018/021447 | 2/2018 |
| WO | 2019/146739 | 8/2019 |

OTHER PUBLICATIONS

Watson et al., "Selective Blockade of Dopamine D3 Receptors Enhances while D2 Receptor Antagonism Impairs Social Novelty Discrimination and Novel Object Recognition in Rats: A Key Role for the Prefrontal Cortex," Neuropsychopharmacology, 2012, vol. 37, pp. 770-786.

Mehta et al., "Dopamine D2 receptor occupancy levels of acutesulpiride challenges that produce working memory and learning impairments in healthy volunteers," Psychopharmacology, 2008, vol. 196, No. 1, pp. 157-165.

Uchida et al., "D2 Receptor Blockade by Risperidone Correlates With Attention Deficits in Late-Life Schizophrenia," Journal of Clinical Psychopharmacology. 2009, vol. 29, No. 6, pp. 571-575.

Barth et al., "In Vivo Occupancy of Dopamine D3 Receptors by Antagonists Produces Neurochemical and Behavioral Effects of Potential Relevance to Attention-Deficit-Hyperactivity Disorder," Journal of Pharmacology and Experimental Therapeutics, 2013, vol. 344, pp. 501-510.

Mach et al., "Development of Novel 1,2,3,4-Tetrahydroisoquinoline Derivatives and Closely Related Compounds as Potent and Selective Dopamine D3 Receptor Ligands," ChemBioChem, 2004, vol. 5, pp. 508-518.

Macdonald et al., "Design and Synthesis of trans-3-(2-(4-((3-(3-(5-Methyl-1,2,4-oxadiazolyl))-phenyl)carboxamido)cyclohexyl)ethl)-7-methylsulfonyl-2,3,4,5-tetrahydro-1H-3-benzazepine (SB-414796): A Potent and Selective Dopamine D3 Receptor Antagonist," Journal of Medicinal Chemistry, 2003, vol. 46, pp. 4952-4964.

Chen et al., "Synthesis and pharmacological characterization of novel N-(trans-4-(2-(4-(benzo[d]isothiazol-3-yl)piperazin-1-yl)ethyl)cyclohexyl) amines as potential multireceptor atypical antipsychotics," European Journal of Medicinal Chemistry, 2016, vol. 123, pp. 332-353.

Deak et al., "Physico-chemical characterization of a novel group of dopamine D3/D2 receptor ligands, potential atypical antipsychotic agents," Journal of Pharmaceutical and Biomedical Analysis, 2008, vol. 48, No. 3, pp. 678-684.

Agai-Csongor et al., "Novel sulfonamides having dual dopamine D2 and D3 receptor affinity show in vivo antipsychotic efficacy with beneficial cognitive and EPS profile," Bioorganic & Medicinal Chemistiy Letters, 2007, vol. 17, No. 19, pp. 5340-5344.

Wustrow et al., "Aminopyrimidines with High Affinity for Both Serotonin and Dopamine Receptors," Journal of Medicinal Chemistry, 1998, vol. 41, No. 5, pp. 760-771.

Belliotti et al., "Novel Cyclohexyl Amides as Potent and Selective D3 Dopamine Receptor Ligands," Bioorganic & Medicinal Chemistiy Letters, 1997, vol. 7, No. 18, pp. 2403-2408.

Micheli et al., "1,2,4-Triazolyl Azabicyclo[3.1.0]hexanes: A New Series of Potent and Selective Dopamine D3 Receptor Antagonists," Journal of Medicinal Chemistry, 2010, vol. 53, No. 1, pp. 374-391.

Micheli et al., "Exploration of the Amine Terminus in a Novel Series of 1,2,4-Triazolo-3-yl-azabicyclo[3.1.0]hexanes as Selective Dopamine D3 Receptor Antagonists," Journal of Medicinal Chemistry, 2010, vol. 53, No. 19, pp. 7129-7139.

Micheli et al., "A specific and direct comparison of the trifluoromethyl and pentafluoro sulfanyl groups on the selective dopamine D3 antagonist 3-(3-{[4-methyl-5-(4-mthyl-1,3-oxazol-5-yl)-4H-1,2,4-triazol-3-yl)thio}propyl)-1-phenyl-3-azabicyclo[3.1.0]-hexane template," Bioorganic & Medicinal Chemistry Letters, 2010, vol. 20, pp. 4566-4568.

Micheli et al., "[3-Azabicyclo[3.1.0]hex-1-yl]phenyl-benzenesulfonamides as selective dopamine D3 antagonists," Bioorganic &Medicinal Chemistry Letters, 2010, vol. 20, No. 18, pp. 5491-5494.

Bonanomi et al., "Triazolyl Azabicyclo[3.1.0]hexanes: a Class of Potent and Selective Dopamine D3 Receptor Antagonists," Chem Med Chem, 2010, vol. 5, No. 5, pp. 705-715.

Chen et al., "Tranylcypromine Substituted cis-Hydroxycyclobutylnaphthamides as Potent and Selective Dopamine D3 Receptor Antagonists," Journal of Medicinal Chemistry, 2014, vol. 57, pp. 4962-4968.

Chen et al., "High-affinity and selective dopamine D3 receptor full agonists," Bioorganic & Medicinal Chemistry Letters, 2012, vol. 22, No. 17, pp. 5612-5617.

Ortore et al., "Different Binding Modes of Structurally Diverse Ligands for Human D3DAR," Journal of Chemical Information and Modeling, 2010, vol. 50, No. 12, pp. 2162-2175.

Kim et al., "Classification of dopamine antagonists using functional feature hypothesis and topological descriptors," Bioorganic & Medicinal Chemistry, 2006, vol. 14, No. 5, pp. 1454-1461.

Heidbreder et al., "The role of central dopamine D3 receptors in drug addiction: a review of pharmacological evidence," Brain Research Reviews, 2005, vol. 49, No. 1, pp. 77-105.

Stemp et al., "Design and Synthesis of trans-N-[4-[2-(6-Cyano-1,2,3,4-tetrahydroisoquinolin-2-yl)ethyl]cyclohexyl]-4-quinolinecarboxamide (SB-277011): A Potent and Selective Dopamine D3 Receptor Antagonist with High Oral Bioavailability and CNS Penetration in the Rat," Journal of Medicinal Chemistry, 2000, vol. 43, No. 9, pp. 1878-1885.

Kumar et al., "Synthesis and Pharmacological Characterization of Novel trans-Cyclopropylmethyl-Linked Bivalent Ligands That Exhibit Selectivity and Allosteric Pharmacology at the Dopamine D3 Receptor (D3R)," Journal of Medicinal Chemistry, 2017, vol. 60, pp. 1478-1494.

Gadhiya et al., "New Dopamine D3-Selective Receptor Ligands Containing a 6-Methoxy-1,2,3,4-tetrahydroisoquinolin-7-ol Motif," ACS Medicinal Chemistry Letters, 2018, vol. 9, pp. 990-995.

(56) References Cited

OTHER PUBLICATIONS

Chen et al., "Design of Novel hexhydropyrazinoquino lines as potent and selective dopamine D3 receptor ligands with improved solubility," Bioorganic & Medicinal Chemistry Letters, 2006, vol. 16, pp. 443-446.
Micheli et al., "New fused benzazepine as selective D3 receptor antagonists. Synthesis and biological evaluation. Part 2: [g]-Fused and hetero-fused systems," Bioorganic & Medicinal Chemistry Letters, 2008, vol. 18, pp. 908-912.
Chen et al., "Pramipexole Derivatives as Potent and Selective Dopamine D3 Receptor Agonists with Improved Human Microsomal Stability," ChemMedChem, 2014, vol. 9, pp. 2653-2660.
Vass et al., "Multiple Fragment Docking and Linking in Primary and Secondary Pockets of Dopamine Receptors," ACS Medicinal Chemistry Letters, 2014, vol. 5, pp. 1010-1014.
Chen et al., "CJ-1639: A Potent and Highly Selective Dopamine D3 Receptor Full Agonist," ACS Medicinal Chemistry Letters, 2011, vol. 2, pp. 620-625.
Brindisi et al., "Targeting Dopamine D3 and Serotonin 5-HT1A and 5-HT2A Receptors for Developing Effective Antipsychotics: Synthesis, Biological Characterization, and Behavioral Studies," Journal of Medicinal Chemistry, 2014, vol. 57, pp. 9578-9597.
Keck et al., "Identifying Medication Targets for Psychostimulant Addiction: Unraveling the Dopamine D3 Receptor Hypothesis," Journal of Medicinal Chemistry, 2015, vol. 58, pp. 5361-5380.
Tschammer et al., "Highly Potent 5-Aminotetrahydropyrazolopyridines: Enantioselective Dopamine D3 Receptor Binding, Functional Selectivity, and Analysis of Receptor-Ligand Interactions," Journal of Medicinal Chemistry, 2011, vol. 54, pp. 2477-2491.
Jordan et al., "The highly selective dopamine DR antagonist, R-VK4-40 attenuates oxycodone reward and augments analgesia in rodents," Neuropharmacology, 2019, vol. 158, 107597, pp. 1-11.
Shonberg et al., "Structure-Activity Study of N-((trans)-4-(2-(7-Cyano-3,4-dihydroisoquinolin-2(1H)-yl)ethyl)cyclohexyl)-1H-indole-2-carboxamide (SB269652), a Bitopic Ligand That Acts as a Negative Allosteric Modulator of the Dopamine D2 Receptor," Journal of Medicinal Chemistry, 2015, vol. 58, pp. 5287-5307.
Translation of The International Preliminary Report on Patentability dated Aug. 6, 2020 in International (PCT) Application No. PCT/JP2019/002397.

\* cited by examiner

CYCLIC COMPOUND HAVING DOPAMINE D3 RECEPTOR ANTAGONISTIC EFFECT

TECHNICAL FIELD

The present invention relates to a compound which has an antagonistic activity for dopamine D3 receptor (hereinafter referred to as D3 receptor) and is useful as an agent for treating and/or preventing diseases induced by D3 receptor, or a pharmaceutically acceptable salt thereof, and a pharmaceutical composition containing the compound.

BACKGROUND ART

Dopamine is an important neuromediator in central nervous system. The biological activities of dopamine are mediated through G protein-coupled receptors (GPCRs) and involved in the regulation of a variety of functions which include emotion, cognition, and motor functions. In human, five different dopamine receptors D1 to D5 have been identified. These receptors can be divided into two subtypes: D2-like receptors consisting of D2, D3 and D4 receptors, and D1-like receptors consisting of D1 and D5 receptors.

D3 receptor is selectively distributed in marginal brain area, such as nucleus accumbens, Calleja island, olfactory tubercle. Some research reports suggest that D3 receptor antagonists are useful for treating and/or preventing a number of neurosises, such as schizophrenia, Parkinson's disease, drug dependence, any forms of stress, anxiety, and somnipathy. Furthermore, it is considered that D3/D2 selective D3 receptor antagonists would have less D2 receptor-mediated side-effects (extrapyramidal symptom, elevated prolactin, reduced cognitive function, and the like) compared to existing antipsychotics which are D2 receptor antagonists (Non-patent Documents 1 to 6).

It is also suggested that D3 receptor antagonists are useful for treating and/or preventing attention-deficit/hyperactivity disorder (AD/HD) (Non-patent Document 7).

Thus, it is highly likely that compounds having antagonistic activity for D3 receptor, particularly preferably compounds having high D3/D2 selectivity, are useful as an agent for treating and/or preventing diseases associated with D3 receptor.

The compounds having affinity for D3 receptor are described in Patent Documents 1 to 35, and Non-patent Documents 8 to 19. However, substantially disclosed compounds have different structure from the compounds of the present invention.

PRIOR ART REFERENCES

Patent Documents

[Patent Document 1] WO 2014/180165
[Patent Document 2] WO 2014/086098
[Patent Document 3] WO 2012/150231
[Patent Document 4] WO 2012/117001
[Patent Document 5] WO 2012/110470
[Patent Document 6] WO 2012/080149
[Patent Document 7] WO 2012/004206
[Patent Document 8] WO 2011/161009
[Patent Document 9] WO 2010/031735
[Patent Document 10] WO 2010/034656
[Patent Document 11] WO 2010/034648
[Patent Document 12] WO 2010/034646
[Patent Document 13] US 2009/0143398
[Patent Document 14] WO 2009/013212
[Patent Document 15] WO 2008/125891
[Patent Document 16] WO 2007/148208
[Patent Document 17] WO 2006/082456
[Patent Document 18] WO 2005/012266
[Patent Document 19] WO 2003/029233
[Patent Document 20] WO 2009/043884
[Patent Document 21] WO 2009/043883
[Patent Document 22] WO 2008/022994
[Patent Document 23] WO 2007/113260
[Patent Document 24] WO 2007/113258
[Patent Document 25] WO 2007/113232
[Patent Document 26] WO 2007/022980
[Patent Document 27] WO 2007/022934
[Patent Document 28] WO 2007/022936
[Patent Document 29] WO 2007/022933
[Patent Document 30] WO 2006/136223
[Patent Document 31] WO 2006/133946
[Patent Document 32] WO 2006/133945
[Patent Document 33] WO 2006/108701
[Patent Document 34] WO 2006/108700
[Patent Document 35] WO 2005/080382
[Patent Document 36] WO 2018/021447

Non-Patent Documents

[Non-patent Document 1] Drug Discovery Today, 2005, 10(13), 917-925
[Non-patent Document 2] Pharmacology & Therapeutics, 2001, 90, 231-259
[Non-patent Document 3] Journal of Clinical Psychiatry, 2010, 71(9), 1131-1137
[Non-patent Document 4] Neuropsychopharmacology, 2012, 37, 770-786
[Non-patent Document 5] Psychopharmacology, 2008, 196 (1), 157-165
[Non-patent Document 6] Journal of Clinical Psychopharmacology, 2009, 29(6), 571-575
[Non-patent Document 7] Journal of Pharmacology and Experimental Therapeutics, 2013, 344, 501-510
[Non-patent Document 8] ChemBioChem, 2004, 5, 508-518
[Non-patent Document 9] Journal of Medicinal Chemistry, 2003, 46, 4952-4964
[Non-patent Document 10] European Journal of Medicinal Chemistry, 2016, 123, 332-353
[Non-patent Document 11] Journal of Pharmaceutical and Biomedical Analysis, 2008, 48(3), 678-684
[Non-patent Document 12] Bioorganic & Medicinal Chemistry Letters, 2007, 17(19), 5340-5344
[Non-patent Document 13] Journal of Medicinal Chemistry, 1998, 41(5), 760-771
[Non-patent Document 14] Bioorganic & Medicinal Chemistry Letters, 1997, 7(18), 2403-2408
[Non-patent Document 15] Journal of Medicinal Chemistry, 2010, 53(1), 374-391
[Non-patent Document 16] Journal of Medicinal Chemistry, 2010, 53(19), 7129-7139
[Non-patent Document 17] Bioorganic & Medicinal Chemistry, 2010, 20, 4566-4568
[Non-patent Document 18] Bioorganic & Medicinal Chemistry Letters, 2010, 20(18), 5491-5494
[Non-patent Document 19] Chem Med Chem, 2010, 5(5), 705-715

SUMMARY OF THE INVENTION

Problems to be Solved by the Invention

The objective of the present invention is to provide a compound which has an antagonistic activity for D3 receptor, and preferably high D3/D2 selectivity, and is useful as a therapeutic and/or preventive agent for diseases associated with D3 receptor, or a pharmaceutically acceptable salt thereof, and a pharmaceutical composition containing the compound.

Means for Solving the Problems

The present invention relates to, for example, the following inventions.
(1) A compound represented by Formula (I):

[Chemical Formula 1]

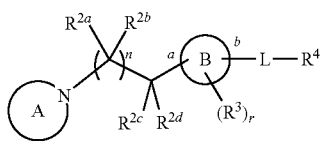
(I)

wherein a group represented by:

[Chemical Formula 2]

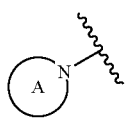

is

[Chemical Formula 3]

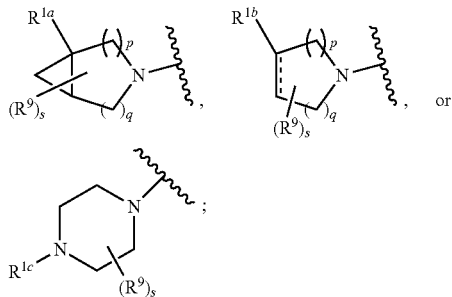

wherein the dashed line represents the presence or absence of a bond;
p and q are each independently 1 or 2, provided that p and q are not simultaneously 2;
$R^{1a}$ to $R^{1c}$ are each independently substituted or unsubstituted aromatic heterocyclyl, or substituted or unsubstituted aromatic carbocyclyl;
$R^9$ is each independently halogen, hydroxy, cyano, substituted or unsubstituted alkyl, or substituted or unsubstituted alkyloxy;
two $R^9$s attached to different ring-constituting atoms may be taken together to form a substituted or unsubstituted (C1-C3) bridge wherein one of carbon atoms constituting the (C1-C3) bridge may be replaced with an oxygen atom or a nitrogen atom;
s is an integer of 0 to 4;
n is an integer of 0 to 3;
$R^{2a}$ is each independently a hydrogen atom, halogen, hydroxy, cyano, substituted or unsubstituted alkyl, or substituted or unsubstituted alkyloxy;

$R^{2b}$ is each independently a hydrogen atom, halogen, hydroxy, cyano, substituted or unsubstituted alkyl, or substituted or unsubstituted alkyloxy;
$R^{2c}$ and $R^{2d}$ are each independently a hydrogen atom, halogen, hydroxy, cyano, substituted or unsubstituted alkyl, or substituted or unsubstituted alkyloxy;
-L- is $-N(R^{10})-C(=O)-$ or $-N(R^{10})-SO_2-$;
a bonding hand "a" is bonded to $-CR^{2c}R^{2d}-$;
a bonding hand "b" is bonded to $-N(R^{10})-$;
$R^{10}$ is a hydrogen atom, or substituted or unsubstituted alkyl;
Ring B is a non-aromatic carbocycle or a non-aromatic heterocycle;
r is an integer of 0 to 4;
$R^3$ is each independently halogen, hydroxy, cyano, substituted or unsubstituted alkyl, or substituted or unsubstituted alkyloxy;
two $R^3$s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom; and
$R^4$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
provided that
(i) when a group represented by:

[Chemical Formula 4]

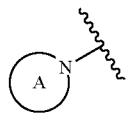

is

[Chemical Formula 5]

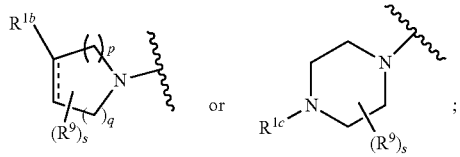

then n is 1;
(ii) when (α) $R^{1b}$ is substituted or unsubstituted aromatic carbocyclyl, or
(β) $R^{1c}$ is substituted or unsubstituted 6-membered aromatic heterocyclyl,
then Ring B is a 4- to 8-membered non-aromatic carbocycle or a 4- to 8-membered non-aromatic heterocycle;
$R^4$ is substituted or unsubstituted 6-membered or bicyclic non-aromatic heterocyclyl, substituted or unsubstituted 6-membered or bicyclic aromatic heterocyclyl, $-CR^{5a}R^{5b}-R^6$, or $-CR^{7a}=CR^{7b}-R^8$;
$R^{5a}$, $R^{5b}$, $R^{7a}$ and $R^{7b}$ are each independently a hydrogen atom, halogen, substituted or unsubstituted C1-C6 alkyl, or substituted or unsubstituted C1-C6 alkyloxy;
$R^6$ is substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy; and $R^8$ is substituted or unsubstituted non-aromatic carbocyclyl, substituted or unsubstituted aromatic carbocyclyl, substituted or unsubstituted non-aromatic heterocyclyl, or substituted or unsubstituted aromatic heterocyclyl; and (iii) when (α) $R^{1b}$ is substituted or unsubstituted bicyclic aromatic heterocyclyl, or (β) $R^{1c}$ is substituted or unsubstituted bicyclic aromatic heterocyclyl or substituted or unsubstituted aromatic carbocyclyl, then Ring B is a 4- to 8-membered non-aromatic carbocycle or a 4- to 8-membered non-aromatic heterocycle;

$R^4$ is substituted or unsubstituted indazolyl, substituted or unsubstituted pyrazolopyridine, substituted or unsubstituted benzotriazolyl, substituted or unsubstituted isoindolinyl, substituted or unsubstituted dihydroisoquinolinyl, substituted or unsubstituted dihydropyridyl, —$CR^{5a}R^{5b}$—$R^6$, or —$CR^{7a}$=$CR^{7b}$—$R^8$;

$R^6$ is substituted or unsubstituted oxazolyl, substituted or unsubstituted isoxazolyl, substituted or unsubstituted oxadiazolyl, substituted or unsubstituted pyrazolyl, substituted or unsubstituted triazolyl, substituted or unsubstituted thiazolyl, substituted or unsubstituted thiadiazolyl, substituted or unsubstituted pyrimidinyl, substituted or unsubstituted pyrimidinyloxy, substituted or unsubstituted pyrazinyloxy, or substituted or unsubstituted isoxazolyloxy; and $R^{5a}$, $R^{5b}$, $R^{7a}$, $R^{7b}$ and $R^8$ are the same as defined in above (ii), provided that the following compound:

[Chemical Formula 6]

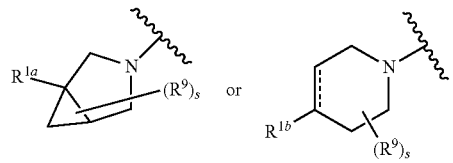

is excluded,
or a pharmaceutically acceptable salt thereof.

(2) The compound according to above (1), wherein
$R^{1b}$ is substituted or unsubstituted 5- to 6-membered aromatic heterocyclyl,
$R^{1c}$ is substituted or unsubstituted 5-membered aromatic heterocyclyl,
or a pharmaceutically acceptable salt thereof.

(3) The compound according to above (1) or (2), wherein $R^{1a}$ to $R^{1c}$ are each independently substituted or unsubstituted 5-membered aromatic heterocyclyl, or a pharmaceutically acceptable salt thereof.

(4) The compound according to any one of above (1) to (3), wherein $R^{1a}$ to $R^{1c}$ are each independently substituted or unsubstituted isoxazolyl, or a pharmaceutically acceptable salt thereof.

(5) The compound according to any one of above (1) to (4), wherein $R^{1a}$ to $R^{1c}$ are each independently a group represented by:

[Chemical Formula 7]

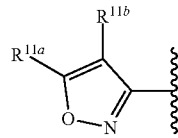

wherein $R^{11a}$ and $R^{11b}$ are each independently a hydrogen atom, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, provided that $R^{11a}$ and $R^{11b}$ are not simultaneously hydrogen atoms, or a pharmaceutically acceptable salt thereof.

(6)'
The compound according to any one of above (1) to (5), wherein a group represented by:

[Chemical Formula 8]

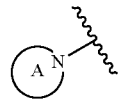

is:

[Chemical Formula 9]

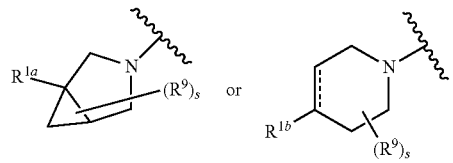

wherein $R^9$ and s are the same as defined in above (1);

$R^{1a}$ is:

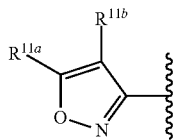
[Chemical Formula 10]

wherein $R^{11a}$ is substituted or unsubstituted alkyl, substituted or unsubstituted non-aromatic carbocyclyl, or substituted or unsubstituted alkylcarbonyl; and $R^{11b}$ is a hydrogen atom; and
$R^{1b}$ is:

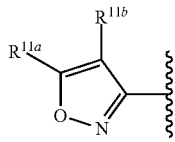
[Chemical Formula 11]

wherein $R^{11a}$ is a hydrogen atom; and $R^{11b}$ is substituted or unsubstituted aromatic carbocyclyl, substituted or unsubstituted non-aromatic carbocyclyl, or substituted or unsubstituted alkyl,
or a pharmaceutically acceptable salt thereof.
(6) The compound according to any one of above (1) to (5) and (6)', wherein $R^{11a}$ is substituted or unsubstituted alkyl, or substituted or unsubstituted alkylcarbonyl; and $R^{11b}$ is a hydrogen atom,
or a pharmaceutically acceptable salt thereof.
(7)' The compound according to any one of above (1) to (6) and (6)', wherein $R^{11a}$ is C1-C6 alkyl optionally substituted with one or more group(s) selected from (monocyclic non-aromatic carbocyclyl substituted with halogen; monocyclic non-aromatic carbocyclyl; and halogen), or monocyclic non-aromatic carbocyclyl optionally substituted with one or more group(s) selected from (halogen; C1-C6 alkyl; and C1-C6 haloalkyl); and $R^{11b}$ is a hydrogen atom,
or a pharmaceutically acceptable salt thereof.
(7)
The compound according to any one of the above (1) to (6), (6)' and (7)', wherein a group represented by:

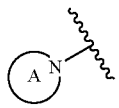
[Chemical Formula 12]

is:

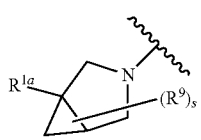
[Chemical Formula 13]

wherein each symbol is the same as defined in above (1), or a pharmaceutically acceptable salt thereof.

(8)
The compound according to any one of the above (1) to (6), (6)' and (7)', wherein a group represented by:

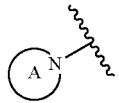
[Chemical Formula 14]

is:

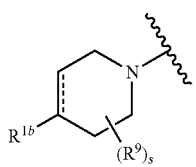
[Chemical Formula 15]

wherein each symbol is the same as defined in above (1), or a pharmaceutically acceptable salt thereof.
(9) The compound according to any one of the above (1) to (8), (6)', and (7)', wherein
$R^4$ is substituted or unsubstituted aromatic carbocyclyl, substituted or unsubstituted non-aromatic carbocyclyl, substituted or unsubstituted non-aromatic heterocyclyl, substituted or unsubstituted aromatic heterocyclyl, $—CR^{5a}R^{5b}—R^6$, or $—CR^{7a}=CR^{7b}—R^8$;
$R^{5a}$, $R^{5b}$, $R^{7a}$ and $R^{7b}$ are each independently a hydrogen atom, halogen, substituted or unsubstituted C1-C6 alkyl, or substituted or unsubstituted C1-C6 alkyloxy;
$R^6$ is substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy; and
$R^8$ is substituted or unsubstituted non-aromatic carbocyclyl, substituted or unsubstituted aromatic carbocyclyl, substituted or unsubstituted non-aromatic heterocyclyl, or substituted or unsubstituted aromatic heterocyclyl, or a pharmaceutically acceptable salt thereof.
(10)
The compound according to any one of above (1) to (9), (6)', and (7)', wherein
$R^4$ is substituted or unsubstituted phenyl, substituted or unsubstituted indazolyl, substituted or unsubstituted pyrazolopyridyl, substituted or unsubstituted benzotriazolyl, substituted or unsubstituted pyridyl, substituted or unsubstituted isoindolinyl, substituted or unsubstituted dihydroisoquinolinyl, substituted or unsubstituted dihydropyridyl, $—CR^{5a}R^{5b}—R^6$, or $—CR^{7a}=CR^{7b}—R^8$;
$R^6$ is substituted or unsubstituted oxazolyl, substituted or unsubstituted isoxazolyl, substituted or unsubstituted oxadiazolyl, substituted or unsubstituted pyrazolyl, substituted or unsubstituted triazolyl, substituted or unsubstituted thiazolyl, substituted or unsubstituted thiadiazolyl, substituted or unsubstituted pyrimidinyl, substituted or unsubstituted pyrimidinyloxy, substituted or unsubstituted pyrazinyloxy, or substituted or unsubstituted isoxazolyloxy; and R⁸ is substituted or unsubstituted pyrimidinyl, or substituted or unsubstituted pyrazolyl,
or a pharmaceutically acceptable salt thereof.

(11) The compound according to any one of above (1) to (10), (6)', and (7)', wherein Ring B is a 4- to 8-membered non-aromatic carbocycle or a 4- to 8-membered non-aromatic heterocycle, or a pharmaceutically acceptable salt thereof.

(12) The compound according to any one of above (1) to (11), (6)', and (7)', wherein $R^{2a}$ to $R^{2d}$, $R^{5a}$, $R^{5b}$, $R^{7a}$, and $R^{7b}$ are hydrogen atoms, or a pharmaceutically acceptable salt thereof.

(12)' The compound according to any one of above (1) to (12), (6)', and (7)', wherein n is 1; and Ring B is a 4- to 8-membered non-aromatic carbocycle or a 4- to 8-membered non-aromatic heterocycle, or a pharmaceutically acceptable salt thereof.

(13)' The compound according to any one of above (1) to (12), (6)', (7)', and (12)', wherein
$R^{2a}$ to $R^{2d}$, $R^{5a}$, $R^{5b}$, $R^{7a}$, and $R^{7b}$ bare hydrogen atoms;
s is 0; r is 0 or 1; and
-L- is —NH—C(=O)—,
or a pharmaceutically acceptable salt thereof.

(13) The compound according to any one of above (1) to (12), (6)', (7)', (12), and (13)', wherein r and s are 0, or a pharmaceutically acceptable salt thereof.

(14) The compound according to any one of above (1) to (13), (6)', (7)', (12)', and (13)', wherein n is 1, or a pharmaceutically acceptable salt thereof.

(15) The compound according to any one of above (1) to (14), (6)', (7)', (12)', and (13)', wherein -L- is —NH—C(=O)—,
or a pharmaceutically acceptable salt thereof.

(14)' The compound according to any one of above (1) to (15), (6)', (7)', (12)', and (13)', wherein the compound is selected from the group consisting of Examples I-036, I-038, I-039, I-042, I-046, 1-052, I-053, I-055, I-056, I-1, II-2, II-3, II-4, and II-5, or a pharmaceutically acceptable salt thereof.

(16) A pharmaceutical composition comprising the compound according to any one of above (1) to (15), (6)', (7)', and (12)' to (14)', or a pharmaceutically acceptable salt thereof.

(17) The pharmaceutical composition according to above (16), wherein the composition is a dopamine D3 receptor antagonist.

(17A) The pharmaceutical composition according to above (16), wherein the composition has an antagonistic activity for dopamine D3 receptor.

(18) A dopamine D3 receptor antagonist comprising the compound according to any one of above (1) to (15), (6)', (7)', and (12)' to (14)', or a pharmaceutically acceptable salt thereof.

(19) The pharmaceutical composition according to any one of above (16), (17) and (17A), having effect for treating and/or preventing diseases associated with dopamine D3 receptor.

(20) The pharmaceutical composition according to any one of above (16), (17) and (17A), having effect for treating and/or preventing cognitive disorder, drug addiction, depression, anxiety, drug dependence, gambling addiction, dementia, memory impairment, schizophrenia, schizoaffective disorder, bipolar disorder, mania, psychotic disorders including psychotic depression, psychoses including paranoia and delusion, attention-deficit/hyperactivity disorder, addiction, and/or obsessive compulsive disorder.

(21) The pharmaceutical composition according to any one of above (16), (17) and (17A), having effect for treating and/or preventing attention-deficit/hyperactivity disorder.

(22) A method for treating and/or preventing a disease associated with D3 receptor, comprising administering the compound according to any one of above (1) to (15), (6)', (7)', and (12)' to (14)', or a pharmaceutically acceptable salt thereof.

(23) A method for treating and/or preventing cognitive disorder, drug addiction, depression, anxiety, drug dependence, gambling addiction, dementia, memory impairment, schizophrenia, schizoaffective disorder, bipolar disorder, mania, psychotic disorders including psychotic depression, psychoses including paranoia and delusion, attention-deficit/hyperactivity disorder, addiction, and/or obsessive compulsive disorder, comprising administering the compound according to any one of above (1) to (15), (6)', (7)', and (12)' to (14)', or a pharmaceutically acceptable salt thereof.

(24) A method for treating and/or preventing attention-deficit/hyperactivity disorder, comprising administering the compound according to any one of above (1) to (15), (6)', (7)', and (12)' to (14)', or a pharmaceutically acceptable salt thereof.

(25) Use of the compound according to any one of above (1) to (15), (6)', (7)', and (12)' to (14)', or a pharmaceutically acceptable salt thereof, for manufacturing a therapeutic and/or preventive agent for diseases associated with D3 receptor.

(26) Use of the compound according to any one of above (1) to (15), (6)', (7)', and (12)' to (14)', or a pharmaceutically acceptable salt thereof, for manufacturing a therapeutic and/or preventive agent for cognitive disorder, drug addiction, depression, anxiety, drug dependence, gambling addiction, dementia, memory impairment, schizophrenia, schizoaffective disorder, bipolar disorders, mania, psychotic disorder including psychotic depression, psychoses including paranoia and delusion, attention-deficit/hyperactivity disorder, addiction, and/or obsessive compulsive disorder.

(27) Use of the compound according to any one of above (1) to (15), (6)', (7)', and (12)' to (14)', or a pharmaceutically acceptable salt thereof, for manufacturing a therapeutic and/or preventive agent for attention-deficit/hyperactivity disorder.

(28) The compound according to any one of above (1) to (15), (6)', (7)', and (12)' to (14)', or a pharmaceutically acceptable salt thereof for use in treating and/or preventing diseases associated with D3 receptor.

(29) The compound according to any one of above (1) to (15), (6)', (7)', and (12)' to (14)', or a pharmaceutically acceptable salt thereof, for use in treating and/or preventing cognitive disorder, drug addiction, depression, anxiety, drug dependence, gambling addiction, dementia, memory impairment, schizophrenia, schizoaffective disorder, bipolar disorder, mania, psychotic disorder including psychotic depression, psychoses including paranoia and delusion, attention-deficit/hyperactivity disorder, addiction, and/or obsessive compulsive disorder.

(37) The compound according to any one of above (1) to (15), (6)', (7)', and (12)' to (14)', or a pharmaceutically acceptable salt thereof, for use in treating and/or preventing attention-deficit/hyperactivity disorder.

(101) A pharmaceutical composition comprising the compound according to any one of above (1) to (15), (6)', (7)', and (12)' to (14)', or a pharmaceutically acceptable salt thereof, for oral administration.

(102) The pharmaceutical composition according to (101), which is a tablet, a powder, a granule, a capsule, a pill, a film, a suspension, an emulsion, an elixir, a syrup, a lemonade, a spirit, an aromatic water, an extract, a decoction, or a tincture.

(103) The pharmaceutical composition according to (102), which is a sugar-coated tablet, a film-coated tablet, an enteric-coated tablet, a sustained-release tablet, a troche tablet, a sublingual tablet, a buccal tablet, a chewable tablet, an orally disintegrating tablet, a dry syrup, a soft capsule, a micro capsule or a sustained-release capsule.

(104) A pharmaceutical composition comprising the compound according to any one of above (1) to (15), (6)', (7)', and (12)' to (14)', or a pharmaceutically acceptable salt thereof, for parenteral administration.

(105) The pharmaceutical composition according to (104), for dermal, subcutaneous, intravenous, intraarterial, intramuscular, intraperitoneal, transmucosal, inhalation, transnasal, ophthalmic, inner ear or vaginal administration.

(106) The pharmaceutical composition according to (104) or (105), which is an injection, an infusion, an eye drop, a nose drop, an ear drop, an aerosol, an inhalation, a lotion, an impregnation, a liniment, a mouthwash, an enema, an ointment, a plaster, a jelly, a cream, a patch, a cataplasm, an external powder or a suppository.

(107) A pharmaceutical composition comprising the compound according to any one of above (1) to (15), (6', (7)', and (12)' to (14)', or a pharmaceutically acceptable salt thereof, for a pediatric or geriatric patient.

Effect of the Invention

The compounds of the present invention have an antagonistic activity for D3 receptor, and preferably have high D3/D2 selectivity, and are useful as a therapeutic agent and/or preventive agent for diseases associated with D3 receptor.

Mode for Carrying Out the Invention

The meaning of each term used in the present description is explained below. Each term, unless otherwise indicated, is used in the same sense when used alone, or when used in combination with other term.

The term "consisting of" means having only components.

The term "comprising" means not restricting with components and not excluding undescribed factors.

"Halogen" includes a fluorine atom, a chlorine atom, a bromine atom, and an iodine atom. A fluorine atom and a chlorine atom are preferable. A fluorine atom is particularly preferable.

"Alkyl" includes a C1 to C15, preferably C1 to C10, more preferably C1 to C6, further preferably C1 to C4 linear or branched hydrocarbon group. Examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl and the like.

Examples of preferred embodiments of "alkyl" include methyl, ethyl, n-propyl, isopropyl, n-butyl, isobutyl, sec-butyl, tert-butyl, and n-pentyl. Examples of more preferred embodiments include methyl, ethyl, n-propyl, isopropyl, and tert-butyl.

"Alkenyl" includes a C2 to C15, preferably C2 to C10, more preferably C2 to C6, further preferably C2 to C4 linear or branched hydrocarbon group having one or more double bond(s) at any position(s). Examples thereof include vinyl, allyl, propenyl, isopropenyl, butenyl, isobutenyl, prenyl, butadienyl, pentenyl, isopentenyl, pentadienyl, hexenyl, iso-hexenyl, hexadienyl, heptenyl, octenyl, nonenyl, decenyl, undecenyl, dodecenyl, tridecenyl, tetradecenyl, and pentadecenyl and the like.

Examples of preferred embodiments of "alkenyl" include vinyl, allyl, propenyl, isopropenyl, and butenyl.

"Alkynyl" includes a C2 to C10, preferably C2 to C8, more preferably C2 to C6, further preferably C2 to C4 linear or branched hydrocarbon group having one or more triple bond(s) at any position(s). Furthermore, it may have double bond(s) at any position(s). Examples thereof include ethynyl, propynyl, butynyl, pentynyl, hexynyl, heptynyl, octynyl, nonynyl, and decynyl and the like.

Examples of preferred embodiments of "alkynyl" include ethynyl, propynyl, butynyl, and pentynyl.

"Aromatic carbocycle" means a cyclic aromatic hydrocarbon ring which is monocyclic or polycyclic having two or more rings. Examples thereof include benzene, naphthalene, anthracene, and phenanthrene and the like.

Examples of preferred embodiments of "aromatic carbocycle" include benzene.

"Aromatic carbocyclyl" means a cyclic aromatic hydrocarbon group which is monocyclic or polycyclic having two or more rings. Examples thereof include phenyl, naphthyl, anthryl, and phenanthryl and the like.

Examples of preferred embodiments of "aromatic carbocyclyl" include phenyl.

"Non-aromatic carbocycle" means a cyclic saturated hydrocarbon ring or a cyclic unsaturated non-aromatic hydrocarbon ring, which is monocyclic or polycyclic having two or more rings. The non-aromatic carbocycle which is polycyclic having two or more rings includes a fused ring wherein a non-aromatic carbocycle, which is monocyclic or polycyclic having two or more rings, is fused with a ring of the above "aromatic carbocycle".

In addition, "non-aromatic carbocycle" includes a ring having a bridge or a spiro ring as follows.

[Chemical Formula 16]

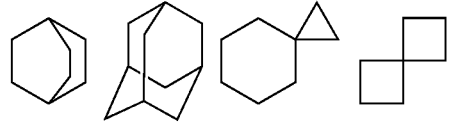

Examples of preferred embodiments of "spiroheptane ring" include a ring shown below.

[Chemical Formula 17]

The non-aromatic carbocycle which is monocyclic is preferably C3 to C16, more preferably C3 to C12, and further preferably C3 to C6 carbocycle. Examples thereof include "6-membered non-aromatic carbocycle" such as cyclohexane, cyclohexene, and cyclohexadiene, cyclopropane, cyclobutane, cyclopentane, cycloheptane, cyclooctane, cyclononane, cyclodecane, cyclopropene, cyclobutene, cyclopentene, and cycloheptene and the like.

Examples of the non-aromatic carbocycle which is polycyclic having two or more rings include indane, indene, acenaphthalene, tetrahydronaphthalene, and fluorene and the like.

"Non-aromatic carbocyclyl" means a cyclic saturated hydrocarbon group or a cyclic unsaturated non-aromatic hydrocarbon group, which is monocyclic or polycyclic having two or more rings. "Non-aromatic carbocyclyl" which is polycyclic having two or more rings includes a fused ring group wherein a non-aromatic carbocyclyl which is monocyclic or polycyclic having two or more rings is fused with a ring of the above "aromatic carbocyclyl".

In addition, "non-aromatic carbocyclyl" includes a group having a bridge or a group to form a spiro ring as follows:

[Chemical Formula 18]

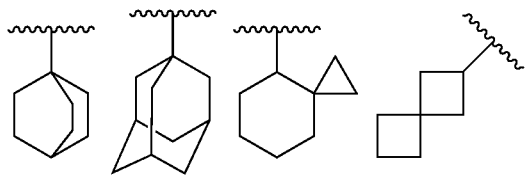

The non-aromatic carbocyclyl which is monocyclic is preferably C3 to C16, more preferably C3 to C12, and further preferably C3 to C6 carbocyclyl. Examples thereof include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl and the like.

Examples of the non-aromatic carbocyclyl which is polycyclic having two or more rings include indanyl, indenyl, acenaphthyl, tetrahydronaphthyl, and fluorenyl and the like.

"Aromatic heterocycle" means an aromatic ring, which is monocyclic or polycyclic having two or more rings, containing one or more identical or different heteroatoms selected independently from O, S and N in the ring.

Aromatic heterocycle which is polycyclic having two or more rings includes a fused ring wherein an aromatic heterocycle which is monocyclic or polycyclic having two or more rings is fused with a ring of the above "aromatic carbocycle".

The aromatic heterocycle which is monocyclic is preferably a 5- to 8-membered, and more preferably 5- or 6-membered ring. Examples thereof include "5-membered aromatic heterocycle" such as pyrrole, imidazole, pyrazole, triazole, tetrazole, furan, thiophene, isoxazole, oxazole, oxadiazole, isothiazole, thiazole, and thiadiazole and the like, and "6-membered aromatic heterocycle" such as pyridine, pyridazine, pyrimidine, pyrazine, and triazine and the like.

Examples of the aromatic heterocycle which is bicyclic include indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, pyrazolopyridin, imidazopyridine, triazolopyridine, imidazothiazole, pyrazinopyridazine, oxazolopyridine, and thiazolopyridine and the like.

Examples of the aromatic heterocycle which is polycyclic having three or more rings include carbazole, acridine, xanthene, phenothiazine, phenoxathiine, phenoxazine, and dibenzofuran and the like.

"Aromatic heterocyclyl" means an aromatic cyclyl, which is monocyclic or polycyclic having two or more rings, containing one or more identical or different heteroatoms selected independently from O, S and N in the ring. "Aromatic heterocyclyl" which is polycyclic having two or more rings includes a fused ring group wherein an aromatic heterocyclyl which is monocyclic or polycyclic having two or more rings is fused with a ring of the above "aromatic carbocyclyl".

The aromatic heterocyclyl which is monocyclic is preferably a 5- to 8-membered, and more preferably 5- or 6-membered ring. Examples thereof include "5-membered aromatic heterocyclyl" such as pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl, and "6-membered aromatic heterocyclyl" such as pyridyl, pyridazinyl, pyrimidinyl, pyrazinyl, and triazinyl and the like.

Examples of the aromatic heterocyclyl which is bicyclic include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, pyrazolopyridyl, imidazopyridyl, triazolopyridyl, imidazothiazolyl, pyrazinopyridazinyl, oxazolopyridyl, and thiazolopyridyl and the like.

Examples of the aromatic heterocyclyl which is polycyclic having three or more rings include carbazolyl, acridinyl, xanthenyl, phenothiazinyl, phenoxathiinyl, phenoxazinyl, and dibenzofuryl and the like.

"Non-aromatic heterocycle" means a cyclic non-aromatic ring, which is monocyclic or polycyclic having two or more rings, containing one or more identical or different heteroatoms selected independently from O, S and N in the ring.

The non-aromatic heterocycle which is polycyclic having two or more rings includes a fused ring wherein a non-aromatic heterocycle which is monocyclic or polycyclic having two or more rings is fused with a ring of the above "aromatic carbocycle", "non-aromatic carbocycle" and/or "aromatic heterocycle". The non-aromatic heterocycle which is polycyclic having two or more rings further includes a fused ring wherein an aromatic heterocycle which is monocyclic or polycyclic having two or more rings is fused with a ring of the above "non-aromatic carbocycle".

In addition, "non-aromatic heterocycle" includes a ring having a bridge or a spiro ring as follows:

[Chemical Formula 19]

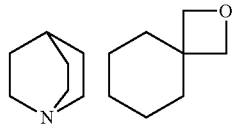

The non-aromatic heterocycle which is monocyclic is preferably a 3- to 8-membered, more preferably 3- to 6-membered, and more preferably 5- or 6-membered ring. Examples thereof include "5-membered non-aromatic heterocycle" such as thiazolidine, pyrrolidine, pyrroline, imidazolidine, imidazoline, pyrazolidine, pyrazoline, tetrahydrofuran, dihydrothiazole, tetrahydrothiazole, tetrahydroisothiazole, dioxolane, and dioxoline and the like, "6-membered non-aromatic heterocycle" such as dioxane, thiane, piperidine, piperazine, morpholine, thiomorpholine, dihydropyridine, tetrahydropyridine, tetrahydropyran, dihydrooxazine, tetrahydropyridazine, hexahydropyrimidine, and thiazine, and thiirane, oxirane, oxetane, oxathiolane, azetidine, hexahydroazepine, tetrahydrodiazepine, dioxazine, aziridine, oxepane, thiolane, and thiine and the like.

Examples of the non-aromatic heterocycle which is bicyclic include indoline, isoindoline, chromane, isochromane, dihydrobenzofuran, dihydroisobenzofuran, dihydroquinoline, dihydroisoquinoline, tetrahydroquinoline, and tetrahydroisoquinoline and the like.

"Non-aromatic heterocyclyl" means a cyclic non-aromatic cyclyl, which is monocyclic or polycyclic having two or more rings, containing one or more identical or different heteroatoms selected independently from O, S and N in the ring. The non-aromatic heterocyclyl which is polycyclic having two or more rings includes a fused ring wherein a non-aromatic heterocyclyl which is monocyclic or polycyclic having two or more rings is fused with a ring of the above "aromatic carbocyclyl", "non-aromatic carbocyclyl" and/or "aromatic heterocyclyl".

In addition, "non-aromatic heterocyclyl" includes a group having a bridge or a group to form a spiro ring as follows.

[Chemical Formula 20]

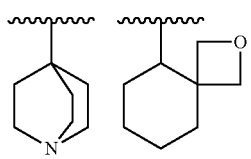

The non-aromatic heterocyclyl which is monocyclic is preferably a 3- to 8-membered, and more preferably 5- or 6-membered ring. Examples thereof include "5-membered non-aromatic heterocyclyl" such as thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydrothiazolyl, tetrahydroisothiazolyl, dioxolanyl, and dioxolinyl and the like, "6-membered non-aromatic heterocyclyl" such as dioxanyl, thianyl, piperidyl, piperazinyl, morpholinyl, morpholino, thiomorpholino, dihydropyridyl, tetrahydropyridyl, tetrahydropyranyl, dihydrooxazinyl, tetrahydropyridazinyl, hexahydropyrimidinyl, and thiazinyl, and thiiranyl, oxiranyl, oxetanyl, oxathiolanyl, azetidinyl, hexahydroazepinyl, tetrahydrodiazepinyl, dioxazinyl, aziridinyl, oxepanyl, thiolanyl, and thiinyl and the like.

Examples of the non-aromatic heterocyclyl which is bicyclic include indolinyl, isoindolinyl, chromanyl, isochromanyl, dihydrobenzofuryl, dihydroisobenzofuryl, dihydroquinolinyl, dihydroisoquinolinyl, tetrahydroquinolyl, and tetrahydroisoquinolinyl and the like.

"Hydroxy alkyl" means a group wherein hydrogen atom(s) bonded to carbon atom(s) of the above "alkyl" is replaced with one or more hydroxy groups. Examples thereof include hydroxymethyl, 1-hydroxyethyl, 2-hydroxyethyl, 1-hydroxypropyl, 2-hydroxypropyl, and 1,2-dihydroxyethyl and the like.

Examples of preferred embodiments of "hydroxyalkyl" include hydroxymethyl.

"Alkyloxy" means a group wherein the above "alkyl" is bonded to an oxygen atom. Examples thereof include methoxy, ethoxy, n-propyloxy, isopropyloxy, n-butyloxy, tert-butyloxy, isobutyloxy, sec-butyloxy, pentyloxy, isopentyloxy, and hexyloxy and the like.

Examples of preferred embodiments of "alkyloxy" include methoxy, ethoxy, n-propyloxy, isopropyloxy and tert-butyloxy.

"Alkenyloxy" means a group wherein the above "alkenyl" is bonded to an oxygen atom. Examples thereof include vinyloxy, allyloxy, 1-propenyloxy, 2-butenyloxy, 2-pentenyloxy, 2-hexenyloxy, 2-heptenyloxy, and 2-octenyloxy and the like.

"Alkynyloxy" means a group wherein the above "alkynyl" is bonded to an oxygen atom. Examples thereof include ethynyloxy, 1-propynyloxy, 2-propynyloxy, 2-butynyloxy, 2-pentynyloxy, 2-hexynyloxy, 2-heptynyloxy, and 2-octynyloxy and the like.

"Haloalkyl" means a group wherein one or more the above "halogen" is bonded to the above "alkyl". Examples thereof include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, and 1,1,1-trifluoropropan-2-yl and the like.

Examples of preferred embodiments of "haloalkyl" include difluoroethyl, trifluoromethyl, and trichloromethyl, particularly preferably difluoroethyl.

"Haloalkyloxy" means a group wherein the above "haloalkyl" is bonded to an oxygen atom. Examples thereof include monofluoromethoxy, monofluoroethoxy, trifluoromethoxy, trichloromethoxy, trifluoroethoxy, and trichloroethoxy and the like.

Examples of preferred embodiments of "haloalkyloxy" include trifluoromethoxy, and trichloromethoxy.

"Alkylcarbonyl" means a group wherein the above "alkyl" is bonded to a carbonyl group. Examples thereof include methylcarbonyl, ethylcarbonyl, propylcarbonyl, isopropylcarbonyl, tert-butylcarbonyl, isobutylcarbonyl, sec-butylcarbonyl, penthylcarbonyl, isopenthylcarbonyl, and hexylcarbonyl and the like.

Examples of preferred embodiments of "alkylcarbonyl" include methylcarbonyl, ethylcarbonyl, and n-propylcarbonyl.

"Alkenylcarbonyl" means a group wherein the above "alkenyl" is bonded to a carbonyl group. Examples thereof include ethylenylcarbonyl and propenylcarbonyl and the like.

"Alkynylcarbonyl" means a group wherein the above "alkynyl" is bonded to a carbonyl group. Examples thereof include ethynylcarbonyl and propynylcarbonyl and the like.

"Alkylamino" includes "monoalkylamino" and "dialkylamino".

"Monoalkylamino" means a group wherein one hydrogen atom bonded to a nitrogen atom of an amino group is replaced with the above "alkyl". Examples thereof include methylamino, ethylamino, and isopropylamino and the like.

Examples of preferred embodiments of "monoalkylamino" include methylamino and ethylamino.

"Dialkylamino" means a group wherein two hydrogen atoms bonded to a nitrogen atom of an amino group are replaced with two above "alkyl". These two alkyl groups may be the same or different. Examples thereof include dimethylamino, diethylamino, N,N-diisopropylamino, N-methyl-N-ethylamino, and N-isopropyl-N-ethylamino and the like.

Examples of preferred embodiments of "dialkylamino" include dimethylamino and diethylamino.

"Alkylsulfonyl" means a group wherein the above "alkyl" is bonded to a sulfonyl group. Examples thereof include methylsulfonyl, ethylsulfonyl, propylsulfonyl, isopropylsulfonyl, tert-butylsulfonyl, isobutylsulfonyl, and sec-butylsulfonyl and the like.

Examples of preferred embodiments of "alkylsulfonyl" include methylsulfonyl and ethylsulfonyl.

"Alkenylsulfonyl" means a group wherein the above "alkenyl" is bonded to a sulfonyl group. Examples thereof include ethylenylsulfonyl and propenylsulfonyl, and the like.

"Alkynylsulfonyl" means a group wherein the above "alkynyl" is bonded to a sulfonyl group. Examples thereof include ethynylsulfonyl and propynylsulfonyl and the like.

"Alkylcarbonylamino" includes "monoalkylcarbonylamino" and "dialkylcarbonylamino".

"Monoalkylcarbonylamino" means a group wherein one hydrogen atom bonded to a nitrogen atom of an amino group is replaced with the above "alkylcarbonyl". Examples thereof include methylcarbonylamino, ethylcarbonylamino, propylcarbonylamino, isopropylcarbonylamino, tert-butylcarbonylamino, isobutylcarbonylamino, and see-butylcarbonylamino and the like.

Examples of preferred embodiments of "monoalkylcarbonylamino" include methylcarbonylamino and ethylcarbonylamino.

"Dialkylarbonylamino" includes a group wherein two hydrogen atoms bonded to a nitrogen atom of an amino group are replaced with two above "alkylcarbonyl". These two alkylcarbonyl groups may be the same or different. Examples thereof include dimethylcarbonylamino, diethylcarbonylamino, and N,N-diisopropylcarbonylamino and the like.

Examples of preferred embodiments of "dialkylcarbonylamino" include dimethylcarbonylaminoanddiethylcarbonylamino.

"Alkylimino" means a group wherein a hydrogen atom bonded to a nitrogen atom of an imino group is replaced with the above "alkyl". Examples thereof include methylimino, ethylimino, n-propylimino, and isopropylimino and the like.

"Alkyloxyimino" means a group wherein a hydrogen atom bonded to a nitrogen atom of an imino group is replaced with the above "alkyloxy". Examples thereof include methyloxyimino, ethyloxyimino, n-propyloxyimino, and isopropyloxyimino and the like.

"Alkylsulfonylamino" includes "monoalkylsulfonylamino" and "dialkylsulfonylamino".

"Monoalkylsulfonylamino" means a group wherein one hydrogen atom bonded to a nitrogen atom of an amino group is replaced with the above "alkylsulfonyl".

Examples thereof include methylsulfonylamino, ethylsulfonylamino, propylsulfonylamino, isopropylsulfonylamino, tert-butylsulfonylamino, isobutylsulfonylamino and sec-butylsulfonylamino and the like.

Examples of preferred embodiments of "monoalkylsulfonylamino" include methylsulfonylamino and ethylsulfonylamino.

"Dialkylsulfonylamino" means a group wherein two hydrogen atoms attached to a nitrogen atom of an amino group are replaced with two above "alkylsulfonyl". These two alkylsulfonyl groups may be the same or different. Examples thereof include dimethylsulfonylamino, diethylsulfonylamino, and N,N-diisopropylsulfonylamino and the like.

Examples of preferred embodiments of "dialkylsulfonylamino" include dimethylsulfonylamino and diethylsulfonylamino.

"Alkylcarbonyloxy" means a group wherein the above "alkylcarbonyl" is bonded to an oxygen atom. Examples thereof include methylcarbonyloxy, ethylcarbonyloxy, propylcarbonyloxy, isopropylcarbonyloxy, tert-butylcarbonyloxy, isobutylcarbonyloxy, and sec-butylcarbonyloxy and the like.

Examples of preferred embodiments of "alkylcarbonyloxy" include methylcarbonyloxy and ethylcarbonyloxy.

"Alkenylcarbonyloxy" means a group wherein the above "alkenylcarbonyl" is bonded to an oxygen atom. Examples thereof include ethylenycarbonyloxy and propenylcarbonyloxy and the like.

"Alkynylcarbonyloxy" means a group wherein the above "alkynylcarbonyl" is bonded to an oxygen atom. Examples thereof include ethynylcarbonyloxy and propynylcarbonyloxy and the like.

"Alkyloxycarbonyl" means a group wherein the above "alkyloxy" is bonded to a carbonyl group. Examples thereof include methyloxycarbonyl, ethyloxycarbonyl, propyloxycarbonyl, isopropyloxycarbonyl, tert-butyloxycarbonyl, isobutyloxycarbonyl, sec-butyloxycarbonyl, penthyloxycarbonyl, isopenthyloxycarbonyl, and hexyloxycarbonyl and the like.

Examples of preferred embodiments of "alkyloxycarbonyl" include methyloxycarbonyl, ethyloxycarbonyl, and propyloxycarbonyl.

"Alkenyloxycarbonyl" means a group wherein the above "alkenyloxy" is bonded to a carbonyl group. Examples thereof include ethylenyloxycarbonyl and propenyloxycarbonyl and the like.

"Alkynyloxycarbonyl" means a group wherein the above "alkynyloxy" is bonded to a carbonyl group. Examples thereof include ethynyloxycarbonyl and propynyloxycarbonyl and the like.

"Alkylsulfanyl" means a group wherein a hydrogen atom bonded to a sulfur atom of a sulfanyl group is replaced with the above "alkyl". Examples thereof include methylsulfanyl, ethylsulfanyl, n-propylsulfanyl, and isopropylsulfanyl and the like.

"Alkenylsulfanyl" means a group wherein a hydrogen atom bonded to a sulfur atom of a sulfanyl group is replaced with the above "alkenyl". Examples thereof include ethylenylsulfanyl and propenylsulfanyl and the like.

"Alkynylsulfanyl" means a group wherein a hydrogen atom bonded to a sulfur atom of a sulfanyl group is replaced with the above "alkynyl". Examples thereof include ethynylsulfanyl and propynylsulfanyl and the like.

"Alkylsulfinyl" means a group wherein the above "alkyl" is bonded to a sulfinyl group. Examples thereof include methylsulfinyl, ethylsulfinyl, n-propylsulfinyl and isopropylsulfinyl and the like.

"Alkenylsulfinyl" means a group wherein the above "alkenyl" is bonded to a sulfinyl group. Examples thereof include ethylenylsulfinyl and propenylsulfinyl and the like.

"Alkynylsulfinyl" means a group wherein the above "alkynyl" is bonded to a sulfinyl group. Examples thereof include ethynylsulfinyl and propynylsulfinyl and the like.

"Alkylcarbamoyl" include "monoalkylcarbamoyl" and "dialkylcarbamoyl".

"Monoalkylcarbamoyl" means a group wherein one hydrogen atom bonded to a nitrogen atom of a carbamoyl group is replaced with the above "alkyl". Examples thereof include methylcarbamoyl and ethylcarbamoyl and the like.

"Dialkylcarbamoyl" means a group wherein two hydrogen atoms bonded to a nitrogen atom of a carbamoyl group are replaced with two above "alkyl". These two alkyl groups may be the same or different. Examples thereof include dimethylcarbamoyl, and diethylcarbamoyl and the like.

"Alkylsulfamoyl" includes "monoalkylsulfamoyl" and "dialkylsulfamoyl".

"Monoalkylsulfamoyl" means a group wherein one hydrogen atom bonded to a nitrogen atom of a sulfamoyl group is replaced with the above "alkyl". Examples thereof include methylsulfamoyl and dimethylsulfamoyl and the like.

"Dialkylsulfamoyl" means a group wherein two hydrogen atoms bonded to a nitrogen atom of a sulfamoyl group are replaced with two above "alkyl". These two alkyl groups may be the same or different. Examples thereof include dimethylsulfamoyl and diethylsulfamoyl and the like.

The alkyl portion of "aromatic carbocyclylalkyl", "non-aromatic carbocyclylalkyl", "aromatic heterocyclylalkyl", and "non-aromatic heterocyclylalkyl" means the same as above "alkyl".

"Aromatic carbocyclylalkyl" means alkyl substituted with one or more the above "aromatic carbocyclyl". Examples thereof include benzyl, phenethyl, phenylpropyl, benzhydryl, trityl, naphthylmethyl, and a group shown below:

[Chemical Formula 21]

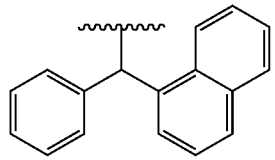

and the like.

Examples of preferred embodiments of "aromatic carbocyclylalkyl" include benzyl, phenethyl, and benzhydryl.

"Non-aromatic carbocyclylalkyl" means alkyl substituted with one or more the above "non-aromatic carbocyclyl". Also, "non-aromatic carbocyclylalkyl" includes "non-aromatic carbocyclylalkyl" wherein the alkyl portion thereof is substituted with one or more the above "aromatic carbocyclyl". Examples thereof include cyclopropylmethyl, cyclobutylmethyl, cyclopentylmethyl, cyclohexylmethyl, and a group shown below:

[Chemical Formula 22]

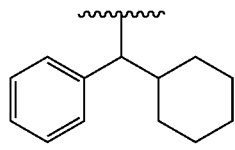

and the like.

"Aromatic heterocyclylalkyl" means alkyl substituted with one or more the above "aromatic heterocyclyl". Also, "aromatic heterocyclylalkyl" includes "aromatic heterocyclylalkyl" wherein the alkyl portion thereof is substituted with one or more the above "aromatic carbocyclyl" and/or "non-aromatic carbocyclyl". Examples thereof include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, and a group shown below:

[Chemical Formula 23]

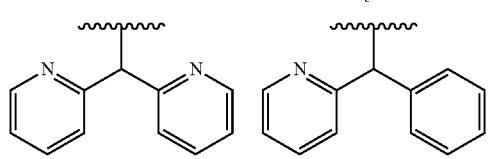

-continued

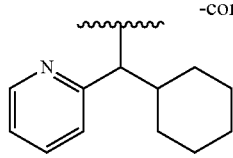

and the like.

"Non-aromatic heterocyclylalkyl" means alkyl substituted with one or more the above "non-aromatic heterocyclyl". Also, "non-aromatic heterocyclylalkyl" includes a "non-aromatic heterocyclylalkyl" wherein the alkyl portion thereof is substituted with above "aromatic carbocyclyl", "non-aromatic carbocyclyl" and/or "aromatic heterocyclyl". Examples thereof include tetrahydropyranylmethyl, morpholinyethyl, piperidinylmethyl, piperazinylmethyl, and a group shown below:

[Chemical Formula 24]

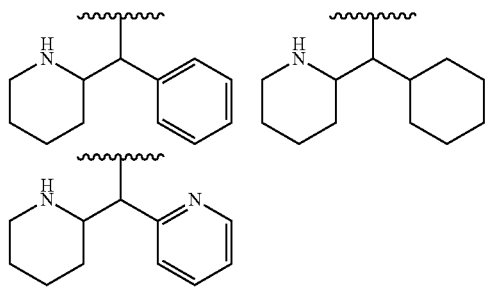

and the like.

The "aromatic carbocycle" portion of "aromatic carbocyclyloxy", "aromatic carbocyclylamino", "aromatic carbocyclylsulfanyl", "aromatic carbocyclyearbonyl", "aromatic carbocyclylsulfonyl", "aromatic carbocyclylcarbonyloxy", "aromatic carbocyclylsulfonyloxy", "aromatic carbocyclyloxycarbonyl", "aromatic carbocyclyloxysulfonyl", "aromatic carbocyclylcarbamoyl", "aromatic carbocyclylsulfamoyl", "aromatic carbocyclylcarbonylamino", "aromatic carbocyclylsulfonylamino", and "aromatic carbocyclyloxycarbonylamino" is the same as above "aromatic carbocyclyl".

"Aromatic carbocyclyloxy" means a group wherein "aromatic carbocycle" is bonded to an oxygen atom. Examples thereof include phenyloxy and naphthyloxy and the like.

"Aromatic carbocyclylamino" means a group wherein a hydrogen atom attached to a nitrogen atom of an amino group is replaced with "aromatic carbocycle". Examples thereof include phenylamino and naphthylamino and the like. Another hydrogen atom bonded to the nitrogen atom of the amino group may be replaced with the above "alkyl".

"Aromatic carbocyclylsulfanyl" means a group wherein a hydrogen atom bonded to a sulfur atom of a sulfanyl group is replaced with "aromatic carbocycle". Examples thereof include phenylsulfanyl and naphthylsulfanyl and the like.

"Aromatic carbocyclylearbonyl" means a group wherein "aromatic carbocycle" is bonded to a carbonyl group. Examples thereof include phenylcarbonyl and naphthylcarbonyl and the like.

"Aromatic carbocyclylsulfonyl" means a group wherein "aromatic carbocycle" is bonded to a sulfonyl group. Examples thereof include phenylsulfonyl and naphthylsulfonyl and the like.

The "non-aromatic carbocycle" portion of "non-aromatic carbocyclyloxy", "non-aromatic carbocyclylamino", "non-aromatic carbocyclylsulfanyl", "non-aromatic carbocyclylcarbonyl", and "non-aromatic carbocyclylsulfonyl" means the same as above "non-aromatic carbocyclyl".

"Non-aromatic carbocyclyloxy" means a group wherein "non-aromatic carbocycle" is bonded to an oxygen atom. Examples thereof include cyclopropyloxy, cyclohexyloxy, and cyclohexenyloxy.

"Non-aromatic carbocyclylamino" means a group wherein a hydrogen atom attached to a nitrogen atom of an amino group is replaced with "non-aromatic carbocycle". Examples thereof include cyclopropylamino, cyclohexylamino, and cyclohexenylamino and the like. Another hydrogen atom bonded to the nitrogen atom of the amino group may be replaced with the above "alkyl".

"Non-aromatic carbocyclylsulfanyl" means a group wherein a hydrogen atom bonded to a sulfur atom of a sulfanyl group is replaced with "non-aromatic carbocycle". Examples thereof include cyclopropylsulfanyl, cyclohexylsulfanyl, and cyclohexenylsulfanyl and the like.

"Non-aromatic carbocyclylcarbonyl" means a group wherein "non-aromatic carbocycle" is bonded to a carbonyl group. Examples thereof include cyclopropylcarbonyl, cyclohexylcarbonyl, and cyclohexenylcarbonyl and the like.

"Non-aromatic carbocyclylsulfonyl" means a group wherein "non-aromatic carbocycle" is bonded to a sulfonyl group. Examples thereof include cyclopropylsulfonyl, cyclohexylsulfonyl, and cyclohexenylsulfonyl and the like.

The "aromatic heterocycle" portion of "aromatic heterocyclyloxy", "aromatic heterocyclylamino", "aromatic heterocyclylsulfanyl", "aromatic heterocyclylcarbonyl", and "aromatic heterocyclylsulfonyl" means the same as above "aromatic heterocyclyl".

"Aromatic heterocyclyloxy" means a group wherein "aromatic heterocycle" is bonded to an oxygen atom. Examples thereof include pyridyloxy and oxazolyloxy and the like.

"Aromatic heterocyclylamino" means a group wherein a hydrogen atom attached to a nitrogen atom of an amino group is replaced with "aromatic heterocycle". Examples thereof include pyridylamino and oxazolylamino. Another hydrogen atom bonded to the nitrogen atom of the amino group may be replaced with the above "alkyl".

"Aromatic heterocyclylsulfanyl" means a group wherein a hydrogen atom bonded to a sulfur atom of a sulfanyl group is replaced with "aromatic heterocycle". Examples thereof include pyridylsulfanyl and oxazolylsulfanyl and the like.

"Aromatic heterocyclylcarbonyl" means a group wherein "aromatic heterocycle" is bonded to a carbonyl group. Examples thereof include pyridylcarbonyl and oxazolylcarbonyl and the like.

"Aromatic heterocyclylsulfonyl" means a group wherein "aromatic heterocycle" is bonded to a sulfonyl group. Examples thereof include pyridylsulfonyl and oxazolylsulfonyl and the like.

The "non-aromatic heterocycle" portion of "non-aromatic heterocyclyloxy", "non-aromatic heterocyclylamino", "non-aromatic heterocyclylsulfanyl", "non-aromatic heterocyclylcarbonyl", and "non-aromatic heterocyclylsulfonyl" means the same as above "non-aromatic heterocyclyl".

"Non-aromatic heterocyclyloxy" means a group wherein "non-aromatic heterocycle" is bonded to an oxygen atom. Examples thereof include piperidinyloxy and tetrahydrofuryloxy and the like.

"Non-aromatic heterocyclylamino" means a group wherein a hydrogen atom attached to a nitrogen atom of an amino group is replaced with the "non-aromatic heterocycle". Examples thereof include piperidinylamino and tetrahydrofurylamino and the like. Another hydrogen atom bonded to the nitrogen atom of the amino group may be replaced with the above "alkyl".

"Non-aromatic heterocyclylsulfanyl" means a group wherein a hydrogen atom bonded to a sulfur atom of a sulfanyl group is replaced with "non-aromatic heterocycle". Examples thereof include piperidinylsulfanyl and tetrahydrofurylsulfanyl and the like.

"Non-aromatic heterocyclylcarbonyl" means a group wherein "non-aromatic heterocycle" is bonded to a carbonyl group. Examples thereof include piperidinylcarbonyl and tetrahydrofurylcarbonyl and the like.

"Non-aromatic heterocyclylsulfonyl" means a group wherein "non-aromatic heterocycle" is bonded to a sulfonyl group. Examples thereof include piperidinylsulfonyl and tetrahydrofurylsulfonyl and the like.

"Substituted or unsubstituted non-aromatic carbocyclyl" and "substituted or unsubstituted non-aromatic heterocyclyl" may be substituted with "oxo". When substituted with "oxo", it means a group wherein two hydrogen atoms on a carbon atom are replaced as follows:

[Chemical Formula 25]

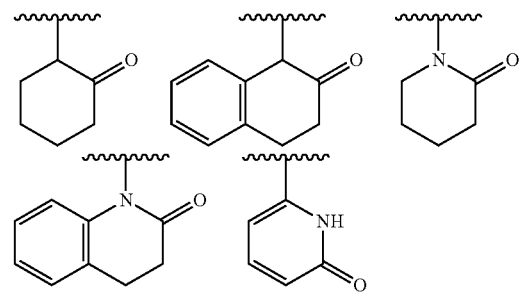

Non-aromatic carbocycle and non-aromatic heterocycle portions of the above "substituted or unsubstituted non-aromatic carbocyclyloxy", "substituted or unsubstituted non-aromatic carbocyclylamino", "substituted or unsubstituted non-aromatic carbocyclylsulfanyl", "substituted or unsubstituted non-aromatic carbocyclylcarbonyl", "substituted or unsubstituted non-aromatic carbocyclylsulfonyl", "substituted or unsubstituted non-aromatic heterocyclyloxy, "substituted or unsubstituted non-aromatic heterocyclylamino", "substituted or unsubstituted non-aromatic heterocyclylsulfanyl", "substituted or unsubstituted non-aromatic heterocyclylcarbonyl", and "substituted or unsubstituted non-aromatic heterocyclylsulfonyl" may be substituted with "oxo" similarly as described above.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", and "substituted or unsubstituted alkynylsulfonyl" include the following substituent group C1, and preferably the substituent group C2. They can be substituted with one or more substituents selected from the group.

Substituent group C1: halogen, hydroxy, carboxy, amino, carbamoyl, sulfamoyl, cyano, nitro, ureido, amidino, guanidino, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkylimino optionally substituted with one or more group(s) selected from the substituent group A, alkyloxyimino optionally substituted with one or more group(s) selected from the substituent group A, alkylcarbonyl optionally substituted with one or more group(s) selected from the substituent group A, alkylsulfonyl optionally substituted with one or more group(s) selected from the substituent group A, alkylcarbonylamino optionally substituted with one or more group(s) selected from the substituent group A, alkylsulfonylamino optionally substituted with one or more group(s) selected from the substituent group A, alkylcarbamoyl optionally substituted with one or more group(s) selected from the substituent group A, alkylsulfamoyl optionally substituted with one or more group(s) selected from the substituent group A, aromatic carbocyclyl optionally substituted with one or more group(s) selected from the substituent group B1, non-aromatic carbocyclyl optionally substituted with one or more group(s) selected from the substituent group B1', aromatic heterocyclyl optionally substituted with one or more group(s) selected from the substituent group B1, non-aromatic heterocyclyl optionally substituted with one or more group(s) selected from the substituent group B1', aromatic carbocyclyloxy optionally substituted with one or more group(s) selected from the substituent group B1, non-aromatic carbocyclyloxy optionally substituted with one or more group(s) selected from the substituent group B1', aromatic heterocyclyloxy optionally substituted with one or more group(s) selected from the substituent group B1, non-aromatic heterocyclyloxy optionally substituted with one or more group(s) selected from the substituent group B1', aromatic carbocyclylsulfanyl optionally substituted with one or more group(s) selected from the substituent group B1, non-aromatic carbocyclylsulfanyl optionally substituted with one or more group(s) selected from the substituent group B1', aromatic heterocyclylsulfanyl optionally substituted with one or more group(s) selected from the substituent group B1, non-aromatic heterocyclylsulfanyl optionally substituted with one or more group(s) selected from the substituent group B1', aromatic carbocyclylamino optionally substituted with one or more group(s) selected from the substituent group B1, non-aromatic carbocyclylamino optionally substituted with one or more group(s) selected from the substituent group B1', aromatic heterocyclylamino optionally substituted with one or more group(s) selected from the substituent group B1, and non-aromatic heterocyclylamino optionally substituted with one or more group(s) selected from the substituent group B1', aromatic carbocyclylcarbonyl optionally substituted with one or more group(s) selected from the substituent group B1, non-aromatic carbocyclylcarbonyl optionally substituted with one or more group(s) selected from the substituent group B1', aromatic heterocyclylcarbonyl optionally substituted with one or more group(s) selected from the substituent group B1, non-aromatic heterocyclylcarbonyl optionally substituted with one or more group(s) selected from the substituent group B1', aromatic carbocyclylsulfonyl optionally substituted with one or more group(s) selected from the substituent group B1, non-aromatic carbocyclylsulfonyl optionally substituted with one or more group(s) selected from the substituent group B1', aromatic heterocyclylsulfonyl optionally substituted with one or more group(s) selected from the substituent group B1, and non-aromatic heterocyclylsulfonyl optionally substituted with one or more group(s) selected from the substituent group B1'.

Substituent group A: halogen, hydroxy, carboxy, amino, carbamoyl, sulfamoyl, cyano, and nitro.

Examples of preferred embodiments of the substituent group A include halogen and hydroxy.

Examples of more preferred embodiments of the substituent group A include halogen.

Substituent group B1: halogen, hydroxy, carboxy, amino, carbamoyl, sulfamoyl, cyano, nitro, ureido, amidino, guanidino, alkyl optionally substituted with one or more group(s) selected from the substituent group A, alkenyl optionally substituted with one or more group(s) selected from the substituent group A alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkylcarbonyl optionally substituted with one or more group(s) selected from the substituent group A, alkenylcarbonyl optionally substituted with one or more group(s) selected from the substituent group A, alkynylcarbonyl optionally substituted with one or more group(s) selected from the substituent group A, alkylsulfonyl optionally substituted with one or more group(s) selected from the substituent group A, alkenylsulfonyl optionally substituted with one or more group(s) selected from the substituent group A, alkynylsulfonyl optionally substituted with one or more group(s) selected from the substituent group A, alkylcarbonylamino optionally substituted with one or more group(s) selected from the substituent group A, alkylsulfonylamino optionally substituted with one or more group(s) selected from the substituent group A, alkylcarbamoyl optionally substituted with one or more group(s) selected from the substituent group A, alkylsulfamoyl optionally substituted with one or more group(s) selected from the substituent group A, alkylcarbonyloxy optionally substituted with one or more group(s) selected from the substituent group A, alkyloxycarbonyl optionally substituted with one or more group(s) selected from the substituent group A, alkylsulfonyloxy optionally substituted with one or more group(s) selected from the substituent group A, alkyloxysulfonyl optionally substituted with one or more group(s) selected from the substituent group A; and aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylcarbonyl, non-aromatic carbocyclylcarbonyl, aromatic heterocyclylcarbonyl, non-aromatic heterocyclylcarbonyl, aromatic carbocyclylsulfonyl, non-aromatic carbocyclylsulfonyl, aromatic heterocyclylsulfonyl, and non-aromatic heterocyclylsulfonyl (each aromatic carbocycle, non-aromatic carbocycle, aromatic heterocycle and non-aromatic heterocycle may be substituted with one or more groups selected from halogen, alkyl, hydroxy and alkyloxy).

Substituent group B1': oxo, halogen, hydroxy, carboxy, amino, carbamoyl, sulfamoyl, cyano, nitro, ureido, amidino, guanidino, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, alkylamino optionally substituted with one or more group(s) selected from the substituent group A, alkenylamino optionally substituted with one or more group(s) selected from the substituent group A, alkynylamino optionally substituted with one or more group(s) selected from the substituent group A, alkylsulfanyl optionally substituted with one or more group(s) selected from the substituent group A, alkenylsulfanyl optionally substituted with one or more group(s) selected from the substituent group A, alkynylsulfanyl optionally substituted with one or more group(s) selected from the substituent group A, alkylcarbonyl optionally substituted with one or more group(s) selected from the substituent group A, alkenylcarbonyl optionally substituted with one or more group(s) selected from the substituent group A, alkynylcarbonyl optionally substituted with one or more group(s) selected from the substituent group A, alkylsulfonyl optionally substituted with one or more group(s) selected from the substituent group A, alkenylsulfonyl optionally substituted with one or more group(s) selected from the substituent group A, alkynylsulfonyl optionally substituted with one or more group(s) selected from the substituent group A, alkylcarbonylamino optionally substituted with one or more group(s) selected from the substituent group A, alkylsulfonylamino optionally substituted with one or more group(s) selected from the substituent group A, alkylcarbamoyl optionally substituted with one or more group(s) selected from the substituent group A, alkylsulfamoyl optionally substituted with one or more group(s) selected from the substituent group A, alkylcarbonyloxy optionally substituted with one or more group(s) selected from the substituent group A, alkyloxycarbonyl optionally substituted with one or more group(s) selected from the substituent group A, alkylsulfonyloxy optionally substituted with one or more group(s) selected from the substituent group A, alkyloxysulfonyl optionally substituted with one or more group(s) selected from the substituent group A; and aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylcarbonyl, non-aromatic carbocyclylcarbonyl, aromatic heterocyclylcarbonyl, non-aromatic heterocyclylcarbonyl, aromatic carbocyclylsulfonyl, non-aromatic carbocyclylsulfonyl, aromatic heterocyclylsulfonyl, and non-aromatic heterocyclylsulfonyl (each aromatic carbocycle, non-aromatic carbocycle, aromatic heterocycle and non-aromatic heterocycle may be substituted with one or more groups selected from halogen, alkyl, hydroxy and alkyloxy).

Substituent group C2: halogen, hydroxy, cyano, alkyloxy optionally substituted with one or more group(s) selected from the substituent group A, alkenyloxy optionally substituted with one or more group(s) selected from the substituent group A, alkynyloxy optionally substituted with one or more group(s) selected from the substituent group A, aromatic carbocyclyl optionally substituted with one or more group(s) selected from the substituent group B2, non-aromatic carbocycyl optionally substituted with one or more group(s) selected from the substituent group B2', aromatic heterocyclyl optionally substituted with one or more group(s) selected from the substituent group B2, non-aromatic heterocyclyl optionally substituted with one or more group(s) selected from the substituent group B2', aromatic carbocyclyloxy optionally substituted with one or more group(s) selected from the substituent group B2, non-aromatic carbocyclyloxy optionally substituted with one or more group(s) selected from the substituent group B2', aromatic heterocyclyloxy optionally substituted with one or more group(s) selected from the substituent group B2, and non-aromatic heterocyclyloxy optionally substituted with one or more group(s) selected from the substituent group B2'.

Substituent group B2: halogen, hydroxy, cyano, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, and alkynyloxy optionally substituted with one or more group(s) selected from the substituent group A.

Substituent group B2': oxo, halogen, hydroxy, cyano, alkyl optionally substituted with one or more group(s) selected from the substituent group A, alkenyl optionally substituted with one or more group(s) selected from the substituent group A, alkynyl optionally substituted with one or more group(s) selected from the substituent group A, alkyloxy optionally substituted with one or more group(s) selected from the substituent group A, alkenyloxy optionally substituted with one or more group(s) selected from the substituent group A, and alkynyloxy optionally substituted with one or more group(s) selected from the substituent group A.

Examples of the substituents on the ring of "aromatic carbocycle" and "aromatic heterocycle" in the "substituted or unsubstituted aromatic carbocyclyl", "substituted or unsubstituted aromatic heterocyclyl", "substituted or unsubstituted aromatic carbocyclyloxy", "substituted or unsubstituted aromatic heterocyclyloxy", "substituted or unsubstituted aromatic carbocyclylamino", "substituted or unsubstituted aromatic heterocyclylamino", "substituted or unsubstituted aromatic carbocyclylsulfanyl", "substituted or unsubstituted aromatic heterocyclylsulfanyl", "substituted or unsubstituted aromatic carbocyclylcarbonyl", "substituted or unsubstituted aromatic heterocyclylcarbonyl", "substituted or unsubstituted aromatic carbocyclylsulfonyl", and "substituted or unsubstituted aromatic heterocyclylsulfonyl" include the substituent group B1, and preferably the substituent group B2. They can be substituted with one or more substituents selected from the group.

Examples of the substituents on the ring of "non-aromatic carbocycle" and "non-aromatic heterocycle" in the "substituted or unsubstituted non-aromatic carbocyclyl", "substituted or unsubstituted non-aromatic heterocyclyl", "substituted or unsubstituted non-aromatic carbocyclyloxy", "substituted or unsubstituted non-aromatic heterocyclyloxy", "substituted or unsubstituted non-aromatic carbocyclylamino", "substituted or unsubstituted non-aromatic heterocyclylamino", "substituted or unsubstituted non-aromatic carbocyclylsulfanyl", "substituted or unsubstituted non-aromatic heterocyclylsulfanyl", "substituted or unsubstituted non-aromatic carbocyclylcarbonyl", "substituted or unsubstituted non-aromatic heterocyclylcarbonyl", "substituted or unsubstituted non-aromatic carbocyclylsulfonyl", and "substituted or unsubstituted non-aromatic heterocyclylsulfonyl" include the substituent group B1', and preferably the substituent group B2'. They can be substituted with one or more substituents selected from the group.

Examples of preferred substituents of "substituted or unsubstituted aromatic heterocyclyl" and "substituted or unsubstituted aromatic carbocyclyl" in $R^{1a}$ to $R^{1c}$ include the substituent group α, more preferably the substituent group γ, particularly preferably haloalkyl. They can be substituted with one or more substituents selected from the group.

Substituent group α:
halogen;
alkyl optionally substituted with one or more group(s) selected from (non-aromatic carbocyclyl optionally substituted with one or more group(s) selected from the substituent group β1, and halogen);
alkenyl optionally substituted with one or more group(s) selected from (non-aromatic carbocyclyl optionally substituted with one or more group(s) selected from the substituent group β1, and halogen);
alkylcarbonyl optionally substituted with one or more group(s) selected from (non-aromatic carbocyclyl optionally substituted with one or more group(s) selected from the substituent group β1, and halogen);
alkenylcarbonyl optionally substituted with one or more group(s) selected from (non-aromatic carbocyclyl optionally substituted with one or more group(s) selected from the substituent group β1, and halogen);
aromatic carbocyclyl optionally substituted with one or more group(s) selected from the substituent group β1;
aromatic heterocyclyl optionally substituted with one or more group(s) selected from the substituent group β1;
non-aromatic carbocyclyl optionally substituted with one or more group(s) selected from the substituent group β1; and
non-aromatic heterocyclyl optionally substituted with one or more group(s) selected from the substituent group β1.

Substituent group β1: halogen, alkyl, haloalkyl, alkyloxy, and haloalkyloxy.

Substituent group γ:
halogen, alkyl, haloalkyl, alkylcarbonyl optionally substituted with one or more halogen; aromatic carbocyclyl optionally substituted with one or more halogen; and non-aromatic carbocyclyl optionally substituted with one or more halogen.

Examples of preferred substituents of "substituted or unsubstituted alkyl" and "substituted or unsubstituted alkyloxy" in $R^{2a}$ to $R^{2d}$, $R^3$, $R^{5a}$, $R^{5b}$, $R^{7a}$, $R^{7b}$ and $R^9$ include halogen and hydroxy, more preferably halogen.

Examples of preferred substituents of "substituted or unsubstituted alkyl" in $R^4$ include the substituent group C2, more preferably (halogen; aromatic heterocyclyl optionally substituted with one or more group(s) selected from the substituent group β1; non-aromatic heterocyclyl optionally substituted with one or more group(s) selected from the substituent group β2; aromatic heterocyclyloxy optionally substituted with one or more group(s) selected from the substituent group β1; and non-aromatic heterocyclyloxy optionally substituted with one or more group(s) selected from the substituent group β2). They can be substituted with one or more substituents selected from the group.

Substituent group β2: oxo, halogen, alkyl, haloalkyl, alkyloxy, and haloalkyloxy.

Examples of preferred substituents of "substituted or unsubstituted alkenyl" and "substituted or unsubstituted alkynyl" in $R^4$ include the substituent group C2, more preferably (aromatic heterocyclyl optionally substituted with one or more group(s) selected from the substituent group β; and non-aromatic heterocyclyl optionally substituted with one or more group(s) selected from the substituent group β and oxy). They can be substituted with one or more substituents selected from the group.

Examples of preferred substituents on the ring of "substituted or unsubstituted aromatic carbocyclyl" and "substituted or unsubstituted aromatic heterocyclyl" in $R^4$ and $R^3$ include halogen, alkyl, alkyloxy, haloalkyl, and haloalkyloxy, for example, the substituent group β1. They can be substituted with one or more substituents selected from the group.

Examples of preferred substituents on the ring of "substituted or unsubstituted non-aromatic heterocyclyl" and "substituted or unsubstituted non-aromatic carbocyclyl" in $R^4$ and $R^8$ include oxo, halogen, alkyl, alkyloxy, haloalkyl, and haloalkyloxy, for example, the substituent group β2. They can be substituted with one or more substituents selected from the group.

Examples of preferred substituents on the ring of "substituted or unsubstituted aromatic carbocyclyl", "substituted or unsubstituted aromatic heterocyclyl", "substituted or unsubstituted aromatic carbocyclyloxy" and "substituted or unsubstituted aromatic heterocyclyloxy" in $R^6$ include halogen, alkyl, alkyloxy, haloalkyl, and haloalkyloxy, for example, the substituent group β1. They can be substituted with one or more substituents selected from the group.

Examples of preferred substituents on the ring of "substituted or unsubstituted non-aromatic carbocyclyl", "substituted or unsubstituted non-aromatic heterocyclyl", "substituted or unsubstituted non-aromatic carbocyclyloxy" and "substituted or unsubstituted non-aromatic heterocyclyloxy" in $R^6$ include oxo, halogen, alkyl, alkyloxy, haloalkyl, and haloalkyloxy, and more preferably, for example, the substituent group β2. They can be substituted with one or more substituents selected from the group.

Examples of preferred substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", and "substituted or unsubstituted alkynylsulfonyl" in $R^{11a}$ and $R^{11b}$ include non-aromatic carbocyclyl optionally substituted with one or more group(s) selected from the substituent group β1, and halogen, more preferably halogen. They can be substituted with one or more substituents selected from the group.

Examples of preferred substituents of "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", "substituted or unsubstituted non-aromatic heterocyclyloxy", "substituted or unsubstituted aromatic carbocyclylcarbonyl", "substituted or unsubstituted non-aromatic carbocyclylcarbonyl", "substituted or unsubstituted aromatic heterocyclylcarbonyl", "substituted or unsubstituted non-aromatic heterocyclylcarbonyl", "substituted or unsubstituted aromatic carbocyclylsulfonyl", "substituted or unsubstituted non-aromatic carbocyclylsulfonyl", "substituted or unsubstituted aromatic heterocyclylsulfonyl" and "substituted or unsubstituted non-aromatic heterocyclylsulfonyl" in $R^{11a}$ and $R^{11b}$ include the substituent group β1, preferably halogen.

In a group represented by:

[Chemical Formula 26]

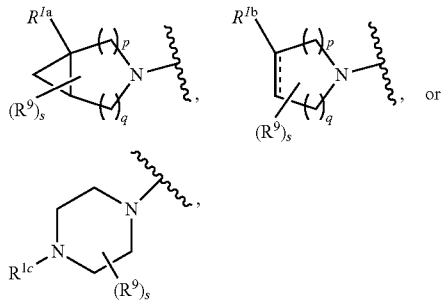

or

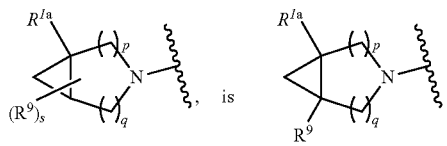

any ring-constituting atom, to which a substituent can attach, may be substituted with substituent $R^9$. Examples include the following:

[Chemical Formula 27]

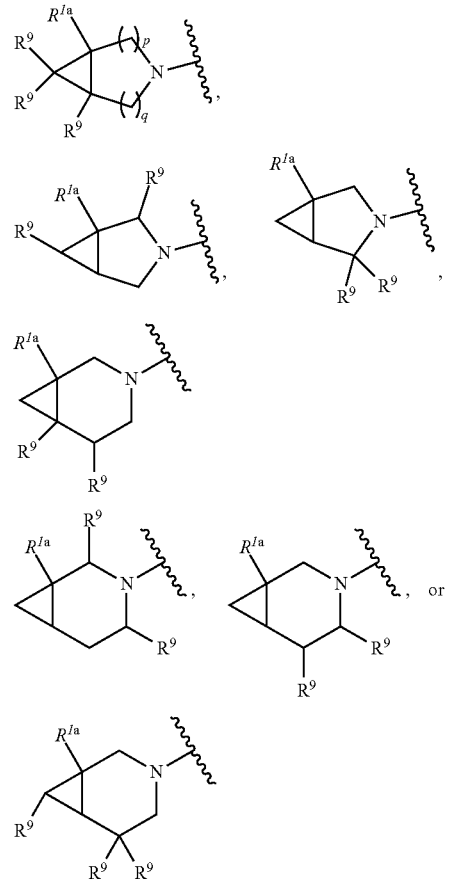

and the like.

In a group represented by:

[Chemical Formula 28]

any ring-constituting atom, to which a substituent can attach, may be substituted with substitutent $R^9$. Examples include the following:

[Chemical Formula 29]

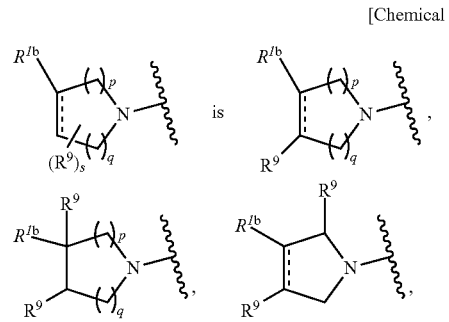

-continued

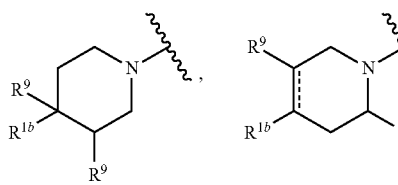

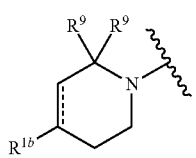

and the like.

In a group represented by:

[Chemical Formula 30]

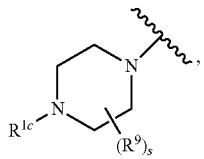

any ring-constituting atom, to which a substituent can attach, may be substituted with substituent $R^9$. Examples include the following:

[Chemical Formula 31]

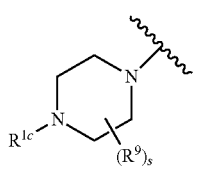, 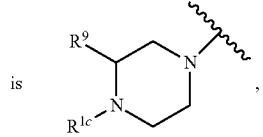,

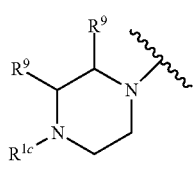 or 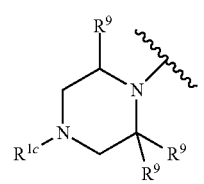

and the like.

When "two $R^9$s attached to different ring-constituting atoms may be taken together to form a substituted or unsubstituted (C1-C3) bridge wherein one of carbon atoms constituting the (C1-C3) bridge may be replaced with an oxygen atom or a nitrogen atom", a hydrogen atom or alkyl may be attached to the nitrogen atom, and the carbon atoms constituting the (C1-C3) bridge can be substituted with alkyl or halogen. Examples include the following:

[Chemical Formula 32]

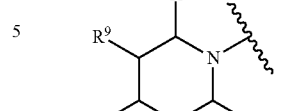 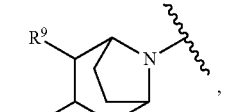,

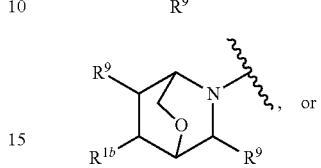 or 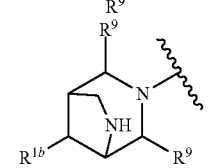

and the like.
Examples include the following:

[Chemical Formula 33]

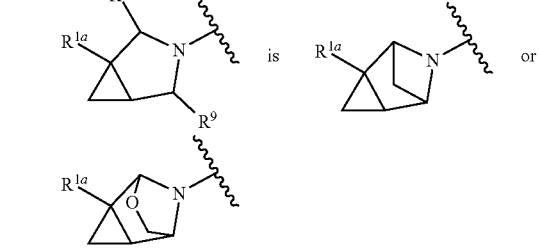

and the like.
Examples include the following:

[Chemical Formula 34]

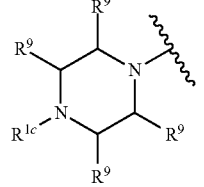 is 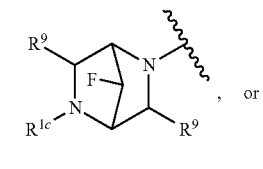, or

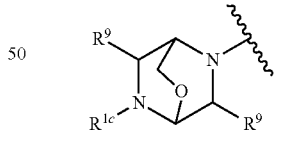

and the like.

In a group represented by:

[Chemical Formula 35]

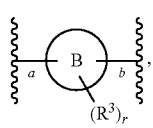

any ring-constituting atom, to which a substituent can attach, may be substituted with substituent $R^3$. For example, when (hereinafter referred to as "cyclyl A") is:

[Chemical Formula 36]

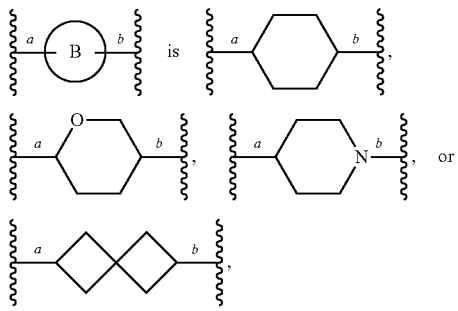

[Chemical Formula 39]

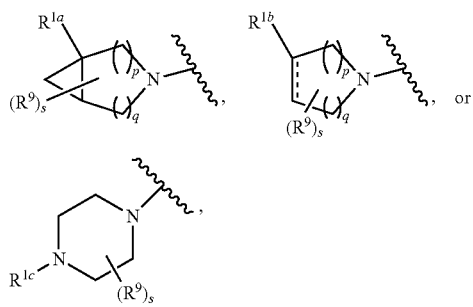

wherein p and q are each independently 1 or 2 (hereinafter referred to as "cyclyl A is A1").

Cyclyl A is:

any ring-constituting atom, to which a substituent can attach, may be substituted with substituent R³.

When "two R³s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom", a hydrogen atom or alkyl may be attached to the nitrogen atom, and the carbon atoms constituting the (C1-C3) bridge can be substituted with alkyl or halogen. Examples include the following:

[Chemical Formula 40]

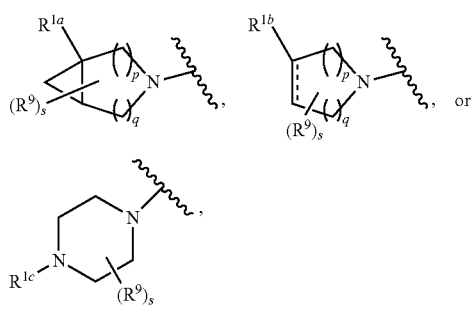

[Chemical Formula 37]

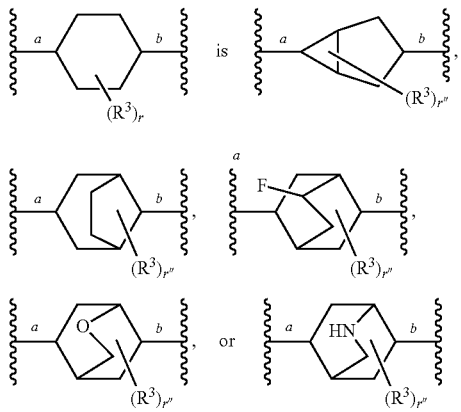

wherein p and q are each independently 1 or 2, provided that p and q are not simultaneously 2 (hereinafter referred to as "cyclyl A is A2").

Cyclyl A is:

[Chemical Formula 41]

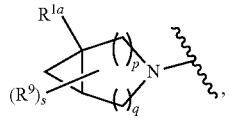

wherein r" is an integer of 0 to 2, and R³ is the same as defined above, and the like.

Specific examples of each substituent in the compound represented by Formula (I) or a pharmaceutically acceptable salt thereof are shown below. All possible combination of these specific examples are examples of the compound represented by Formula (I).

The group represented by:

wherein p and q are the same as defined in A2 (hereinafter referred to as "cyclyl A is A3").

Cyclyl A is:

[Chemical Formula 42]

[Chemical Formula 38]

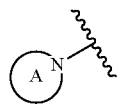

wherein p and q are the same as defined in A2 (hereinafter referred to as "cyclyl A is A4").

Cyclyl A is:

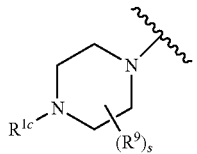

[Chemical Formula 43]

(hereinafter referred to as "cyclyl A is A5").

Cyclyl A is:

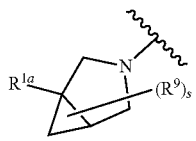

[Chemical Formula 44]

(hereinafter referred to as "cyclyl A is A6").

Cyclyl A is:

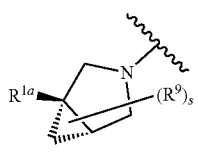

[Chemical Formula 45]

(hereinafter referred to as "cyclyl A is A7").

Cyclyl A is:

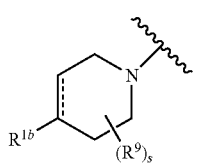

[Chemical Formula 46]

(hereinafter referred to as "cyclyl A is A8").

Cyclyl A is:

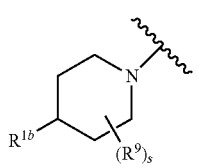

[Chemical Formula 47]

(hereinafter referred to as "cyclyl A is A9").

Cyclyl A is:

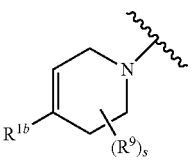

[Chemical Formula 48]

(hereinafter referred to as "cyclyl A is A10").

$R^{1a}$ to $R^{1c}$ are each independently substituted or unsubstituted aromatic heterocyclyl, substituted or unsubstituted aromatic carbocyclyl, substituted or unsubstituted non-aromatic heterocyclyl, or substituted or unsubstituted non-aromatic carbocyclyl (hereinafter referred to as "$R^{1a}$ to $R^{1c}$ are R11").

$R^{1a}$ to $R^{1c}$ are each independently substituted or unsubstituted aromatic heterocyclyl, or substituted or unsubstituted aromatic carbocyclyl (hereinafter referred to as "$R^{1a}$ to $R^{1c}$ are R12").

$R^{1a}$ is substituted or unsubstituted aromatic heterocyclyl or substituted or unsubstituted aromatic carbocyclyl; $R^{1b}$ is substituted or unsubstituted 5- to 6-membered aromatic heterocyclyl; Re is substituted or unsubstituted 5-membered aromatic heterocyclyl (hereinafter referred to as "$R^{1a}$ to $R^{1c}$ are R14").

$R^{1a}$ is substituted or unsubstituted aromatic heterocyclyl; $R^{1b}$ is substituted or unsubstituted 5- to 6-membered aromatic heterocyclyl; $R^{1b}$ is substituted or unsubstituted 5-membered aromatic heterocyclyl (hereinafter referred to as "$R^{1a}$ to $R^{1c}$ are R15").

$R^{1a}$ to $R^{1c}$ are each independently substituted or unsubstituted 5- to 6-membered aromatic heterocyclyl (hereinafter referred to as "$R^{1a}$ to $R^{1c}$ are R16"). $R^{1a}$ and $R^{1b}$ are substituted or unsubstituted 5- to 6-membered aromatic heterocyclyl; $R^{1c}$ is substituted or unsubstituted 5-membered aromatic heterocyclyl (hereinafter referred to as "$R^{1a}$ to $R^{1c}$ are R17").

$R^{1a}$ to $R^{1c}$ are each independently substituted or unsubstituted 5-membered aromatic heterocyclyl (hereinafter referred to as "$R^{1a}$ to $R^{1c}$ are R18").

$R^{1a}$ to $R^{1c}$ are each independently substituted or unsubstituted isoxazolyl (hereinafter referred to as "$R^{1a}$ to $R^{1c}$ are R19").

$R^{1a}$ to $R^{1c}$ are each independently a group represented by:

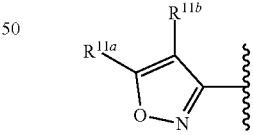

[Chemical Formula 49]

wherein $R^{11a}$ and $R^{11b}$ are each independently a hydrogen atom, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, provided that $R^{11a}$ and $R^{11b}$ are not simultaneously hydrogen atoms (hereinafter referred to as "$R^{1a}$ to $R^{1c}$ are R110").

$R^{1a}$ to $R^{1c}$ are each independently a group represented by:

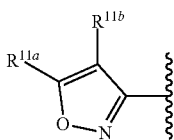

[Chemical Formula 50]

wherein $R^{11a}$ and $R^{11b}$ are each independently a hydrogen atom; substituted or unsubstituted alkyl (examples of the substituents include halogen and non-aromatic carbocyclyl optionally substituted with one or more group(s) selected from the substituent group β2); substituted or unsubstituted alkylcarbonyl (examples of the substituents include halogen and non-aromatic carbocyclyl optionally substituted with one or more group(s) selected from the substituent group β2); substituted or unsubstituted aromatic carbocyclyl (examples of the substituents include the substituent group β1); or substituted or unsubstituted non-aromatic carbocyclyl (examples of the substituents include the substituent group β1), provided that $R^{11a}$ and $R^{11b}$ are not simultaneously hydrogen atoms (hereinafter referred to as "$R^{1a}$ to $R^{1c}$ are R112").

$R^{1a}$ to $R^{1c}$ are each independently a group represented by:

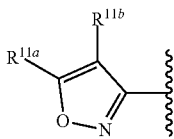

[Chemical Formula 51]

wherein $R^{11a}$ is substituted or unsubstituted alkyl (examples of the substituents include halogen and non-aromatic carbocyclyl optionally substituted with one or more group(s) selected from the substituent group β2) or substituted or unsubstituted alkylcarbonyl (examples of the substituents include halogen and non-aromatic carbocyclyl optionally substituted with one or more group(s) selected from the substituent group β2); and $R^{11b}$ is a hydrogen atom (hereinafter referred to as "$R^{1a}$ to $R^{1c}$ are R113").

$R^{1a}$ to $R^{1c}$ are each independently a group represented by:

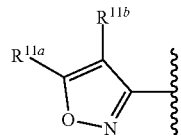

[Chemical Formula 52]

wherein $R^{11a}$ is alkyl or haloalkyl, and $R^{11b}$ is a hydrogen atom (hereinafter referred to as "$R^{1a}$ to $R^{1c}$ care R114").

$R^{1a}$ to $R^{1c}$ are each independently:

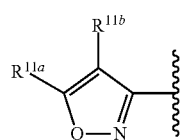

[Chemical Formula 53]

wherein $R^{11a}$ is C1-C6 alkyl optionally substituted with one or more group(s) selected from (monocyclic non-aromatic carbocyclyl substituted with halogen; monocyclic non-aromatic carbocyclyl; and halogen), or monocyclic non-aromatic carbocyclyl optionally substituted with one or more group(s) selected from (halogen; C1-C6 alkyl; and C1-C6 haloalkyl); $R^{11b}$ is a hydrogen atom (hereinafter referred to as "$R^{1a}$ to $R^{1c}$ are R115").

$R^{1a}$ to $R^{1c}$ are each independently:

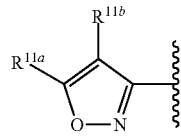

[Chemical Formula 54]

wherein $R^{11a}$ is C1-C6 alkyl optionally substituted with one or more group(s) selected from (3- to 6-membered non-aromatic carbocyclyl substituted with halogen; 3- to 6-membered non-aromatic carbocyclyl; and halogen), or 3- to 6-membered non-aromatic carbocyclyl optionally substituted with one or more group(s) selected from (halogen; C1-C6 alkyl; and C1-C6 haloalkyl); $R^{11b}$ is a hydrogen atom (hereinafter referred to as "$R^{1a}$ to $R^{1c}$ are R116").

$R^{1a}$ is:

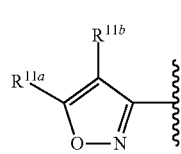

[Chemical Formula 55]

wherein $R^{11a}$ is substituted or unsubstituted alkyl, substituted or unsubstituted non-aromatic carbocyclyl, or substituted or unsubstituted alkylcarbonyl; and $R^{11b}$ is a hydrogen atom; and $R^{1b}$ and $R^{1c}$ are each independently:

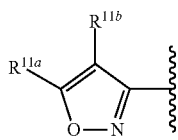

[Chemical Formula 56]

wherein $R^{11a}$ is a hydrogen atom; and $R^{11b}$ is substituted or unsubstituted aromatic carbocyclyl, substituted or unsubstituted non-aromatic carbocyclyl, or substituted or unsubstituted alkyl (hereinafter referred to as "$R^{1a}$ to $R^{1c}$ are R117").

$R^9$ is each independently halogen, hydroxy, cyano, substituted or unsubstituted alkyl, or substituted or unsubstituted alkyloxy;

two $R^9$s attached to different ring-constituting atoms may be taken together to form a substituted or unsubstituted (C1-C3) bridge wherein one of carbon atoms constituting the (C1-C3) bridge may be replaced with an oxygen atom or a nitrogen atom;

two $R^9$s attached to the same carbon atom may be taken together with the carbon atom to which they are attached to form a substituted or unsubstituted 3- to 5-membered non-aromatic carbocycle or a substituted or unsubstituted 3- to 5-membered non-aromatic heterocycle:

two $R^9$ is attached to adjacent carbon atoms may be taken together with the carbon atoms to which they are attached to form a substituted or unsubstituted 3- to 5-membered non-aromatic carbocycle or a substituted or unsubstituted 3- to 5-membered non-aromatic heterocycle (hereinafter referred to as "$R^9$ is R91").

$R^9$ is each independently halogen, hydroxy, cyano, substituted or unsubstituted alkyl, or substituted or unsubstituted alkyloxy;

two $R^5$s attached to different ring-constituting atoms may be taken together to form a substituted or unsubstituted (C1-C3) bridge wherein one of carbon atoms constituting the (C1-C3) bridge may be replaced with an oxygen atom or a nitrogen atom (hereinafter referred to as "$R^9$ is R92").

$R^9$ is each independently halogen, or substituted or unsubstituted alkyl (hereinafter referred to as "$R^6$ is R93").

$R^9$ is each independently halogen (hereinafter referred to as "$R^9$ is R94").

s is an integer of 0 to 4 (hereinafter referred to as "s is s1").

s is an integer of 0 to 2 (hereinafter referred to as "s is s2").

s is 0 (hereinafter referred to as "s is s3").

n is an integer of 0 to 3 (hereinafter referred to as "n is n1").

n is 1 (hereinafter referred to as "n is n2").

$R^{2a}$ is each independently a hydrogen atom, halogen, hydroxy, cyano, substituted or unsubstituted alkyl, or substituted or unsubstituted alkyloxy;

$R^{2b}$ is each independently a hydrogen atom, halogen, hydroxy, cyano, substituted or unsubstituted alkyl, or substituted or unsubstituted alkyloxy;

$R^{2c}$ and $R^{2d}$ are each independently a hydrogen atom, halogen, hydroxy, cyano, substituted or unsubstituted alkyl, or substituted or unsubstituted alkyloxy (hereinafter referred to as "$R^{2a}$ to $R^{2d}$ are R21").

$R^{2a}$ and $R^{2b}$ are hydrogen atoms;

$R^{2c}$ and $R^{2d}$ are each independently a hydrogen atom, halogen, hydroxy, cyano, substituted or unsubstituted alkyl, or substituted or unsubstituted alkyloxy (hereinafter referred to as "$R^{2a}$ to $R^{2d}$ are R22").

$R^{2a}$, $R^{2b}$ and $R^{2c}$ are hydrogen atoms;

$R^{2d}$ is a hydrogen atom, or substituted or unsubstituted alkyloxy (hereinafter referred to as "$R^{2a}$ to $R^{2d}$ are R23").

$R^{2a}$ to $R^{2d}$ are hydrogen atoms (hereinafter referred to as "$R^{2a}$ to $R^{2d}$ are R24").

-L- is —N($R^{10}$)—C(=O)— or —N($R^{10}$)—SO—, and $R^{10}$ is a hydrogen atom or substituted or unsubstituted alkyl (hereinafter referred to as "L is L1").

-L- is —N($R^{10}$)—C(=O)—, and $R^{10}$ is a hydrogen atom or substituted or unsubstituted alkyl (hereinafter referred to as "L is L2").

-L- is —NH—C(=O)— or —NH—SO$_2$— (hereinafter referred to as "L is L").

-L- is —NH—C(=O)— (hereinafter referred to as "L is L4").

Ring B is a non-aromatic carbocycle or a non-aromatic heterocycle (hereinafter referred to as "B is B1").

Ring B is a 4- to 8-membered non-aromatic carbocycle or a 4- to 8-membered non-aromatic heterocycle (hereinafter referred to as "B is B2").

Ring B is a 6-membered non-aromatic carbocycle or a 6-membered non-aromatic heterocycle, or a spiroheptane ring (hereinafter referred to as "B is B3").

Ring B is a 6-membered non-aromatic carbocycle or a 6-membered non-aromatic heterocycle (hereinafter referred to as "B is B4").

Ring B is a cyclohexane ring (hereinafter referred to as "B is B5").

Ring B is a piperidine ring (hereinafter referred to as "B is B6").

[Chemical Formula 57]

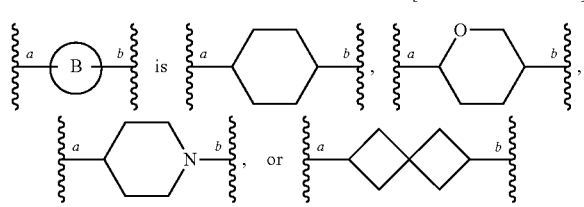

(Hereinafter referred to as "B is B7").

[Chemical Formula 58]

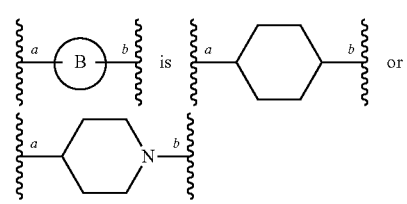

(Hereinafter referred to as "B is B8").

Ring B is a 6- to 8-membered non-aromatic carbocycle or a 6- to 8-membered non-aromatic heterocycle (hereinafter referred to as "B is B9").

[Chemical Formula 59]

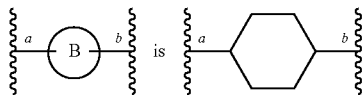 5

(Hereinafter referred to as "B is B10").

R³ is each independently halogen, hydroxy, cyano, substituted or unsubstituted C1-C6 alkyl, or substituted or unsubstituted C1-C6 alkyloxy;

two R³s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom (hereinafter referred to as "R³ is R31").

R³ is each independently halogen, or two R³s attached to different ring-constituting atoms may be taken together to form a substituted or unsubstituted (C1-C3) bridge (hereinafter referred to as "R³ is R32").

R³ is each independently halogen, or two R³s attached to different ring-constituting atoms may be taken together to form a substituted or unsubstituted C2 bridge (hereinafter referred to as "R³ is R33").

R³ is each independently halogen (hereinafter referred to as "R³ is R34").

Two R³s attached to different ring-constituting atoms are taken together to form a C2 bridge (hereinafter referred to as "R³ is R35").

R³ is each independently halogen, or two R³ s attached to different ring-constituting atoms may be taken together to form a substituted or unsubstituted C2 bridge wherein one of carbon atoms constituting the C2 bridge may be replaced with an oxygen atom (hereinafter referred to as "R³ is R36").

r is an integer of 0 to 4 (hereinafter referred to as "r is r1").
r is an integer of 1 to 4 (hereinafter referred to as "r is r2").
r is 1 or 2 (hereinafter referred to as "r is r3").
r is 1 (hereinafter referred to as "r is r4").
r is 0 (hereinafter referred to as "r is r5").
r is 0 or 1 (hereinafter referred to as "r is r6").

R⁴ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl (hereinafter referred to as "R⁴ is R41").

R⁴ is substituted or unsubstituted alkyl, substituted or unsubstituted alkenyl, substituted or unsubstituted aromatic heterocyclyl, or substituted or unsubstituted non-aromatic heterocyclyl (hereinafter referred to as "R4 is R42").

R⁴ is substituted or unsubstituted aromatic carbocyclyl, substituted or unsubstituted non-aromatic carbocyclyl, substituted or unsubstituted non-aromatic heterocyclyl, substituted or unsubstituted aromatic heterocyclyl, —CR⁵ᵃR⁵ᵇ—R⁶, or —CR⁷ᵃ=CR⁷ᵇ—R⁸;

R⁵ᵃ, R⁵ᵇ, R⁷ᵃ and R⁷ᵇ are each independently a hydrogen atom, halogen, substituted or unsubstituted C1-C6 alkyl, or substituted or unsubstituted C1-C6 alkyloxy;

R⁶ is substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy R⁸ is substituted or unsubstituted non-aromatic carbocyclyl, substituted or unsubstituted aromatic carbocyclyl, substituted or unsubstituted non-aromatic heterocyclyl, or substituted or unsubstituted aromatic heterocyclyl (hereinafter referred to as "R⁴ is R43").

R⁴ is substituted or unsubstituted aromatic carbocyclyl (examples of the substituents include the substituent group β1), substituted or unsubstituted non-aromatic heterocyclyl (examples of the substituents include the substituent group β2), substituted or unsubstituted aromatic heterocyclyl (examples of the substituents include the substituent group β1), —CR⁵ᵃR⁵ᵇ—R⁶, or —CR⁷ᵃ=CR⁷ᵇ—R⁸;

R⁵ᵃ, R⁵ᵇ, R⁷ᵃ, and R⁷ᵇ are the same as defined in R43;

R⁶ is substituted or unsubstituted non-aromatic heterocyclyl (examples of the substituents include the substituent group β2), substituted or unsubstituted aromatic heterocyclyl (examples of the substituents include the substituent group β1), substituted or unsubstituted aromatic heterocyclyloxy (examples of the substituents include the substituent group β1), or substituted or unsubstituted non-aromatic heterocyclyloxy (examples of the substituents include the substituent group β2); and R⁸ is substituted or unsubstituted non-aromatic heterocyclyl (examples of the substituents include the substituent group β2), or substituted or unsubstituted aromatic heterocyclyl (examples of the substituents include the substituent group β1 (hereinafter referred to as "R⁴ is R44").

R⁴ is substituted or unsubstituted phenyl (examples of the substituents include the substituent group β1), substituted or unsubstituted 6-membered or bicyclic non-aromatic heterocyclyl (examples of the substituents include the substituent group β2), substituted or unsubstituted 6-membered or bicyclic aromatic heterocyclyl (examples of the substituents include the substituent group β1), —CR⁵ᵃR⁵ᵇ—R⁶, or —CR⁷ᵃ=CR⁷ᵇ—R⁸;

R⁵ᵃ, R⁵ᵇ, R⁷ᵃ, and R⁷ᵇ are the same as defined in R43;

R⁶ is substituted or unsubstituted 5- or 6-membered non-aromatic heterocyclyl (examples of the substituents include the substituent group β2), substituted or unsubstituted 5- or 6-membered aromatic heterocyclyl (examples of the substituents include the substituent group β1), substituted or unsubstituted 5- or 6-membered aromatic heterocyclyloxy (examples of the substituents include the substituent group β1), or substituted or unsubstituted 5- or 6-membered non-aromatic heterocyclyloxy (examples of the substituents include the substituent group β2); and R⁸ is substituted or unsubstituted 5- or 6-membered non-aromatic heterocyclyl (examples of the substituents include the substituent group β2), or substituted or unsubstituted 5- or 6-membered aromatic heterocyclyl (examples of the substituents include the substituent group β1) (hereinafter referred to as "R⁴ is R45").

R⁴ is substituted or unsubstituted 6-membered or bicyclic non-aromatic heterocyclyl (examples of the substituents include the substituent group β2), or substituted or unsubstituted 6-membered or bicyclic aromatic heterocyclyl (examples of the substituents include the substituent group β1) (hereinafter referred to as "R⁴ is R46").

R⁴ is —CR⁵ᵃR⁵ᵇ—R⁶; and R⁵ᵃ, R⁵ᵇ and R⁶ are the same as defined in R45 (hereinafter referred to as "R⁴ is R47").

R⁴ is —CR⁷ᵃ═CR⁷ᵇ—R⁸; and R⁷ᵃ, R⁷ᵇ and R⁸ are the same as defined in R45 (hereinafter referred to as "R⁴ is R48").

R⁴ is substituted or unsubstituted phenyl, substituted or unsubstituted indazolyl, substituted or unsubstituted pyrazolopyridyl, substituted or unsubstituted benzotriazolyl, substituted or unsubstituted pyridyl, substituted or unsubstituted isoindolinyl, substituted or unsubstituted dihydroisoquinolinyl, substituted or unsubstituted dihydropyridyl, —CR⁵ᵃR⁵ᵇ—R⁶, or —CR⁷ᵃ═CR⁷ᵇ—R⁸;

R⁵ᵃ, R⁵ᵇ, R⁷ᵃ, and R⁷ᵇ are the same as defined in R43;

R⁶ is substituted or unsubstituted oxazolyl, substituted or unsubstituted isoxazolyl, substituted or unsubstituted oxadiazolyl, substituted or unsubstituted pyrazolyl, substituted or unsubstituted triazolyl, substituted or unsubstituted thiazolyl, substituted or unsubstituted thiadiazolyl, substituted or unsubstituted pyrimidinyl, substituted or unsubstituted pyrimidinyloxy, substituted or unsubstituted pyrazinyloxy, or substituted or unsubstituted isoxazolyloxy; and R⁸ is substituted or unsubstituted pyrimidinyl or substituted or unsubstituted pyrazolyl (hereinafter referred to as "R⁴ is R49").

R⁴ is substituted or unsubstituted phenyl, substituted or unsubstituted indazolyl, substituted or unsubstituted pyrazolopyridyl, substituted or unsubstituted benzotriazolyl, substituted or unsubstituted pyridyl, substituted or unsubstituted isoindolinyl, substituted or unsubstituted dihydroisoquinolinyl, or substituted or unsubstituted dihydropyridyl (hereinafter referred to as "R⁴ is R410").

R⁴ is —CH₂—R⁶; and R⁶ is the same as defined in R49 (hereinafter referred to as "R⁴ is R411").

R⁴ is —CH═CH—R⁸; and R⁸ is the same as defined in R49 (hereinafter referred to as "R⁴ is R412").

R⁴ is 6-membered or bicyclic non-aromatic heterocyclyl optionally substituted with one or more group(s) selected from the substituent group β2, 6-membered or bicyclic aromatic heterocyclyl optionally substituted with one or more group(s) selected from the substituent group β1, —CH₂—R⁶, or —CH═CH—R⁸;

R⁶ is 5- or 6-membered non-aromatic heterocyclyl optionally substituted with one or more group(s) selected from the substituent group β2, 5- or 6-membered aromatic heterocyclyl optionally substituted with one or more group(s) selected from the substituent group β1, 5- or 6-membered aromatic heterocyclyloxy optionally substituted with one or more group(s) selected from the substituent group β1, or 5- or 6-membered non-aromatic heterocyclyloxy optionally substituted with one or more group(s) selected from the substituent group β2; and R⁸ is 5- or 6-membered non-aromatic heterocyclyl optionally substituted with one or more group(s) selected from the substituent group β2, or 5- or 6-membered aromatic heterocyclyl optionally substituted with one or more group(s) selected from the substituent group β1 (hereinafter referred to as "R⁴ is R413").

Examples of the compound represented by Formula (I) include all the embodiments which are the combinations of:

Cyclyl A is one embodiment selected from A1 to A10;
R¹ᵃ to R¹ᶜ is one embodiment selected from R11 to R117;
R⁹ is one embodiment selected from R91 to R94;
s is one embodiment selected from s1 to s3;
n is n1 or n2;
R²ᵃ to R²ᵈ are one embodiment selected from R21 to R24;
L is one embodiment selected from L1 to L4;
Ring B is one embodiment selected from B1 to B10; and
R³ is one embodiment selected from R31 to R36;
r is one embodiment selected from r1 to r6; and,
R⁴ is one embodiment selected from R41 to R413.

Other examples of preferred embodiments of the compound represented by Formula (I) or a pharmaceutically acceptable salt thereof are illustrated bellow.

A compound represented by Formula (IA) or (IB), more preferably Formula (IB):

[Chemical Formula 60]

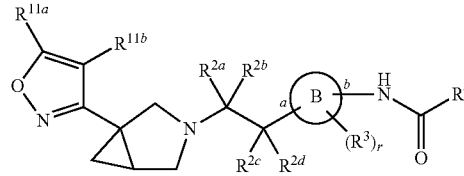
(IA)

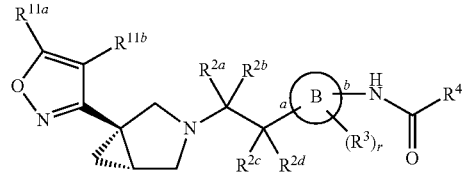
(IB)

wherein each symbol is the same as defined above, or a pharmaceutically acceptable salt thereof.

Examples of specific embodiments of Formulas (IA) and (IB) include embodiments of all combinations of:

R¹¹ᵃ and R¹¹ᵇ are the same as defined in one embodiment selected from R110 to R117;
R²ᵃ to R²ᵈ are one embodiment selected from R21 to R24;
Ring B is one embodiment selected from B1 to B10;
R³ is one embodiment selected from R31 to R36;
r is one embodiment selected from r1 to r6; and,
R⁴ is one embodiment selected from R41 to R413.

Examples of other specific embodiments of Formulas (IA) and (IB), more preferably Formula (B), are illustrated below.

R¹¹ᵃ is C1-C6 alkyl optionally substituted with one or more group(s) selected from (3- to 6-membered non-aromatic carbocyclyl substituted with halogen; 3- to 6-membered non-aromatic carbocyclyl and halogen), or 3 to 6-membered non-aromatic carbocyclyl optionally substituted with one or more group(s) selected from (halogen; C1-C6 alkyl; and C1-C6 haloalkyl); R¹¹ᵇ is a hydrogen atom;

R²ᵃ to R²ᵈ are hydrogen atoms;

Ring B is a 6- to 8-membered non-aromatic carbocycle or a 6- to 8-membered non-aromatic heterocycle;

R³ is each independently halogen; r is an integer of 0 to 2; and

R⁴ is 6-membered or bicyclic non-aromatic heterocyclyl optionally substituted with one or more group(s) selected from the substituent group β2, 6-membered or bicyclic aromatic heterocyclyl optionally substituted with one or more group(s) selected from the substituent group β1, —CH₂—R⁶, or —CH═CH—R⁸;

R⁶ is 5- or 6-membered non-aromatic heterocyclyl optionally substituted with one or more group(s) selected from the substituent group β2, 5- or 6-membered aromatic heterocyclyl optionally substituted with one or more group(s) selected from the substituent group β1, 5- or 6-membered aromatic heterocyclyloxy optionally substituted with one or more group(s)

selected from the substituent group β1, or 5- or 6-membered non-aromatic heterocyclyloxy optionally substituted with one or more group(s) selected from the substituent group β2; and $R^8$ is 5- or 6-membered non-aromatic heterocyclyl optionally substituted with one or more group(s) selected from the substituent group β2, or 5- or 6-membered aromatic heterocyclyl optionally substituted with one or more group(s) selected from the substituent group β1.

$R^{11a}$ is substituted or unsubstituted alkyl; $R^{11b}$ is a hydrogen atom;

$R^{2a}$ to $R^{2d}$ are hydrogen atoms;

Ring B is a 6-membered non-aromatic carbocycle or a 6-membered non-aromatic heterocycle;

$R^3$ is each independently halogen; r is an integer of 0 to 4; and $R^4$ is R45.

$R^{11a}$ is alkyl or haloalkyl, preferably, ethyl optionally substituted with one or more halogen;

$R^{11b}$ is a hydrogen atom;

$R^{2a}$ to $R^{2d}$ are hydrogen atoms:

[Chemical Formula 61]

$R^3$ is each independently halogen; r is an integer of 0 to 2; and $R^4$ is R49.

Still other aspects of preferred embodiments of the compound represented by Formula (I) or a pharmaceutically acceptable salt thereof are illustrated bellow.

A compound represented by Formula (IC) or (ID), more preferably Formula (ID):

[Chemical Formula 62]

(IC)

(ID)

wherein each symbol is the same as defined above, or a pharmaceutically acceptable salt thereof.

Examples of specific embodiments of Formulas (IC) and (ID) include embodiments of all combinations of $R^{11a}$ and $R^{11b}$ are the same as defined in one embodiment selected from R110 to R117;

$R^{2a}$ to $R^{2d}$ are one embodiment selected from R21 to R24;

Ring B is one embodiment selected from B1 to B10;

$R^3$ is one embodiment selected from R31 to R36;

r is one embodiment selected from r1 to r6; and $R^4$ is one embodiment selected from R41 to R413.

Other specific embodiments of Formulas (IC) and (ID) are illustrated below.

$R^{11a}$ is a hydrogen atom; $R^{11b}$ is substituted or unsubstituted phenyl (examples of the substituents include halogen), substituted or unsubstituted 3- to 6-membered non-aromatic carbocyclyl (examples of the substituents include halogen), or substituted or unsubstituted alkyl (examples of the substituents include halogen and cyclopropyl);

$R^{2a}$ to $R^{2d}$ are hydrogen atoms;

Ring B is a 6-membered non-aromatic carbocycle or a 6-membered non-aromatic heterocycle;

$R^3$ is each independently halogen; r is an integer of 0 to 4; and $R^4$ is R45.

$R^{11a}$ is a hydrogen atom; $R^{11b}$ is haloalkyl;

$R^{2a}$ to $R^{2d}$ are hydrogen atoms:

[Chemical Formula 63]

$R^3$ is each independently halogen; r is an integer of 0 to 2; and $R^4$ is R49.

The compounds represented by Formula (I) are not limited to specific isomers but include all possible isomers (e.g., keto-enol isomers, imine-enamine isomers, diastereoisomers, enantiomers, rotamers or the like), racemates or mixtures thereof.

One or more hydrogen, carbon and/or other atoms in the compounds represented by Formula (I) may be replaced with isotopes of hydrogen, carbon and/or other atoms respectively. Examples of isotopes include hydrogen, carbon, nitrogen, oxygen, phosphorus, sulfur, fluorine, iodine and chlorine, such as a $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$, respectively. The compounds represented by Formula (I) include the compounds replaced with these isotopes. The compounds replaced with the isotopes are useful as medicaments and include all radiolabeled compounds of the compound represented by Formula (I). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds represented by Formula (I) can be prepared using well-known methods in the art. For example, a tritium-labeled compound represented by Formula (I) can be prepared by introducing tritium to a certain compound represented by Formula (I), through a catalytic dehalogenation reaction using tritium. This method comprises reacting an appropriately-halogenated precursor of the compound represented by Formula (I) with tritium gas in the presence of an appropriate catalyst, such as Pd/C, and in the presence or absence of a base. The other appropriate method for preparing a tritium-labeled compound can be referred to "Isotopes in the Physical and Biomedical Sciences, Vol. 1, Labeled Compounds (Part A), Chapter 6 (1987)". A $^{14}$C-labeled compound can be prepared by using a raw material having $^{14}$C.

Examples of the pharmaceutically acceptable salts of the compounds represented by Formula (I) include salts of the compounds represented by Formula (I) with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid or the like are included. These salts can be formed by the usual methods.

The compounds represented by Formula (I) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds represented by Formula (I). When the compounds represented by Formula (I) or pharmaceutically acceptable salts thereof are allowed to be left stand in the atmosphere, the compounds may absorb water, resulting in attachment of adsorbed water or formation of hydrates. Recrystallization of the compounds represented by Formula (I) or pharmaceutically acceptable salts thereof may produce crystal polymorphs.

The compounds represented by Formula (I) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds represented by Formula (I) through enzymatic oxidation, reduction, hydrolysis or the like under physiological conditions in vivo, compounds that are converted to the compounds represented by Formula (I) through hydrolysis by gastric acid or the like, and the like. Methods for selecting and preparing suitable prodrug derivatives are described in, for example, "Design of Prodrugs, Elsevier, Amsterdam, 1985". Prodrugs themselves may have some activity.

When the compounds represented by Formula (I) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. Examples thereof include $CH_3COO-$, $C_2H_5COO-$, tert-BuCOO-, $C_{15}H_{31}COO-$, PhCOO-, (m-NaOOCPh)COO-, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-PhSO$_3-$, PhSO$_3-$, and p-$CH_3$PhSO$_3-$.

(Method for Producing the Compounds of the Present Invention)

The compounds represented by Formula (I) of the present invention can be, for example, prepared by the general synthetic procedures described below. The starting materials and reaction reagents used for synthesizing these compounds are commercially available or can be manufactured in accordance with well-known methods in the art using commercially available compounds. The methods for extraction, purification and the like may be carried out by usual methods for the experiments of organic chemistry.

The compounds of the present invention can be synthesized by referring to the known methods in the art.

In all the following steps, when a substituent which interferes with the reaction, e.g. hydroxy, mercapto, amino, formyl, carbonyl, carboxyl, is possessed, the substituent may be protected by the method such as those described in Protective Groups in Organic Synthesis, Theodora W Greene (John Wiley & Sons) in advance, and the protective group may be removed at a desirable step.

During all the following steps, the order of the steps to be performed may be appropriately changed. In each step, an intermediate may be isolated and then used in the next step. All of reaction time, reaction temperature, solvents, reagents, protecting groups, and the like are mere exemplification, and not limited as long as they do not cause an adverse effect on a reaction.

The compounds represented by Formula (I) of the present invention can be, for example, prepared by the synthetic routes described below.

(Method A)

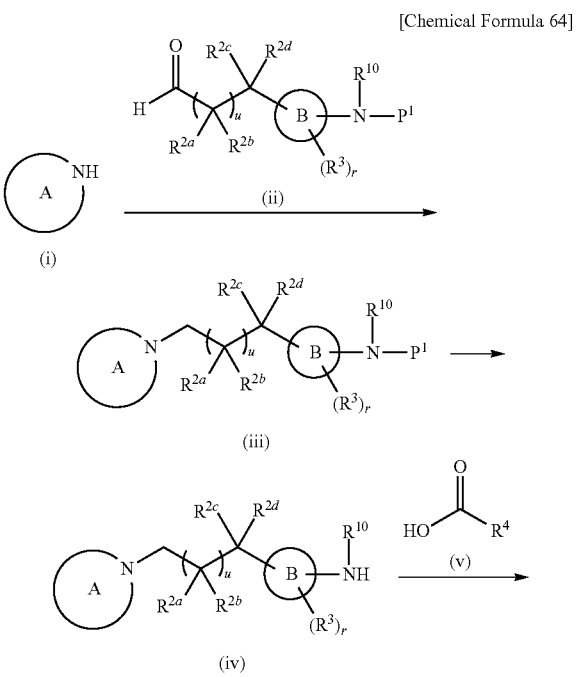

[Chemical Formula 64]

-continued

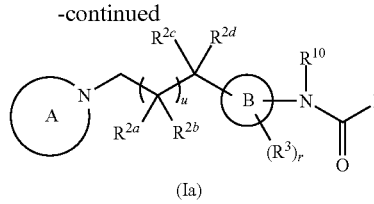

(Ia)

wherein u is an integer of 0 to 2, $P^1$ is a protective group for amino group, and other symbols each are the same as defined above.

(Step 1)

Compound (iii) can be prepared by condensation of Compound (ii) and amine (i) or a salt thereof in the presence or absence of a condensing agent, and reduction of the resulted compound using a reducing agent.

As the condensing agent, p-toluenesulfonic acid, methanesulfonic acid, acetic acid, magnesium sulfate anhydrous, tetraisopropyl orthotitanate, titanium tetrachloride, molecular sieve and the like are exemplified. The condensing agent can be used in 1 to 10 mole equivalent(s) per an equivalent of Compound (ii).

Amine (i) or a salt thereof can be used in 1 to 10 mole equivalent(s) per an equivalent of Compound (ii).

As the reducing agent, sodium borohydride, sodium cyanoborohydride, sodium triacetoxyborohydride, borane and a complex thereof, lithium borohydride, potassium borohydride, diisobutylaluminium hydride and the like are exemplified. The reducing agent can be used in 1 to 10 mole equivalent(s) per an equivalent of Compound (ii).

The reaction temperature is −78° C. to reflux temperature of the solvent, preferably 0 to 25° C.

The reaction time is 0.5 to 48 hours, preferably 1 hour to 6 hours.

As the reaction solvent, tetrahydrofuran, toluene, dichloromethane, 1,2-dichloroethane, chloroform, methanol, ethanol and the like are exemplified. The reaction solvent can be used alone or in combination.

(Step 2)

Compound (iv) can be synthesized by removing a protective group $P^1$ of Compound (iii) according to the methods described in Protective Group in Organic Synthesis, Greene (4th edition).

(Step 3)

Compound (Ia) can be prepared by reacting Compound (iv) with Compound (v) in the presence of a condensing agent.

As the condensing agent, dicyclohexylcarbodiimide, carbonyldiimidazole, dicyclohexylcarbodiimide-N-hydroxybenzotriazole, EDC, 4-(4,6-dimethoxy-1,3,5,-triazin-2-yl)-4-methylmorpholinium chloride, HATU and the like are exemplified. The condensing agent can be used in 1 to 5 mole equivalent(s) per an equivalent of Compound (iv).

The reaction temperature is −20° C. to 60° C., preferably 0° C. to 30° C.

The reaction time is 0.1 hour to 24 hours, preferably 1 hour to 12 hours.

As the reaction solvent, DMF, DMA, N-methyl-2-pyrrolidone, tetrahydrofuran, dioxane, dichloromethane, acetonitrile and the like are exemplified. The reaction solvent can be used alone or in combination.

(Method B)

[Chemical Formula 65]

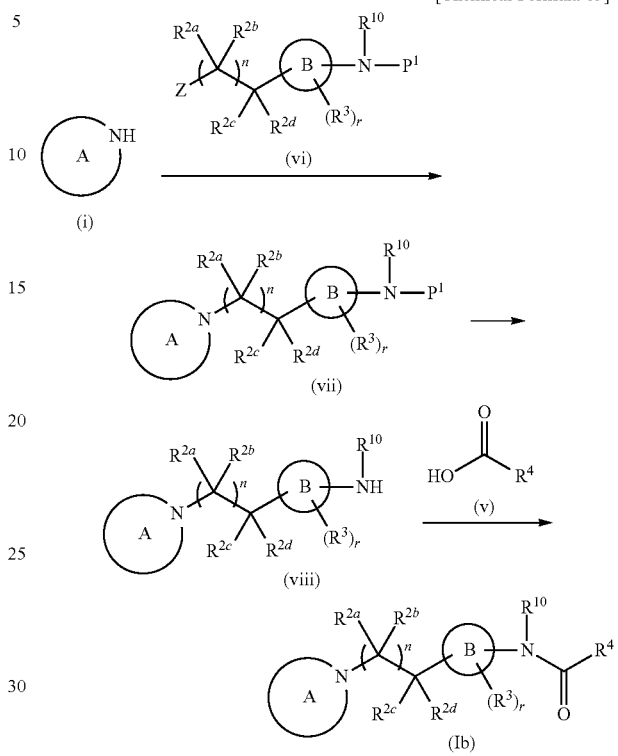

wherein Z is halogen or sulfonate ester, and other symbols each are the same as defined above.

(Step 1)

Compound (vii) can be prepared by reacting Compound (vi) with amine (i) in the presence of a base such as potassium carbonate and the like.

The reaction temperature is 0° C. to reflux temperature of the solvent, preferably room temperature to reflux temperature of the solvent.

The reaction time is 0.1 hour to 24 hours, preferably 1 hour to 12 hours.

As the reaction solvent, DMF, DMA, N-methyl-2-pyrrolidone, tetrahydrofuran, dioxane, dichloromethane, acetonitrile and the like are exemplified. The reaction solvent can be used alone or in combination.

(Step 2)

Compound (viii) can be synthesized according to the similar synthetic procedures described in Step 2 of Method A.

(Step 3)

Compound (Ib) can be synthesized according to the similar synthetic procedures described in Step 3 of Method A.

A compound of Formula (I) wherein -L- is —N($R^{10}$)—$SO_2$— can be synthesized according to the similar methods described in Method A or Method B by using a sulfonic acid corresponding to Compound (v).

The compounds of the present invention have an antagonistic activity for D3 receptor and preferably high D3/D2 selectivity, and thus, are useful as a therapeutic agent and/or preventive agent for diseases associated with D3 receptor. In the present invention, "a therapeutic agent and/or preventive agent" includes agents for symptom improving.

As diseases associated with D3 receptor, central nervous system diseases are exemplified.

As central nervous system diseases, cognitive disorders (e.g., mild cognitive impairment, Alzheimer's disease and the like), drug addiction, depression, anxiety, drug dependence, gambling addiction, dementia, memory impairment, schizophrenia, schizoaffective disorder, bipolar disorder, mania, acute mania, psychotic disorders including psychotic depression, psychoses including paranoia and delusion, attention-deficit/hyperactivity disorder (AD/HD), attention deficit disorder (ADD), obsessive-compulsive disorder (OCD), dyskinesia disorder, Parkinson's disease, neuroleptic-induced Parkinson's syndrome and tardive dyskinesia, eating disorders (e.g., anorexia or bulimia), sexual dysfunction, intellectual disabilities, learning disabilities, developmental disorders, sleep disorders, emesis, movement disorders, obsessive-compulsive disorder, amnesia, aggression, autism, vertigo, circadian rhythm disorders and gastric motility disorders, drug abuse (e.g., opioid drugs, alcohol, cocaine and nicotine addiction and the like), and psychological dependence due to drug abuse and the like are exemplified.

As central nervous system diseases, more preferably, attention-deficit/hyperactivity disorder (AD/HD) is exemplified.

The compounds of the present invention not only have an antagonistic activity for D3 receptor but also are useful as a medicament and has any or all of the following superior characteristics:
a) The inhibitory activity for CYP enzymes (e.g., CYP1A2, CYP2C9, CYP2C19, CYP2D6, CYP3A4 and the like) is weak.
b) The compound demonstrates good pharmacokinetics, such as a high bioavailability, moderate clearance and the like.
c) The compound has a high metabolic stability.
d) The compound has no irreversible inhibitory action against CYP enzymes (e.g., CYP3A4) when the concentration is within the range described in the present description as the measurement conditions.
e) The compound has no mutagenicity.
f) The compound is associated with a low cardiovascular risk.
g) The compound has a high solubility.
h) The compound has a high D3 receptor selectivity (e.g., the compound has a high D3 receptor selectivity over D2 receptor, muscarinic receptor, adrenergic al receptor, histamine H1 receptor, and/or serotonin 5HT2c receptor).
i) The compound has a high D3 receptor selectivity over D2 receptor. In other words, the compound has a high D3/D2 selectivity (e.g., the compound has higher affinity for D3 receptor compared to affinity for D2 receptor).
j) The compound has a high safety (e.g., mydriasis or somnolence can be reduced, teratogenicity risk is low, or the like).
k) The compound has high brain distribution ability.
l) The compound has a low propensity to be P-gp substrate.
m) The compound shows high D3 receptor occupancy. For example, the compound shows high D3 receptor occupancy at low doses.

Since the compounds of the present invention have a high antagonistic activity against D3 receptor and/or a high D3 receptor selectivity over other receptors, e.g., D2 receptor (e.g., have higher affinity for D3 receptor compared to affinity for other receptor(s), e.g., D2 receptor), it can be a medicament with reduced side effects. Examples of the side effects include extrapyramidal symptoms, elevated prolactin, and reduced cognitive function.

As D3 receptor antagonists, for example, preferably compounds which show Ki value of less than or equal to 10 µM, more preferably less than or equal to 100 nM, further more preferably less than or equal to 5 nM in the test of binding inhibition for dopamine D3 receptor, which is described later, are exemplified.

As D3 receptor antagonists, for example, preferably compounds which has D3/D2 selectivity of more than or equal to 10 folds, more preferably more than or equal to 100 folds, further more preferably more than or equal to 500 folds in the test of binding inhibition for dopamine D3 receptor and the test of binding inhibition for dopamine D2 receptor, which are described later, are exemplified.

Here, D3/D2 selectivity can be calculated, for example, from (Ki value in the test of binding inhibition for dopamine D2 receptor/Ki value in the test of binding inhibition for dopamine D3 receptor).

A pharmaceutical composition of the present invention can be administered orally or parenterally. Examples of methods for parenteral administration include dermal, subcutaneous, intravenous, intraarterial, intramuscular, intraperitoneal, transmucosal, inhalation, transnasal, ophthalmic, inner ear, and vaginal administration.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may be prepared according to the usual method, and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing, as appropriate, an effective amount of the compound of the present invention with various pharmaceutical additives suitable for the formulation, such as excipients, binders, disintegrants, lubricants and the like. Furthermore, the pharmaceutical composition can be for pediatric patients, geriatric patients, patients in serious cases, or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route, and the like, a usual oral dosage is 0.05 to 100 mg/kg/day and preferably 0.1 to 10 mg/kg/day. For parenteral administration, although the dosage highly varies with administration routes, a usual dosage is 0.005 to 10 mg/kg/day and preferably 0.01 to 1 mg/kg/ day. The dosage may be administered once daily or may be divided into multiple daily doses.

The compound of the present invention can be used in combination with other drugs such as central nervous system stimulants (Methylphenidate, Lisdexamfetamine and the like), noradrenaline reuptake inhibitor, dopamine-noradrenaline reuptake inhibitor, serotonin-noradrenaline reuptake inhibitor (Atomoxetine and the like), α2A adrenergic receptor agonist (Guanfacine and the like) and the like (hereinafter referred to as a concomitant medicament). The compound of the present invention can be used in combination with the concomitant medicament for the purpose of enforcement of the activity of the compound of the present invention or the concomitant medicament or reduction of the dosage of the compound of the present invention or the concomitant medicament or the like.

In this case, timing of administration of the compound of the present invention and the concomitant medicament is not limited and these may be administered to the subject simultaneously or at regular intervals. Furthermore, the compound of the present invention and the concomitant medicament may be administered as two different formulations containing each active ingredient or as a single formulation containing both active ingredients.

The dosage of the concomitant medicaments may be appropriately selected in reference to the clinical dose. The compounding ratio of the compound of the present invention and the concomitant medicament may be appropriately selected depending on the subject of administration, administration route, disease to be treated, symptoms, combination of the drugs and the like. For example, when the subject of administration is human, the concomitant medicament can be used in the range of 0.01 to 100 parts by weight relative to 1 part by weight of the compound of the present invention.

EXAMPLES

The present invention will be described in more detail with reference to, but not limited to, the following Examples and Test Examples.

In this present description, the meaning of each abbreviation is as follows:
Me methyl
Et ethyl
Boc tert-butoxycarbonyl
Boc$_2$O di-tert-butyl dicarbonate
Bn benzyl
Tf trifluoromethanesulfonyl
TFA trifluoroacetic acid
THF tetrahydrofuran
EDC 1-ethyl-3-(3-dimethylaminopropyl)carbodiimide
TBAF tetrabutylammonium fluoride
DMSO dimethyl sulfoxide
DMF dimethylformamide
DMA dimethylacetamide
DME 1,2-dimethoxyethane
dba dibenzylideneacetone
dppf 1,1'-bis(diphenylphosphino)ferrocene
DIAD diisopropyl azodicarboxylate
DEAD diethyl azodicarboxylate
DIEA N,N-diisopropylethylamine
DIBAL diisobutylaluminium hydride
LHMDS lithium hexamethyldisilazide
NaHMDS sodium hexamethyldisilazide
NCS N-chlorosuccinimide
NIS N-iodosuccinimide
TBS tert-butyldimethylsilyl HATU 1-[bis(dimethylamino)methylene]-1H-1,2,3-triazolo[4,5-b]pyridinium 3-oxide hexafluorophosphate
HOBt 1-hydroxybenzotriazole
CDCl$_3$ deuterochloroform
CD$_3$OD tetradeuteromethanol
MS mass spectrometry
SFC supercritical fluid chromatography NMR analysis of each example was performed by 400 MHz using DMSO-ds, CDCl$_3$, or CD$_3$OD. Sometimes not all the peaks detected are shown in NMR data.

LC/MS data of the compounds of the present invention were measured under the conditions as below. Retention time (min) and m/z are described.

(Method 1)
Column: ACQUITY UPLC(R) BEH C18 (1.7 μm, i.d.2.1×50 mm) (Waters)
Flow rate: 0.8 mL/min
LV detection wavelength: 254 nm
Mobile phases: [A] 10 mM aqueous ammonium carbonate solution, [B] acetonitrile
Gradient: linear gradient of 5% to 100% solvent [B] was performed for 3.5 minutes, and then 100% solvent [B] was maintained for 0.5 minutes.

(Method 2)
Column: ACQUITY UPLC(R) BEH C18 (1.7 μm, i.d.2.1×50 mm) (Waters)
Flow rate: 0.8 mL/min
UV detection wavelength: 254 nm
Mobile phase: [A] an aqueous solution containing 0.1% formic acid, [B] an acetonitrile solution containing 0.1% formic acid
Gradient: linear gradient of 5% to 100% solvent [B] was performed for 3.5 minutes, and then 100% solvent [B] was maintained for 0.5 minutes.

(Method 3)
Column: Shim-pack XR-ODS (2.2 μm, i.d.3.0×50 mm) (Shimadzu)
Flow rate: 1.6 mL/min
UV detection wavelength: 254 nm
Mobile phase: [A] an aqueous solution containing 0.1% formic acid, [B] an acetonitrile solution containing 0.1% formic acid
Gradient: linear gradient of 10% to 100% solvent [B] was performed for 3 minutes, and then 100% solvent [B] was maintained for 0.5 minutes.

(Method 4)
Column: ACQUITY UPLC(R) BEH C18 (1.7 μm, i.d.2.1×50 mm) (Waters)
Flow rate: 0.55 mL/min
UV detection wavelength: 254 nm
Mobile phase: [A] an aqueous solution containing 0.1% formic acid, [B] an acetonitrile solution containing 0.1% formic acid
Gradient: linear gradient of 5% to 100% solvent [B] was performed for 3 minutes, and then 100% solvent [B] was maintained for 0.5 minutes.

Reference Example 1 Synthesis of Compound 6

[Chemical Formula 66]

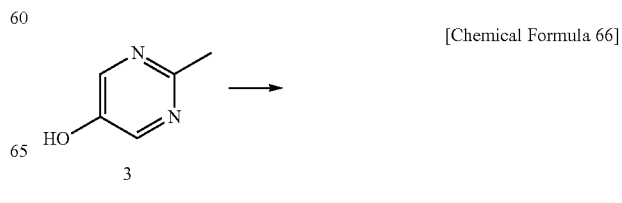

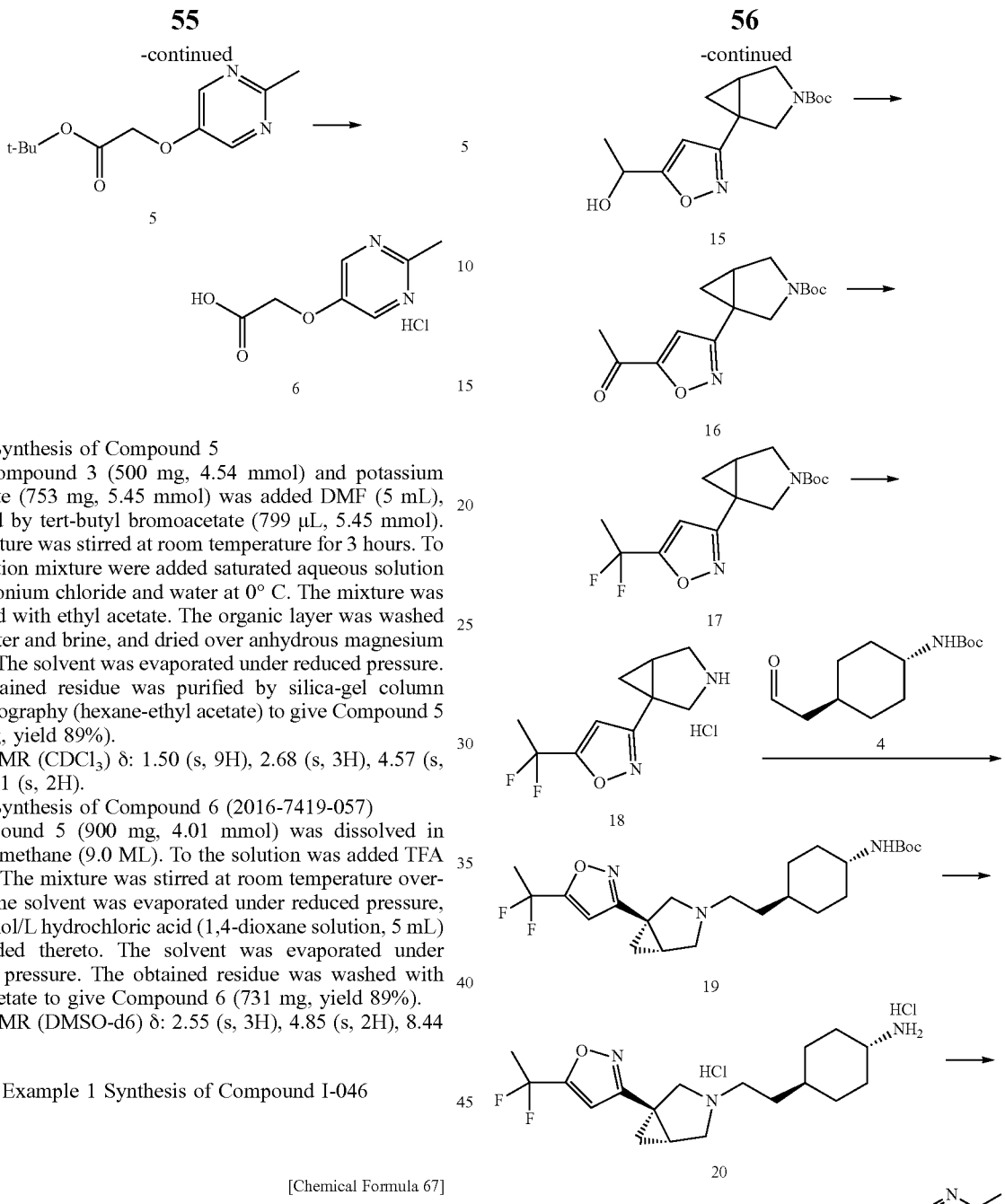

Step 1 Synthesis of Compound 5

To Compound 3 (500 mg, 4.54 mmol) and potassium carbonate (753 mg, 5.45 mmol) was added DMF (5 mL), followed by tert-butyl bromoacetate (799 μL, 5.45 mmol). The mixture was stirred at room temperature for 3 hours. To the reaction mixture were added saturated aqueous solution of ammonium chloride and water at 0° C. The mixture was extracted with ethyl acetate. The organic layer was washed with water and brine, and dried over anhydrous magnesium sulfate. The solvent was evaporated under reduced pressure. The obtained residue was purified by silica-gel column chromatography (hexane-ethyl acetate) to give Compound 5 (905 mg, yield 89%).

1H-NMR (CDCl$_3$) δ: 1.50 (s, 9H), 2.68 (s, 3H), 4.57 (s, 2H), 8.31 (s, 2H).

Step 2 Synthesis of Compound 6 (2016-7419-057)

Compound 5 (900 mg, 4.01 mmol) was dissolved in dichloromethane (9.0 ML). To the solution was added TFA (3 mL). The mixture was stirred at room temperature overnight. The solvent was evaporated under reduced pressure, then 4 mol/L hydrochloric acid (1,4-dioxane solution, 5 mL) was added thereto. The solvent was evaporated under reduced pressure. The obtained residue was washed with ethyl acetate to give Compound 6 (731 mg, yield 89%).

1H-NMR (DMSO-d6) δ: 2.55 (s, 3H), 4.85 (s, 2H), 8.44 (s, 2H).

Example 1 Synthesis of Compound I-046

[Chemical Formula 67]

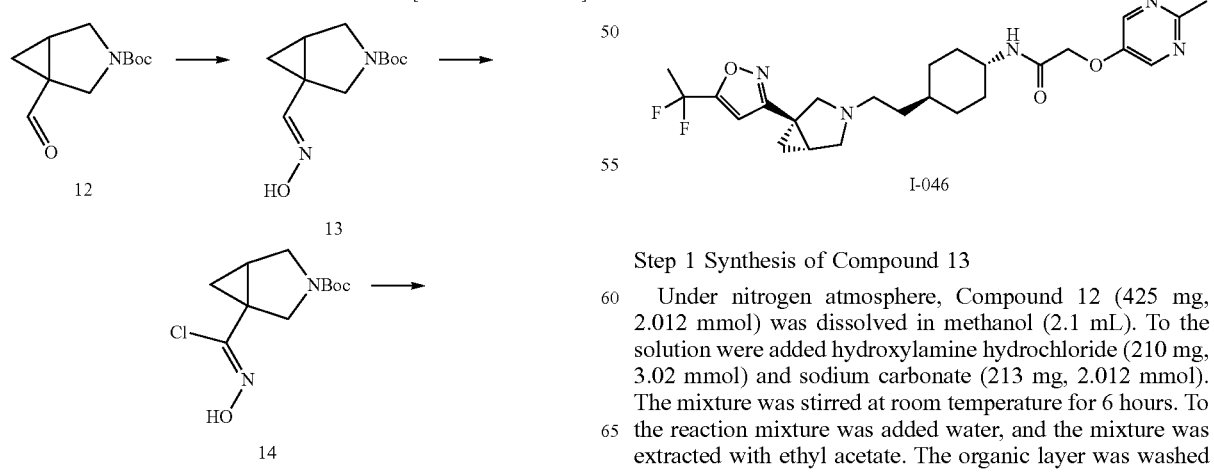

Step 1 Synthesis of Compound 13

Under nitrogen atmosphere, Compound 12 (425 mg, 2.012 mmol) was dissolved in methanol (2.1 mL). To the solution were added hydroxylamine hydrochloride (210 mg, 3.02 mmol) and sodium carbonate (213 mg, 2.012 mmol). The mixture was stirred at room temperature for 6 hours. To the reaction mixture was added water, and the mixture was extracted with ethyl acetate. The organic layer was washed with water and dried over anhydrous sodium sulfate. The solvent was evaporated under reduced pressure to give Compound 13 (403 mg, yield 89%) as a crude product.

Step 2 Synthesis of Compound 14

Compound 13 (403 mg, 1.780 mmol) was dissolved in DMF (4.0 mL). To the solution, NCS (261 mg, 1.958 mmol) was added. The mixture was stirred at room temperature overnight. To the reaction mixture was added water, and the mixture was extracted with ethyl acetate. The organic layer was washed with water, and dried over anhydrous sodium sulfate. The solvent was evaporated under reduced pressure to give Compound 14 (485 mg) as a crude product.

Step 3 Synthesis of Compound 15

Compound 14 (485 mg, 1.786 mmol) was dissolved in ethyl acetate (4.9 mL). To the solution were added 3-butyn-2-ol (279 µL, 3.57 mmol) and sodium hydrogen carbonate (450 mg, 5.36 mmol). The mixture was stirred at room temperature overnight. To the reaction mixture was added water, and the mixture was extracted with ethyl acetate. The organic layer was washed with water, and dried over anhydrous sodium sulfate. The solvent was evaporated under reduced pressure. The obtained residue was purified by silica-gel column chromatography (hexane-ethyl acetate) to give Compound 15 (312 mg, yield 59%).

1H-NMR (CDCl3) δ: 0.95-1.01 (m, 1H), 1.24-1.35 (m, 1H), 1.46 (s, 9H), 1.57 (d, J=6.7 Hz, 3H), 1.86-1.92 (m, 1H), 2.31-2.37 (m, 1H), 3.47-3.50 (m, 1H), 3.61-3.94 (m, 3H), 4.94-5.01 (m, 1H), 5.91-5.98 (m, 1H).

Step 4 Synthesis of Compound 16

Compound 15 (310 mg, 1.053 mmol) was dissolved in dichloromethane (3.1 mL). To the solution was added Dess-Martin Periodinane (581 mg, 1.369 mmol). The mixture was stirred at room temperature for 4.5 hours. The reaction mixture was filtered and then the solvent was evaporated under reduced pressure. The obtained residue was purified by silica-gel column chromatography (hexane-ethyl acetate) to give Compound 16 (312 mg, yield 100%).

1H-NMR (CDCl3) δ: 1.04-1.09 (m, 1H), 1.30-1.39 (m, 1H), 1.46 (s, 9H), 1.92-1.96 (m, 1H), 2.54-2.68 (m, 3H), 3.49-3.53 (m, 1H), 3.63-3.99 (m, 3H), 6.61-6.66 (m, 1H).

Step 5 Synthesis of Compound 17

Compound 16 (308 mg, 1.054 mmol) was dissolved in bis(2-methoxyethyl)aminosulfur trifluoride (777 µL, 4.21 mmol). The solution was stirred at 80° C. for 2 hours. To the reaction mixture were added water and saturated aqueous solution of sodium hydrogen carbonate. The mixture was extracted with ethyl acetate. The organic layer was washed with water and dried over anhydrous sodium sulfate. The solvent was evaporated under reduced pressure. The obtained residue was purified by silica-gel column chromatography (hexane-ethyl acetate) to give Compound 17 (276 mg, yield 83%).

1H-NMR (CDCl3) δ: 1.01-1.06 (m, 1H), 1.30-1.37 (m, 1H), 1.46 (s, 9H), 1.90-2.05 (m, 4H), 3.48-3.52 (m, 1H), 3.63-3.98 (m, 3H), 6.19-6.25 (m, 1H).

Step 6 Synthesis of Compound 18

Compound 17 (960 mg, 3.05 mmol) was dissolved in ethyl acetate (4.8 mL). To the solution was added 4 mol/L hydrochloric acid (1,4-dioxane solution, 7.6 mL, 30.5 mmol). The mixture was stirred at room temperature for 1 hour. The solvent was evaporated under reduced pressure to give Compound 18 (760 mg) as a crude product.

Step 7 Synthesis of Compound 19

Compound 18 (380 mg) was dissolved in dichloromethane (9.6 mL). To the solution were added triethylamine (635 µL, 4.58 mmol), Compound 4 (369 mg, 1.53 mmol) and sodium triacetoxyborohydride (486 mg, 2.29 mmol). The mixture was stirred at room temperature for 1 hour. To the reaction mixture was added saturated aqueous solution of sodium hydrogen carbonate. The mixture was extracted with chloroform. The organic layer was separated and then the solvent of the obtained organic layer was evaporated under reduced pressure. The obtained residue was purified by aminosilica-gel column chromatography (hexane-ethyl acetate) and then subjected to SFC chiral preparative separation to give Compound 19 (220 mg) as an optically active compound.

SFC preparative condition
Preparative column (IF-IF, Daicel)
Flow rate: 30 mL/min
Mobile phase: methanol+0.1% diethylamine 30%
Sample: 50 mg/mL (methanol/chloroform=1/1)
Loading amount: 40 mg
Detection wavelength: 220 nm, Back pressure: 8 Mpa 1H-NMR (DMSO-d6) δ: 0.85-0.97 (m, 2H), 1.04-1.21 (m, 4H), 1.24-1.41 (m, 13H), 1.66-1.75 (m, 4H), 1.85-1.88 (m, 1H), 2.03 (t, J=19.2 Hz, 3H), 2.33 (dd, J=8.8, 3.5 Hz, 1H), 2.42 (t, J=7.4 Hz, 2H), 2.61 (d, J=8.8 Hz, 1H), 2.99 (d, J=8.8 Hz, 1H), 3.09-3.20 (m, 2H), 6.66 (d, J=8.0 Hz, 1H), 6.85 (s, 1H).

Step 8 Synthesis of Compound 20

To Compound 19 (19 mg, 0.043 mmol) were added methanol (62 µL) and 4 mol/L hydrochloric acid (1,4-dioxane solution, 216 µL, 0.865 mmol). The mixture was stirred at room temperature for 3 hours. The solvent was evaporated under reduced pressure to give Compound 20 as a crude product.

Step 9 Synthesis of I-046

Compound 20 obtained as a crude product in Step 8 was dissolved in DMF (249 µL). To the solution were added Compound 6 (9 mg), triethylamine (30 µL, 0.216 mmol), EDC hydrochloride (12.4 mg, 0.065 mmol) and HOBt (1.99 mg, 0.013 mmol). The mixture was stirred at room temperature overnight. To the reaction mixture was added saturated aqueous solution of sodium hydrogen carbonate. The mixture was extracted with chloroform. The organic layer was separated, concentrated, and purified by reverse phase chromatography (acetonitrile-10 mM aqueous ammonium carbonate solution) to give I-046 (19 mg, yield 90%).

1H-NMR (CDCl3) δ: 0.99-1.33 (m, 6H), 1.37-1.42 (m, 2H), 1.77-1.81 (m, 3H), 1.94-2.04 (m, 5H), 2.35-2.51 (m, 3H), 2.70-2.71 (m, 4H), 3.08 (d, J=8.2 Hz, 1H), 3.31 (d, J=8.5 Hz, 1H), 3.79-3.87 (m, 1H), 4.51 (s, 2H), 6.16 (s, 1H), 6.25 (d, J=8.3 Hz, 1H), 8.36 (s, 2H).

Example 2 Synthesis of Compound I-049

[Chemical Formula 68]

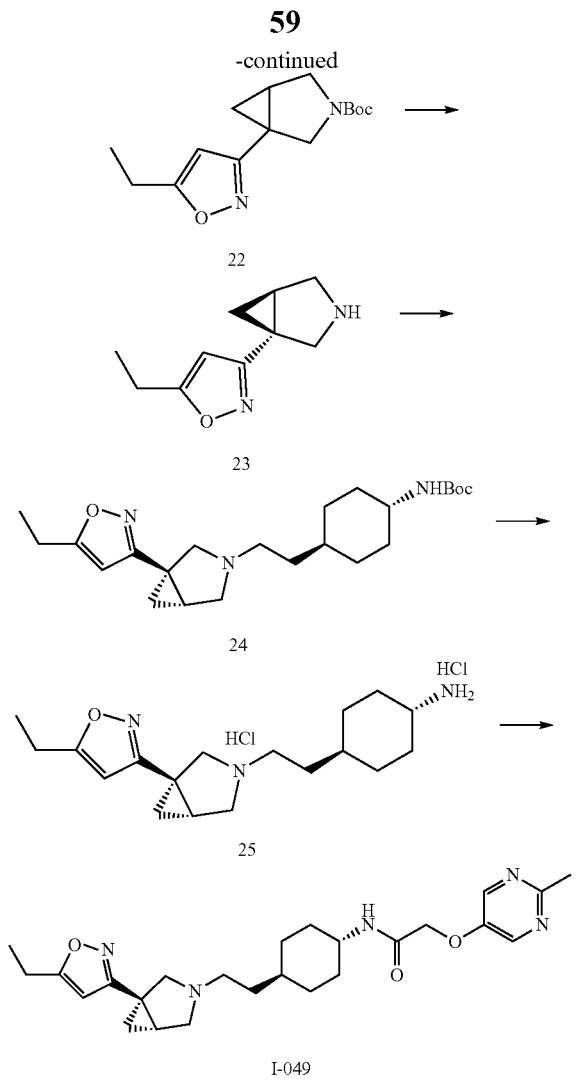

Step 1 Synthesis of Compound 21

Compound 15 (435 mg, 1.476 mmol) was dissolved in dichloromethane (4.35 mL). To the solution were added triethylamine (614 μL, 4.43 mmol) and methanesulfonyl chloride (173 μL, 2.215 mmol) at 0° C. The mixture was stirred at room temperature for 2 hours. To the reaction mixture was added saturated aqueous solution of sodium hydrogen carbonate. The mixture was extracted with ethyl acetate. The organic layer was washed with water and dried over anhydrous sodium sulfate. The solvent was evaporated under reduced pressure. The obtained residue was purified by silica-gel column chromatography (hexane-ethyl acetate) to give Compound 21 (497 mg, yield 90%).

1H-NMR (CDCl3) δ: 1.00-1.04 (m, 1H), 1.28-1.36 (m, 1H), 1.46 (s, 9H), 1.78 (d, J=6.8 Hz, 3H), 1.89-1.93 (m, 1H), 3.03 (s, 3H), 3.48-3.52 (m, 1H), 3.62-3.96 (m, 3H), 5.79 (q, J=6.7 Hz, 1H), 6.07-6.12 (m, 1H).

Step 2 Synthesis of Compound 22

Compound 21 (495 mg, 1.329 mmol) was dissolved in THF (1.49 mL). To the solution was added lithium triethylborohydride (THF solution, 1.02 mol/L, 3.91 mL, 3.99 mmol) at 0° C. The mixture was stirred at room temperature for 4 hours. The reaction mixture was cooled to 0° C., and 1 mol/L hydrochloric acid was added thereto. The mixture was extracted with ethyl acetate. The organic layer was washed with water and saturated aqueous solution of sodium hydrogen carbonate, and then dried over anhydrous sodium sulfate. The solvent was evaporated under reduced pressure. The obtained residue was purified by silica-gel column chromatography (hexane-ethyl acetate) to give Compound 22 (370 mg, yield 76%).

1H-NMR (CDCl3) δ: 0.92-0.98 (m, 1H), 1.24-1.33 (m, 4H), 1.46 (s, 9H), 1.83-1.90 (m, 1H), 2.73 (q, J=7.6 Hz, 2H), 3.47-3.50 (m, 1H), 3.60-3.94 (m, 3H), 5.67-5.76 (m, 1H).

Step 3 Synthesis of Compound 23

Compound 22 (0.950 g, 3.41 mmol) was dissolved in ethyl acetate (3.8 mL). To the solution was added 4 mol/L hydrochloric acid (ethyl acetate solution, 6.83 mL, 27.3 mmol). The mixture was stirred at room temperature for 7 hours. The solvent was evaporated under reduced pressure. The obtained residue was subjected to SFC chiral preparative separation to give Compound 23 (241 mg, yield 40%) as an optically active compound.

SFC preparative condition
Preparative column (IE-IE-IE, Daicel)
Flow rate: 30 mL/min
Mobile phase: ethanol+0.1% diethylamine 10%
Sample: 25 mg/mL (methanol/chloroform=1/1)
Loading amount: 13 mg
Detection wavelength: 220 nm, Back pressure: 8 Mpa Step 4 Synthesis of Compound 24

Compound 24 was obtained by using Compound 23 instead of Compound 18 in Step 7 of Example 1.

1H-NMR (CDCl3) δ: 0.94-1.10 (m, 5H), 1.26 (t, J=7.2 Hz, 3H), 1.33-1.39 (m, 2H), 1.44-1.49 (m, 10H), 1.70-1.76 (m, 3H), 1.96-1.99 (m, 2H), 2.38-2.48 (m, 3H), 2.67-2.74 (m, 3H), 3.05 (d, J=8.8 Hz, 1H), 3.28 (d, J=8.5 Hz, 1H), 3.36 (br, 1H), 4.35 (s, 1H), 5.65 (br, 1H).

Step 5 Synthesis of Compound 25

Compound 25 was obtained by using Compound 24 instead of Compound 19 in Step 8 of Example 1.

Step 6: Synthesis of Compound I-049

Compound I-049 was obtained by using Compound 25 instead of Compound 20 in Step 9 of Example 1.

1H-NMR (CDCl3) δ: 0.96 (dd, J=8.0, 4.4 Hz, 1H), 1.03-1.29 (m, 8H), 1.36-1.42 (m, 2H), 1.47 (t, J=4.3 Hz, 1H), 1.70-1.81 (m, 3H), 1.99-2.02 (m, 2H), 2.40-2.49 (m, 3H), 2.68-2.74 (m, 6H), 3.06 (d, J=8.7 Hz, 1H), 3.29 (d, J=8.5 Hz, 1H), 3.78-3.88 (m, 1H), 4.51 (s, 2H), 5.65 (s, 1H), 6.25 (d, J=8.3 Hz, 1H), 8.36 (s, 2H).

Reference Example 2 Synthesis of Compound 9

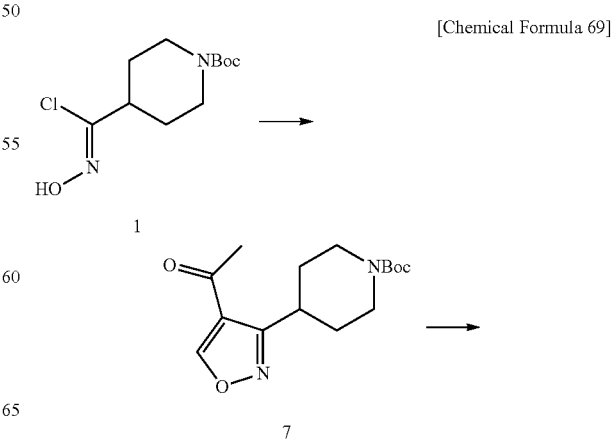

[Chemical Formula 69]

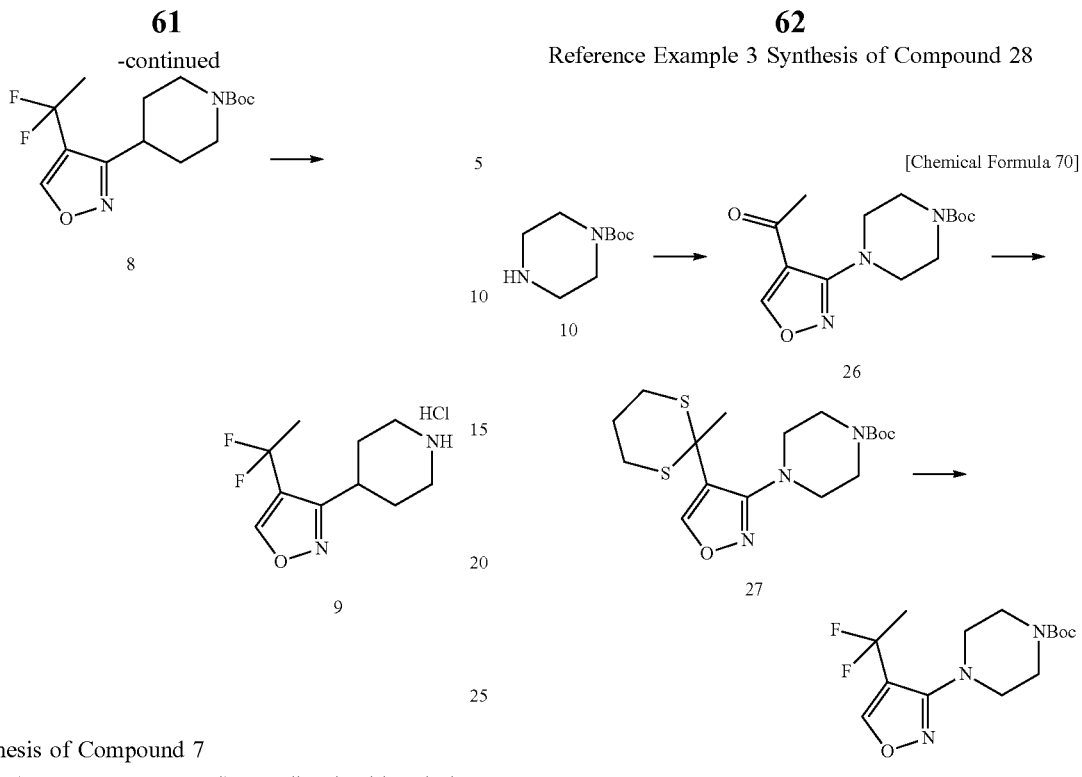

Step 1 Synthesis of Compound 7

Compound 1 (600 mg, 2.284 mmol) was dissolved in ethyl acetate (6.0 mL). To the solution were added 1-dimethyl-amino-but-1-en-3-one (310 mg, 2.74 mmol) and sodium hydrogen carbonate (384 mg, 4.57 mmol). The mixture was stirred at room temperature for 1 hour. To the reaction mixture was added water, and the mixture was extracted with chloroform. The organic layer was separated and then the solvent of the obtained organic layer was evaporated under reduced pressure. The obtained residue was purified by silica-gel column chromatography (hexane-ethyl acetate) to give Compound 7 (596 mg, yield 89%).

1H-NMR (CDCl3) δ: 1.47 (s, 9H), 1.62-1.75 (m, 2H), 1.95-1.99 (m, 2H), 2.49 (s, 3H), 2.86-2.92 (m, 2H), 3.38 (tt, J=11.5, 3.4 Hz, 1H), 4.11-4.23 (brs, 2H), 8.88 (s, 1H).

Step 2 Synthesis of Compound 8

Compound 7 (200 mg, 0.679 mmol) was dissolved in bis(2-methoxyethyl)aminosulfur trifluoride (626 μL, 3.40 mmol). The solution was stirred at 80° C. for 10 hours. To the reaction mixture was added saturated aqueous solution of sodium hydrogen carbonate. The mixture was extracted with chloroform. The organic layer was separated and then the solvent was evaporated under reduced pressure. The obtained residue was purified by silica-gel column chromatography (hexane-ethyl acetate) to give Compound 8 (147 mg. yield 68%).

1H-NMR (CDCl$_3$) δ: 1.47 (s, 9H), 1.74-1.85 (m, 2H), 1.95-2.05 (m, 5H), 2.82-2.88 (m, 2H), 3.01 (tt, J=11.5, 3.5 Hz, 1H), 4.11-4.27 (m, 2H), 8.44 (s, 1H).

Step 3 Synthesis of Compound 9

Compound 8 (147 mg, 0.463 mmol) was dissolved in methanol (2.0 mL). To the solution was added 4 mol/L hydrochloric acid (1,4-dioxane solution, 2.0 mL, 8.0 mmol). The mixture was stirred at room temperature for 1 hour. The solvent was evaporated under reduced pressure to give Compound 9 (102 mg) as a crude product. [M+H] 217.2, method 3, retention time 0.63 min Reference Example 3 Synthesis of Compound 28

[Chemical Formula 70]

Step 1 Synthesis of Compound 26

Compound 10 (918 mg, 4.93 mmol) and DIEA (861 μL, 4.93 mmol) were dissolved in THF (20 mL). To the solution was added 1,1-dibromoformaldoxime (1.0 g, 4.93 mmol) at −20° C. The mixture was stirred for 1.5 hours. 1-Dimethylamino-but-1-en-3-one (2789 mg, 24.65 mmol) and triethylamine (888 μL, 6.41 mmol) were added thereto at 0° C. The mixture was stirred for 1 hour. To the reaction mixture was added water, and the mixture was extracted with ethyl acetate. The organic layer was washed with water and dried over anhydrous sodium sulfate. The solvent was evaporated under reduced pressure. The obtained residue was purified by silica-gel column chromatography (hexane-ethyl acetate) to give Compound 26.

1H-NMR (CDCl3): 1.48 (s, 9H), 2.48 (s, 3H), 3.29-3.32 (m, 4H), 3.56-3.59 (m, 4H), 8.80 (s, 1H).

Step 2 Synthesis of Compound 27

Compound 26 (200 mg, 0.677 mmol) was dissolved in dichloromethane (2.0 mL). To the solution were added 1,3-propanedithiol (103 mg, 0.948 mmol) and boron trifluoride diethyl ether complex (129 μL, 1.016 mmol). The mixture was stirred at 0° C. for 3 hours. 1,3-Propanedithiol (103 mg, 0.948 mmol) and boron trifluoride diethyl ether complex (129 μL, 1.016 mmol) were added thereto. The mixture was stirred at room temperature for 2 hours. To the reaction mixture was added saturated aqueous solution of sodium hydrogen carbonate. The mixture was extracted with chloroform. The organic layer was separated, and then the solvent of the obtained organic layer was evaporated under reduced pressure. The obtained residue was dissolved in chloroform (2.0 mL). To the solution was added Boc$_2$O (0.314 mL, 1.354 mmol). The mixture was stirred at room temperature for 2 hours. The solvent was evaporated under reduced pressure. The obtained residue was purified by silica-gel column chromatography (hexane-ethyl acetate) to give Compound 27 (222 mg, yield 85%).

1H-NMR (CDCl3) δ: 1.48 (s, 9H), 1.97-2.02 (m, 5H), 2.79-2.94 (m, 4H), 3.27-3.29 (m, 4H), 3.51-3.54 (m, 4H), 8.42 (s, 1H).

Step 3 Synthesis of Compound 28

Compound 27 (110 mg, 0.285 mmol) was dissolved in dichloromethane (2 mL). To the solution were added pyridine hydrofluoride complex (70%, 354 μL, 2.85 mmol) and NIS (321 mg, 1.427 mmol) at −78° C. The mixture was stirred for 30 minutes. To the reaction mixture was added saturated aqueous solution of sodium hydrogen carbonate. The mixture was extracted with chloroform. The organic layer was separated, and then the solvent of the obtained organic layer was evaporated under reduced pressure. The obtained residue was dissolved in dichloromethane (2 mL). To the solution was added Boc$_2$O (0.033 mL, 0.143 mmol). The mixture was stirred at room temperature for 30 minutes. The solvent was evaporated under reduced pressure. The obtained residue was purified by silica-gel column chromatography (hexane-ethyl acetate) to give Compound 28 (46 mg, yield 49%).

1H-NMR (CDCl3) δ: 1.48 (s, 9H), 1.98 (t, J=18.2 Hz, 3H), 3.27-3.29 (m, 4H), 3.53-3.55 (m, 4H), 8.34 (a, 1H).

Reference Example 4 Synthesis of Compound 2

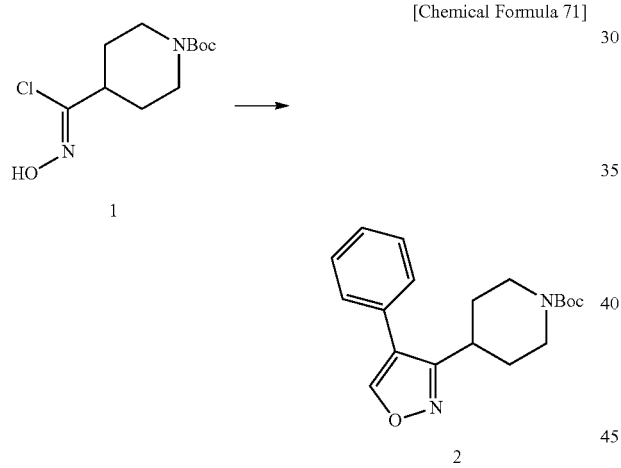

[Chemical Formula 71]

Step 1 Synthesis of Compound 2

Under nitrogen atmosphere, to a solution of Compound 1 (50 mg, 0.190 mmol) in 1,2-dichloroethane (1.0 mL) were added ethynylbenzene (19 μL, 0.173 mmol) and triethylamine (30 μL, 0.216 mmol). The reaction mixture was degassed. Chloro(1,5-cyclooctadiene)(n5-pentamethylcyclopentadienyl)ruthenium(II) (6.57 mg, 0.017 mmol) was added thereto, and the mixture was stirred at room temperature. To the mixture was added water and the mixture was extracted with ethyl acetate. The organic layer was washed with water and brine, and then dried over anhydrous sodium sulfate. The solvent was evaporated under reduced pressure. The obtained residue was purified by silica-gel column chromatography (hexane-ethyl acetate) to give Compound 2 (36 mg, yield 63%).

1H-NMR (CDCl3) δ: 1.45 (s, 9H), 1.71-1.81 (m, 2H), 1.85-1.89 (m, 2H), 2.76-2.83 (m, 2H), 2.96-3.02 (m, 1H), 4.09-4.15 (m, 2H), 7.32-7.34 (m, 2H), 7.37-7.46 (m, 3H), 8.37 (s, 1H).

Example 3 Synthesis of Compound I-026

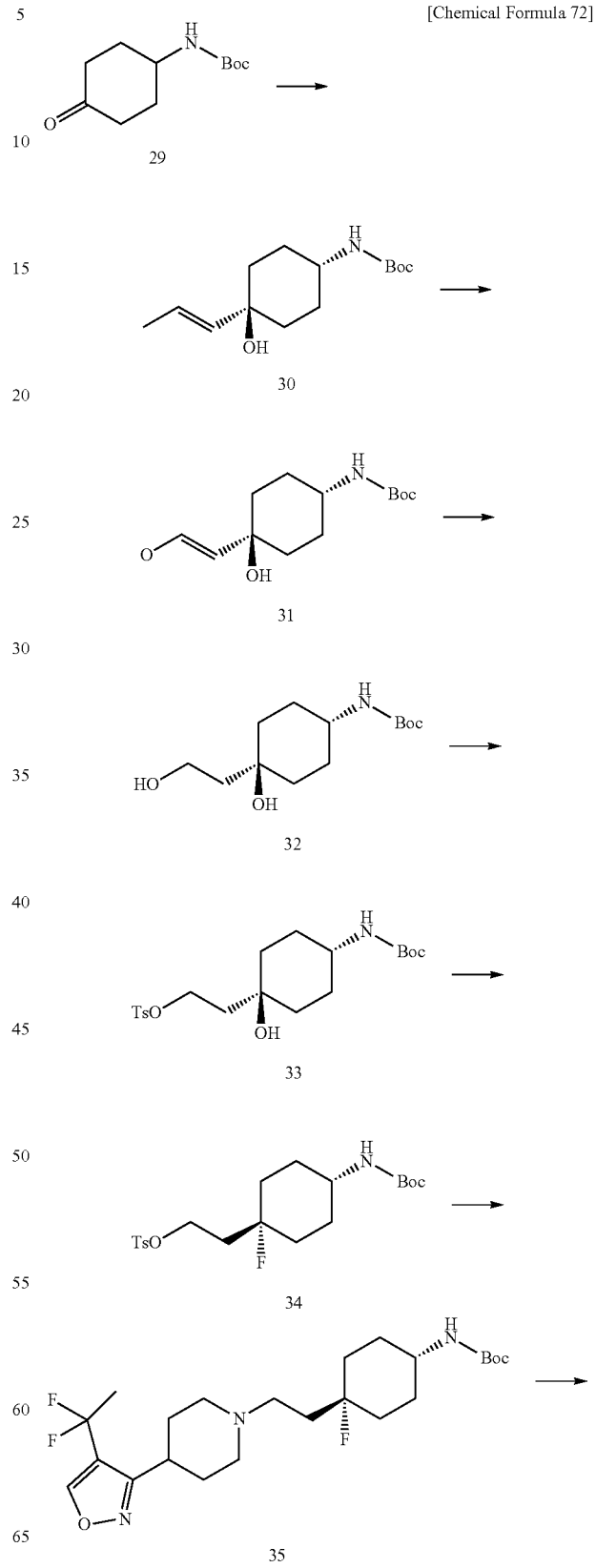

[Chemical Formula 72]

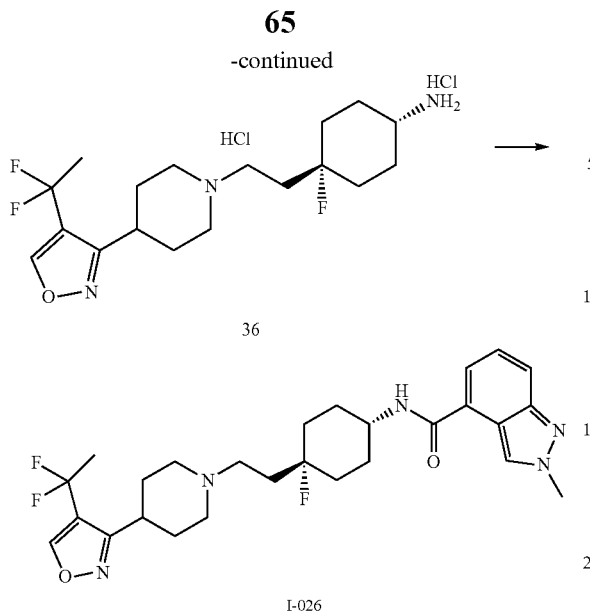

Step 1 Synthesis of Compound 30

Compound 29 (90.0 g, 422.2 mmol) was dissolved in THF (1000 mL). To the solution was added allylmagnesium bromide (1.0 mol/L diethyl ether solution, 1266 mL, 1266 mmol) at −70° C. The mixture was stirred for 1 hour. To the reaction mixture was added ice water. The mixture was extracted with ethyl acetate. The organic layer was washed with water and brine, and then dried over anhydrous sodium sulfate. The solvent was evaporated under reduced pressure. The obtained residue was purified by silica-gel column chromatography (petroleum ether-ethyl acetate) to give Compound 30 (35.0 g, yield 32%).

1H NMR (CDCl3) δ 1.38-1.53 (m, 15H), 1.62-1.64 (m, 1H), 1.91-1.94 (m, 2H), 2.28 (d, J=7.5 Hz, 2H), 3.61 (brs, 1H), 4.51 (brs, 1H), 5.12-5.20 (m, 2H), 5.85-5.90 (m, 1H).

Step 2 Synthesis of Compound 31

Compound 30 (35.0 g, 137.2 mmol) was dissolved in THF (500 mL) and water (500 mL). To the solution were added potassium osmate (VI) dihydrate (5.05 g, 13.72 mmol) and sodium periodate (117.34 g, 548.63 mmol) at 0° C. The mixture was stirred at room temperature for 8 hours. To the reaction mixture were added water and aqueous solution of sodium thiosulfate. The mixture was extracted with ethyl acetate. The organic layer was washed with water and brine, and then dried over anhydrous sodium sulfate. The solvent was evaporated under reduced pressure to give Compound 31 (35.0 g) as a crude product.

Step 3 Synthesis of Compound 32

Compound 31 (15.0 g, 58.33 mmol) was dissolved in THF (150 mL) and methanol (150 m). To the solution was added sodium borohydride (4.41 g, 116.66 mmol) portionwise at 0° C. The mixture was stirred at 0° C. for 1 hour. To the reaction mixture was added saturated aqueous solution of ammonium chloride. The mixture was extracted with ethyl acetate. The organic layer was washed with brine, and then dried over anhydrous sodium sulfate. The solvent was evaporated under reduced pressure to give a compound 32 (12.0 g) as a crude product.

Step 4 Synthesis of Compound 33

Compound 32 (713 mg, 2.75 mmol) was dissolved in dichloromethane (7.4 mL). To the solution were added 4-dimethylaminopyridine (33.6 mg, 0.275 mmol), triethylamine (0.762 mL, 5.50 mmol) and p-toluenesulfonyl chloride (577 mg, 3.02 mmol) at 0° C. The mixture was stirred at 0° C. for 4 hours. To the reaction mixture was added 0.1 mol/L hydrochloric acid. The mixture was extracted with ethyl acetate. The organic layer was washed with saturated aqueous solution of sodium bicarbonate, water, and brine, and then dried over anhydrous sodium sulfate. The solvent was evaporated under reduced pressure. The obtained residue was purified by silica-gel column chromatography (hexane-ethyl acetate) to give Compound 33 (761 mg. yield 67%).

1H-NMR (CDCl3) δ: 1.29-1.38 (m, 3H), 1.43-1.50 (m, 11H), 1.57-1.66 (m, 2H), 1.86-1.93 (m, 4H), 2.46 (s, 3H), 3.57 (brs, 1H), 4.22 (t, J=6.7 Hz, 2H), 4.46 (brs, 1H), 7.36 (d, J=8.0 Hz, 2H), 7.79 (d, J=8.3 Hz, 2H).

Step 5 Synthesis of Compound 34

Compound 33 (759 mg, 1.83 mmol) was dissolved in dichloromethane (30.4 mL). To the solution was added diethylaminosulfur trifluoride (1.45 mL, 11.0 mmol) at −78° C. The mixture was stirred at −78° C. for 40 minutes. To the reaction mixture was added water. The mixture was extracted with ethyl acetate. The organic layer was washed with water and brine, and then dried over anhydrous sodium sulfate. The solvent was evaporated under reduced pressure. The obtained residue was purified by silica-gel column chromatography (hexane-ethyl acetate) to give Compound 34 (345 mg, yield 45%).

1H-NMR (CDCl3) δ: 1.36-1.48 (m, 13H), 1.80-1.99 (m, 6H), 2.46 (s, 3H), 3.40 (brs, 1H), 4.17 (t, J=6.7 Hz, 2H), 4.38 (brs, 1H), 7.35 (d. J=8.0 Hz, 2H), 7.79 (d, J=8.3 Hz, 2H).

Step 6 Synthesis of Compound 35

Compound 9 (150 mg, 0.594 mmol) was suspended in acetonitrile (1.5 mL). To the suspension were added potassium carbonate (164 mg, 1.187 mmol), DIEA (207 μL, 1.187 mmol) and Compound 34 (247 mg, 0.594 mmol). The mixture was stirred at 70° C. for 4.5 hours. To the mixture was added water and the mixture was extracted with ethyl acetate. The organic layer was dried over anhydrous sodium sulfate. The solvent was evaporated under reduced pressure. The obtained residue was purified by silica-gel column chromatography (hexane-ethyl acetate) to give Compound 35 (205 mg, yield 75%).

1H-NMR (CDCl3) δ: 1.41-1.56 (m, 13H), 1.76-2.10 (m, 15H), 2.47-2.51 (m, 2H), 2.79-2.87 (m, 1H), 3.00-3.03 (m, 2H), 3.40-3.48 (m, 1H), 4.42 (d, J=7.2 Hz, 1H), 8.43 (t, J=1.6 Hz, 1H).

Step 7 Synthesis of Compound 36

Compound 36 was obtained by using Compound 35 instead of Compound 19 in Step 8 of Example 1.

Step 8 Synthesis of Compound I-026

Compound I-026 was obtained by using Compound 36 instead of Compound 20 and using 2-methylindazole-4-carboxylic acid instead of Compound 6 in Step 9 of Example 1.

1H-NMR (DMSO-d6): 1.51-2.09 (m, 19H), 2.41-2.45 (m, 2H), 2.77-2.85 (m, 1H), 2.95-2.98 (m, 2H), 3.82-3.91 (m, 1H), 4.19 (s, 3H), 7.28 (dd, J=8.5, 7.0 Hz, 1H), 7.56 (d, J=6.8 Hz, 1H), 7.74 (d, J=8.5 Hz, 1H), 8.28 (d, J=8.0 Hz, 1H), 8.56 (s, 1H), 9.28 (t, J=1.8 Hz, 1H).

The following compounds were synthesized in similar manners as described above. In the tables, RT represents LC/MS retention time (min). In the following tables, regarding stereo-information, the stereostructures of the compounds were determined as described in the structural formulas. If there are no specific descriptions of stereo-information, it indicates the compounds are racemates.

TABLE 1

| Compound No. | Structure | LC/MS method | RT (min) | MS (m/z) |
|---|---|---|---|---|
| I-001 | 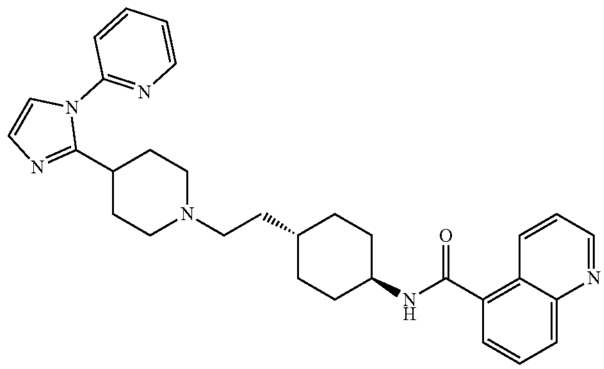 [SMILES: O=C(N[C@H]1CC[C@H](CCN2CCC(c3nccn3-c3ccccn3)CC2)CC1)c1cccc2ncccc12] | 3 | 0.69 | 509 |
| I-002 | 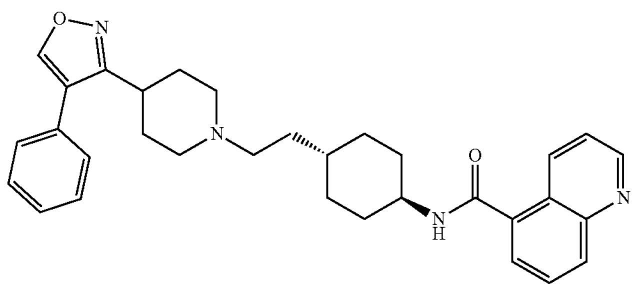 [SMILES: O=C(N[C@H]1CC[C@H](CCN2CCC(c3nocc3-c3ccccc3)CC2)CC1)c1cccc2ncccc12] | 3 | 1.17 | 509 |
| I-003 | 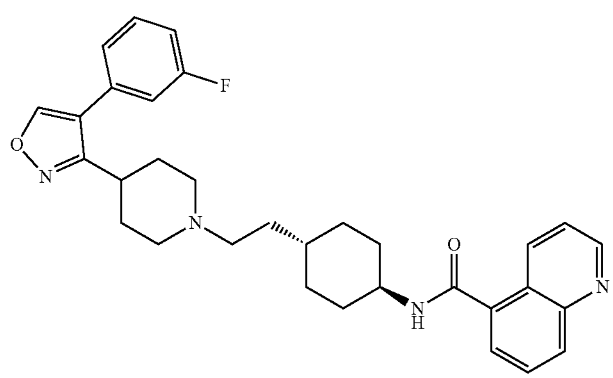 [SMILES: O=C(N[C@H]1CC[C@H](CCN2CCC(c3nocc3-c3cccc(F)c3)CC2)CC1)c1cccc2ncccc12] | 3 | 1.2 | 527 |
| I-004 | 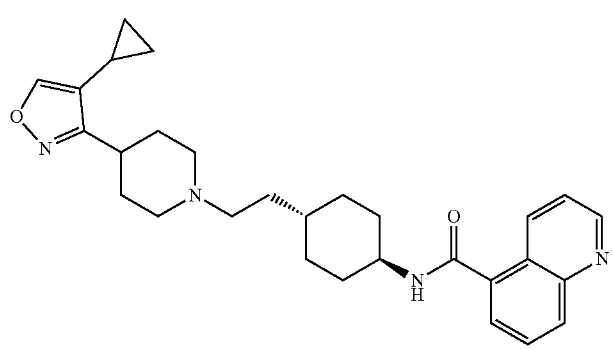 [SMILES: O=C(N[C@H]1CC[C@H](CCN2CCC(c3nocc3C3CC3)CC2)CC1)c1cccc2ncccc12] | 3 | 0.99 | 473 |

TABLE 1-continued

| Compound No. | Structure | LC/MS method | RT (min) | MS (m/z) |
|---|---|---|---|---|
| I-005 | 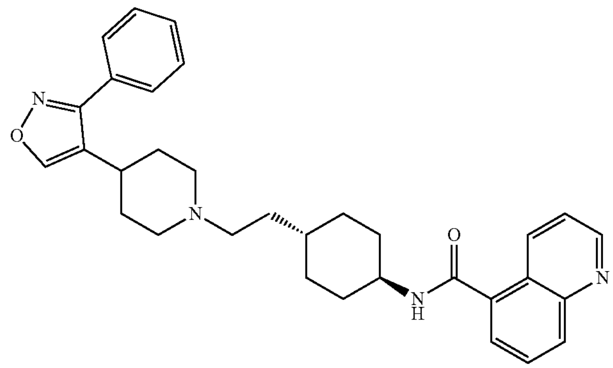 [SMILES: O=C(N[C@H]1CC[C@H](CCN2CCC(c3conc3-c3ccccc3)CC2)CC1)c1cccc2ncccc12] | 3 | 1.1 | 509 |
| I-006 | 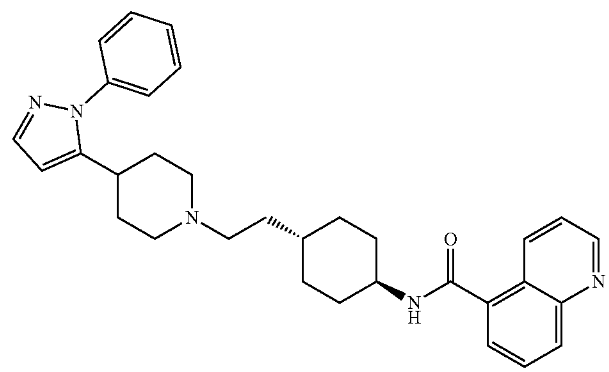 [SMILES: O=C(N[C@H]1CC[C@H](CCN2CCC(c3ccnn3-c3ccccc3)CC2)CC1)c1cccc2ncccc12] | 3 | 0.99 | 508 |

TABLE 2

| | | | | |
|---|---|---|---|---|
| I-007 | | 3 | 1.12 | 508 |
| I-008 | | 3 | 1.11 | 465.35 |

TABLE 2-continued
| ID | Structure | | | |
|---|---|---|---|---|
| I-009 | 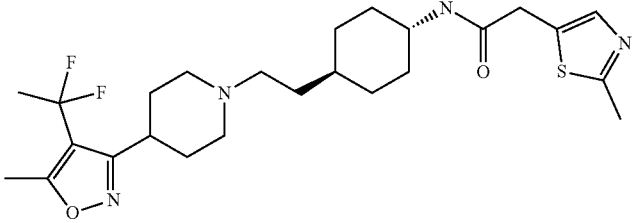 | 4 | 1.37 | 248.2 |
| I-010 | 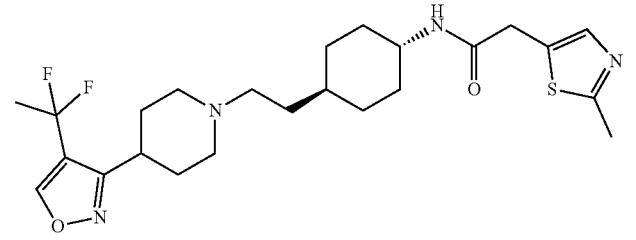 | 3 | 1.06 | 481.35 |
| I-011 | 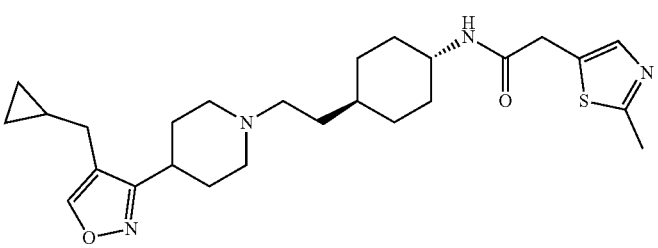 [SMILES: Cc1ncc(CC(=O)N[C@H]2CC[C@H](CCN3CCC(c4nocc4CC4CC4)CC3)CC2)s1] | 3 | 1.18 | 471.35 |
| I-012 | 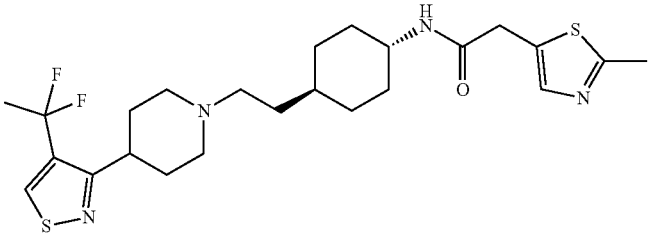 [SMILES: Cc1ncc(CC(=O)N[C@H]2CC[C@H](CCN3CCC(c4nscc4C(C)(F)F)CC3)CC2)s1] | 2 | 1.33 | 497 |
| I-013 | 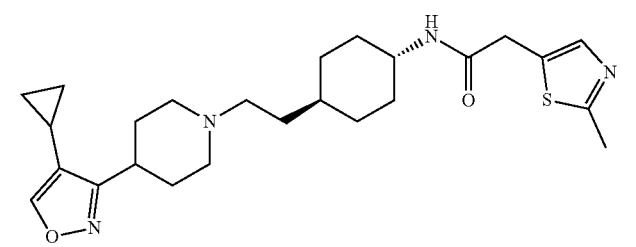 [SMILES: Cc1ncc(CC(=O)N[C@H]2CC[C@H](CCN3CCC(c4nocc4C4CC4)CC3)CC2)s1] | 3 | 1.1 | 457.35 |
| I-014 | 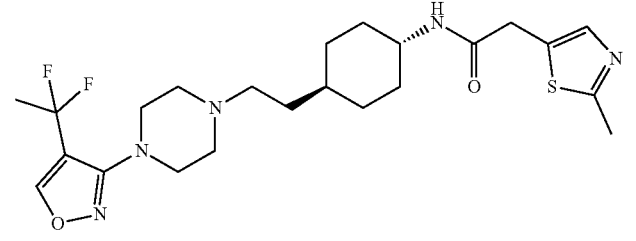 | 3 | 1.03 | 482.3 |

TABLE 3
| | | | | |
|---|---|---|---|---|
| I-015 | 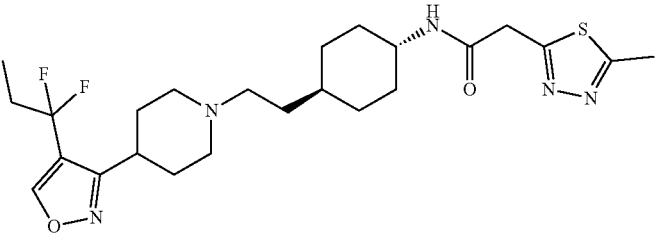 [SMILES: CCC(F)(F)c1conc1C1CCN(CC[C@H]2CC[C@H](NC(=O)Cc3nnc(C)s3)CC2)CC1] | 3 | 1.19 | 496.35 |
| I-016 | 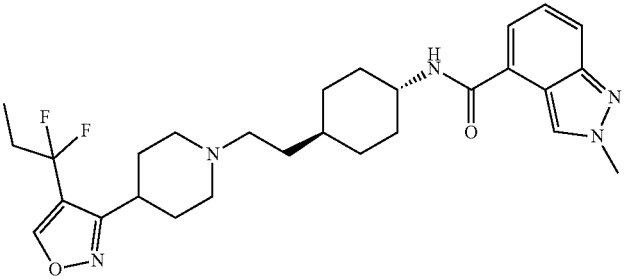 [SMILES: CCC(F)(F)c1conc1C1CCN(CC[C@H]2CC[C@H](NC(=O)c3cccc4nn(C)cc34)CC2)CC1] | 3 | 1.33 | 514.4 |
| I-017 | 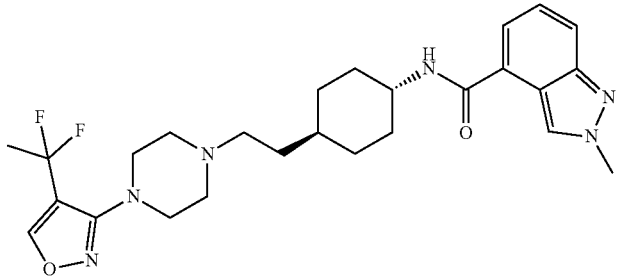 [SMILES: Cn1cc2c(C(=O)N[C@H]3CC[C@H](CCN4CCN(c5nocc5C(C)(F)F)CC4)CC3)cccc2n1] | 3 | 1.18 | 501.35 |
| I-018 | 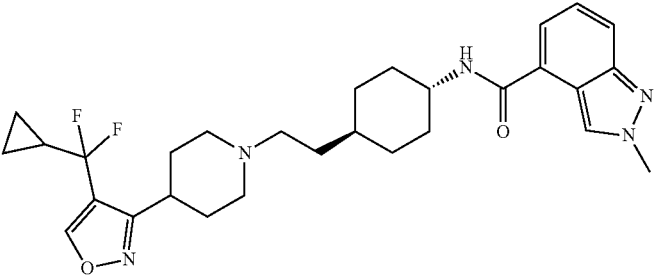 [SMILES: Cn1cc2c(C(=O)N[C@H]3CC[C@H](CCN4CCC(c5nocc5C(F)(F)C5CC5)CC4)CC3)cccc2n1] | 3 | 1.4 | 526.35 |
| I-019 | 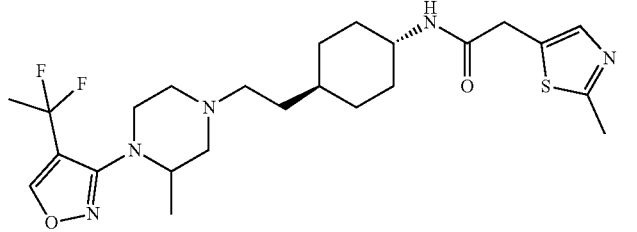 [SMILES: Cc1ncc(CC(=O)N[C@H]2CC[C@H](CCN3CCN(c4nocc4C(C)(F)F)C(C)C3)CC2)s1] | 3 | 1.17 | 496.35 |
| I-020 | 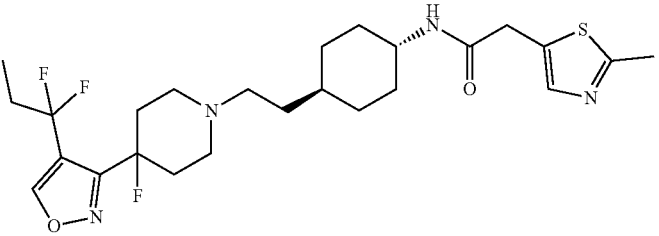 [SMILES: CCC(F)(F)c1conc1C1(F)CCN(CC[C@H]2CC[C@H](NC(=O)Cc3cnc(C)s3)CC2)CC1] | 3 | 1.33 | 513.35 |

TABLE 3-continued
I-021     2   1.44   512
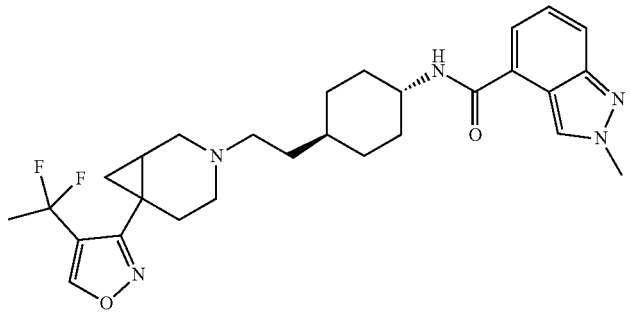 [SMILES: Cn1cc2c(C(=O)N[C@H]3CC[C@H](CCN4CCC5(c6nocc6C(C)(F)F)CC5C4)CC3)cccc2n1]
TABLE 4
I-022     2   1.42   500
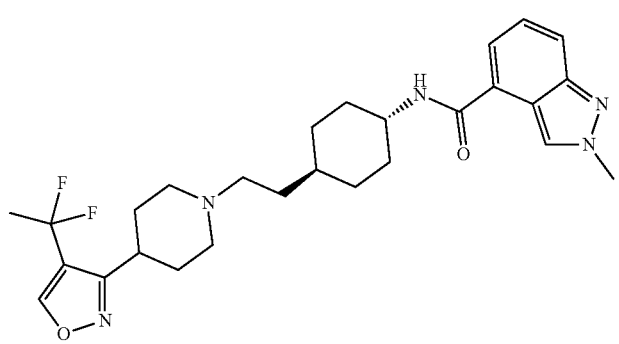 [SMILES: Cn1cc2c(C(=O)N[C@H]3CC[C@H](CCN4CCC(c5nocc5C(C)(F)F)CC4)CC3)cccc2n1]
I-023     2   1.13   476
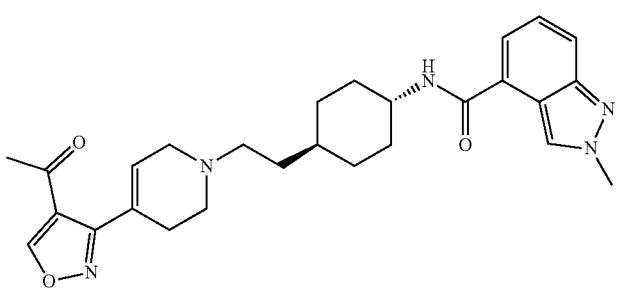 [SMILES: CC(=O)c1conc1C1=CCN(CC[C@H]2CC[C@H](NC(=O)c3cccc4nn(C)cc34)CC2)CC1]
I-024     2   1.4   498
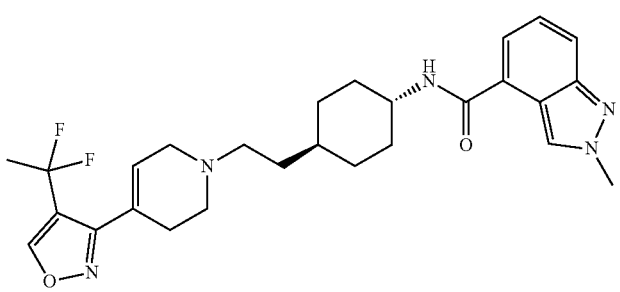 [SMILES: Cn1cc2c(C(=O)N[C@H]3CC[C@H](CCN4CC=C(c5nocc5C(C)(F)F)CC4)CC3)cccc2n1]

TABLE 4-continued
I-025     2   1.55   512
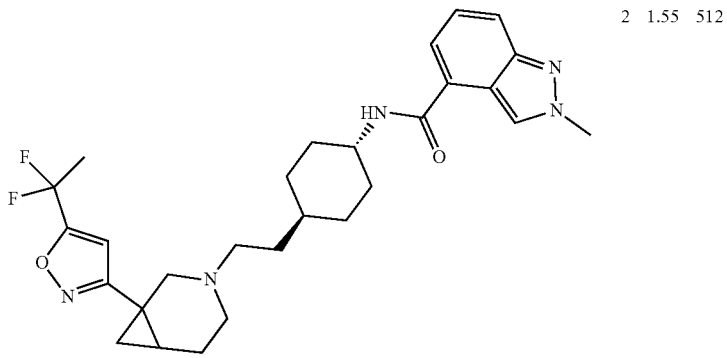
I-026     2   1.43   518
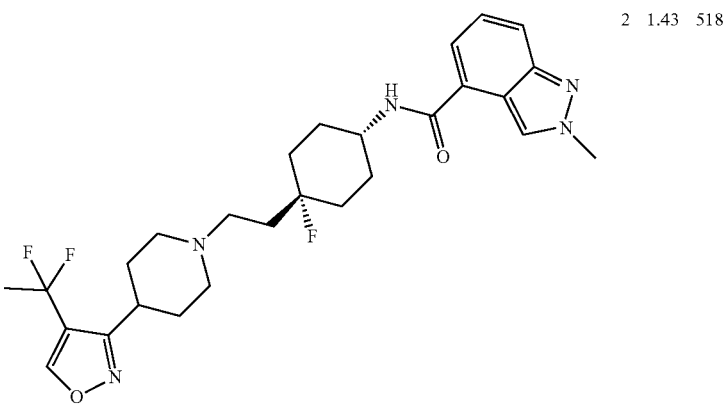
I-027     2   1.45   498
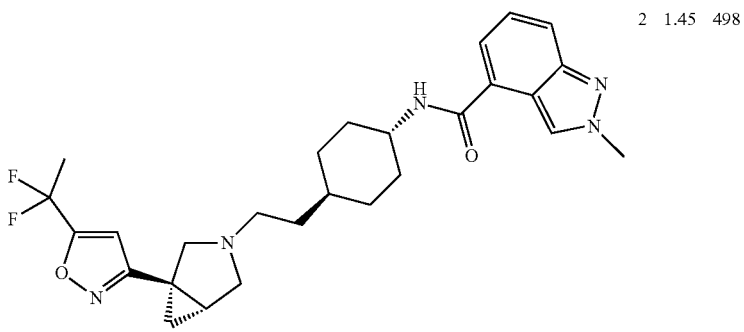
TABLE 5
I-028     2   1.28   466
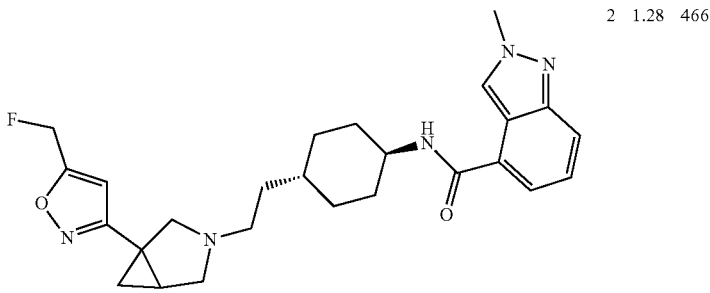

TABLE 5-continued
I-029 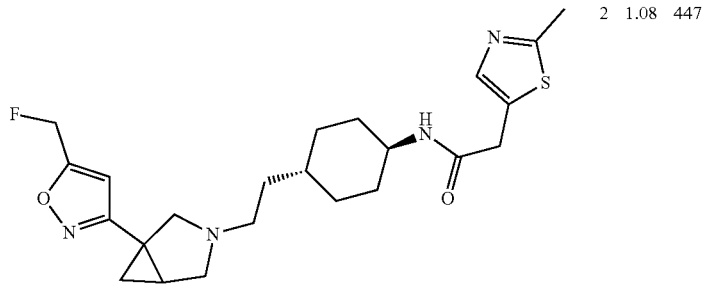 2 1.08 447
I-030 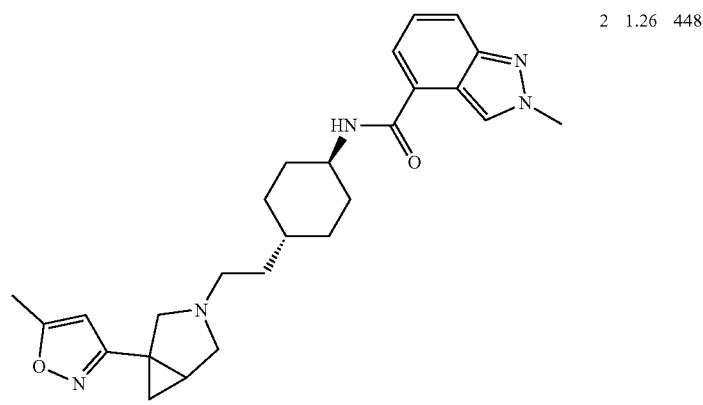 2 1.26 448
I-031 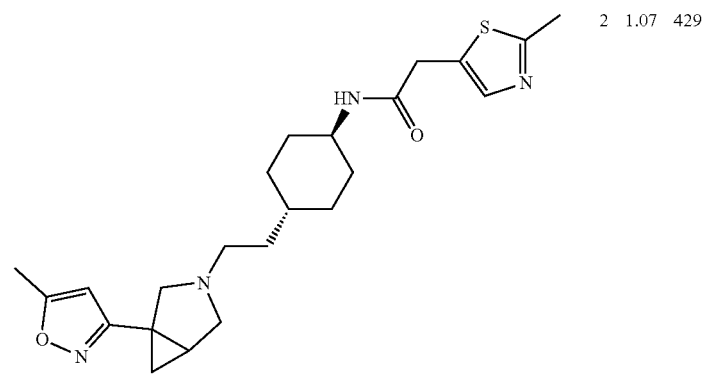 2 1.07 429
I-032 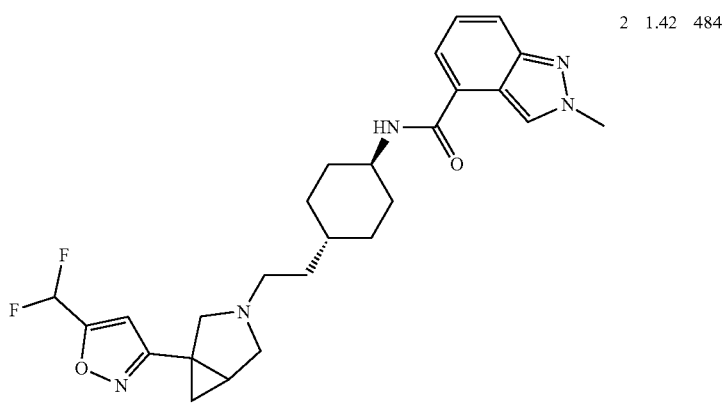 2 1.42 484

TABLE 5-continued
| I-033 | 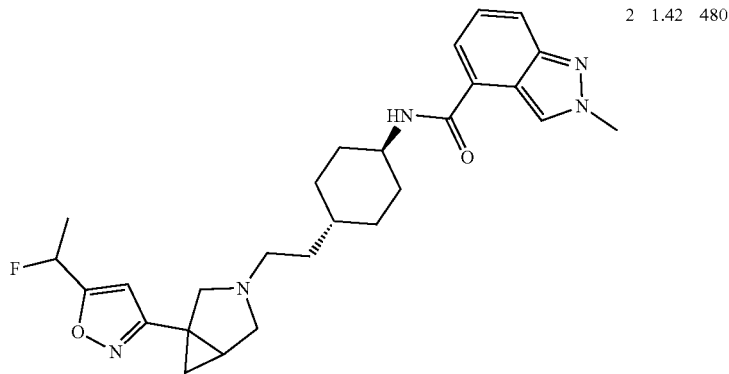 | 2 1.42 480 |
TABLE 6
| I-034 | 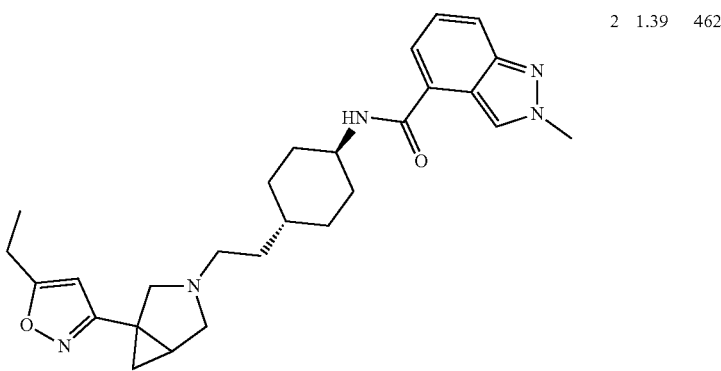 | 2 1.39 462 |
| I-035 | 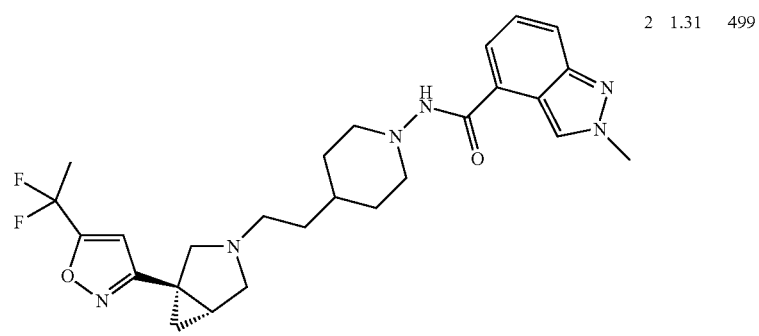 | 2 1.31 499 |
| I-036 | 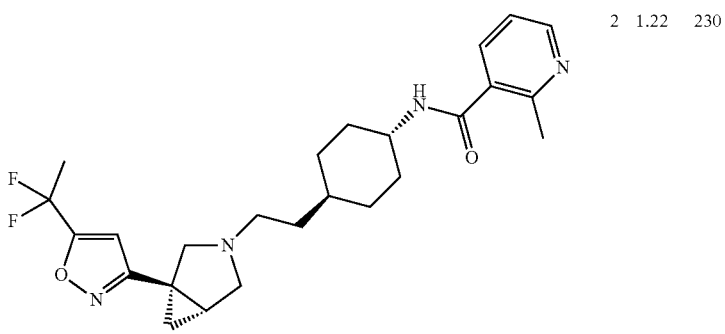 | 2 1.22 230 |

TABLE 6-continued
| I-037 | 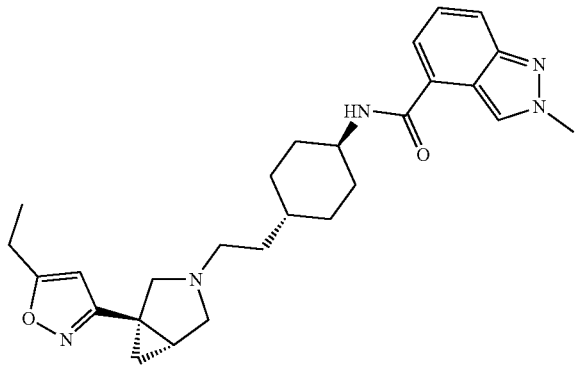 [SMILES: CCc1cc([C@]23C[C@H]2CN(CC[C@H]2CC[C@H](NC(=O)c4cccc5nn(C)cc45)CC2)C3)no1] | 2 | 1.33 | 462 |
| I-038 | 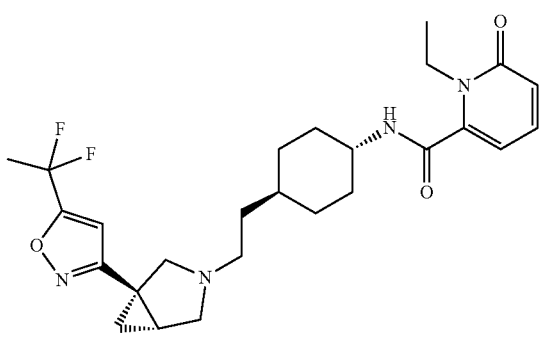 [SMILES: CCn1c(C(=O)N[C@H]2CC[C@H](CCN3C[C@@H]4C[C@]4(c4cc(C(C)(F)F)on4)C3)CC2)cccc1=O] | 2 | 1.35 | 489.3 |
| I-039 | 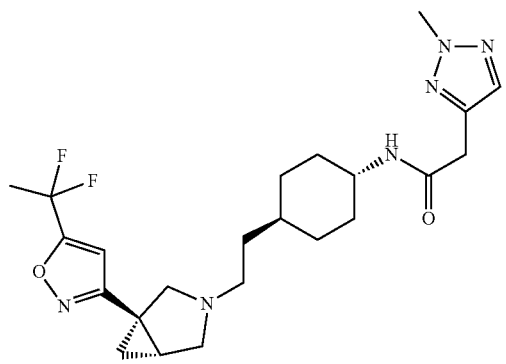 [SMILES: Cn1ncc(CC(=O)N[C@H]2CC[C@H](CCN3C[C@@H]4C[C@]4(c4cc(C(C)(F)F)on4)C3)CC2)n1] | 2 | 1.33 | 463.2 |
TABLE 7
| I-040 | 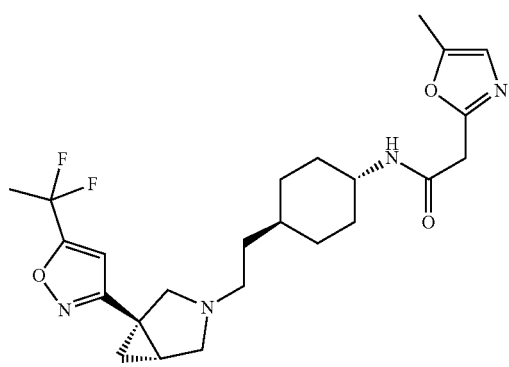 [SMILES: Cc1cnc(CC(=O)N[C@H]2CC[C@H](CCN3C[C@@H]4C[C@]4(c4cc(C(C)(F)F)on4)C3)CC2)o1] | 2 | 1.4 | 463.2 |

I-041 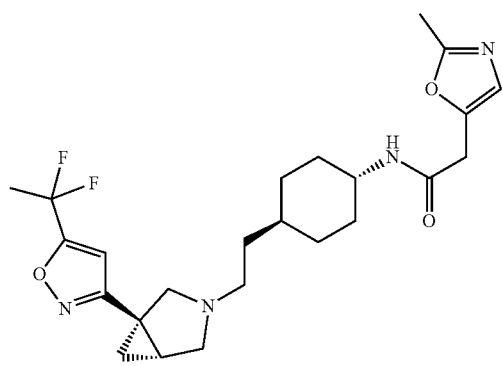 [SMILES: Cc1ncc(CC(=O)N[C@H]2CC[C@H](CCN3C[C@@H]4C[C@]4(c4cc(C(C)(F)F)on4)C3)CC2)o1] 2 1.34 463.2
I-042 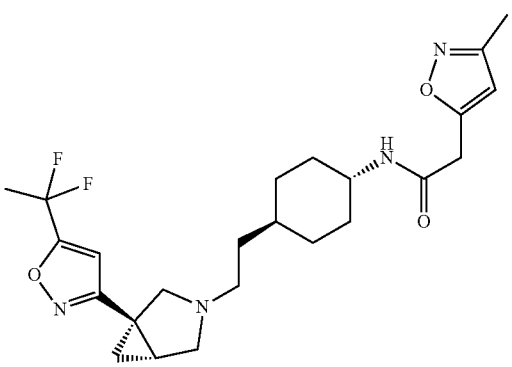 [SMILES: Cc1cc(CC(=O)N[C@H]2CC[C@H](CCN3C[C@@H]4C[C@]4(c4cc(C(C)(F)F)on4)C3)CC2)on1] 2 1.42 463.2
I-043 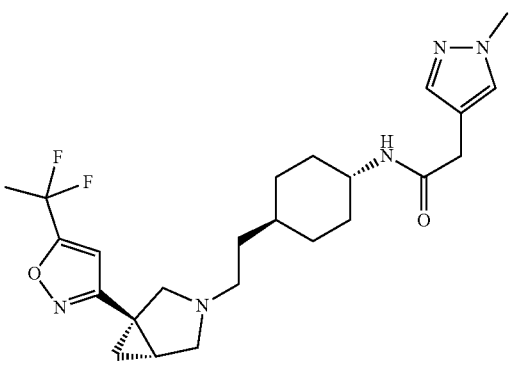 [SMILES: Cn1cc(CC(=O)N[C@H]2CC[C@H](CCN3C[C@@H]4C[C@]4(c4cc(C(C)(F)F)on4)C3)CC2)cn1] 2 1.32 462.3
I-044 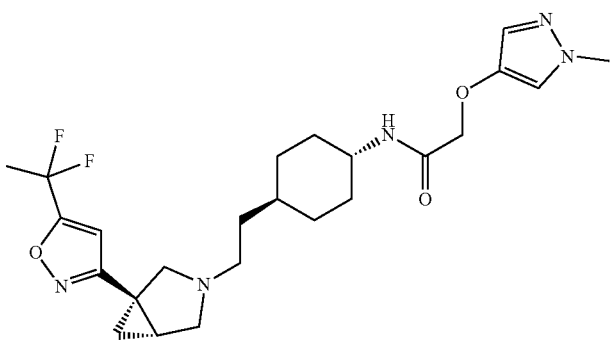 [SMILES: Cn1cc(OCC(=O)N[C@H]2CC[C@H](CCN3C[C@@H]4C[C@]4(c4cc(C(C)(F)F)on4)C3)CC2)cn1] 2 1.35 478.3

TABLE 7-continued
| | | | | |
|---|---|---|---|---|
| I-045 | 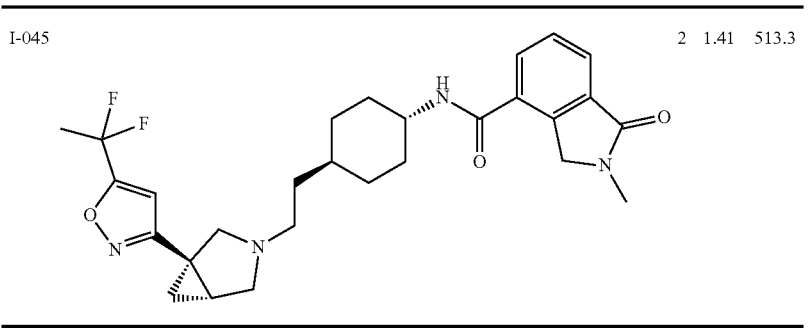 | 2 | 1.41 | 513.3 |
TABLE 8
| | | | | |
|---|---|---|---|---|
| I-046 | 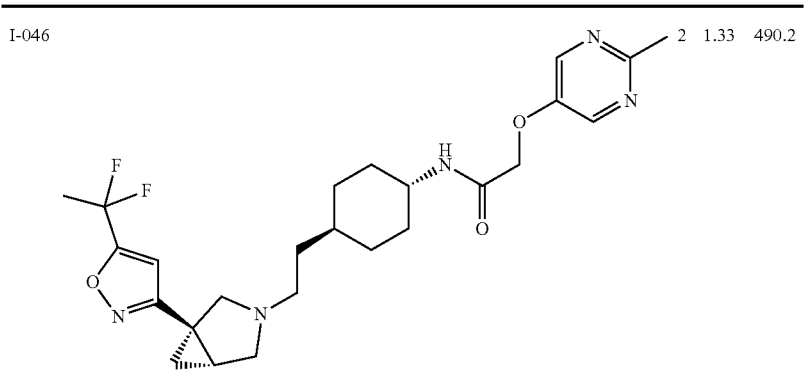 | 2 | 1.33 | 490.2 |
| I-047 | 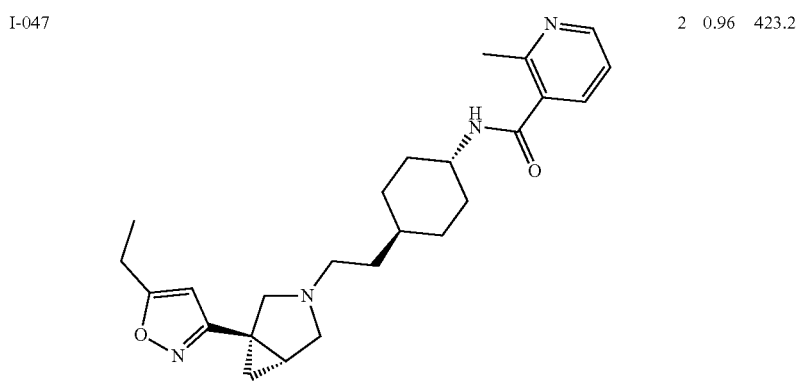 | 2 | 0.96 | 423.2 |
| I-048 | 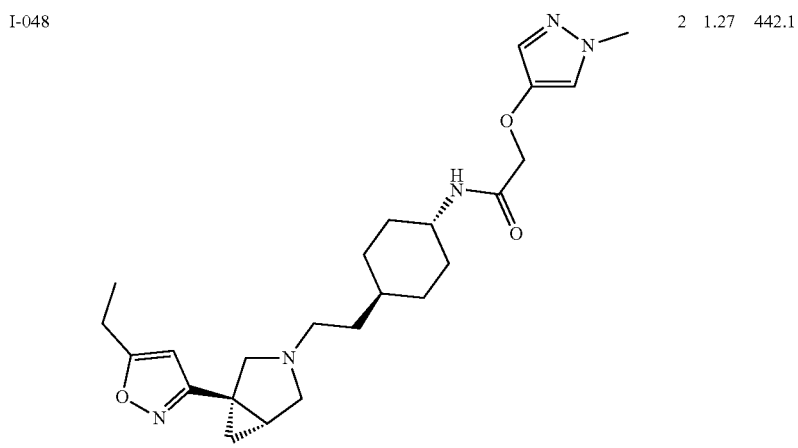 | 2 | 1.27 | 442.1 |

TABLE 8-continued
| I-049 | 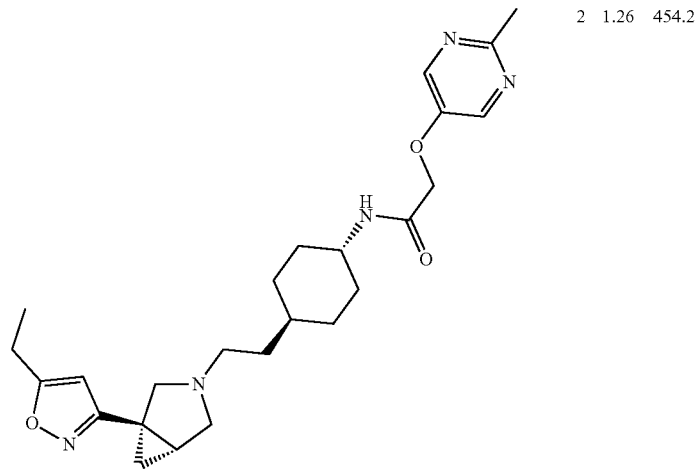 | 2 | 1.26 | 454.2 |
| I-050 | 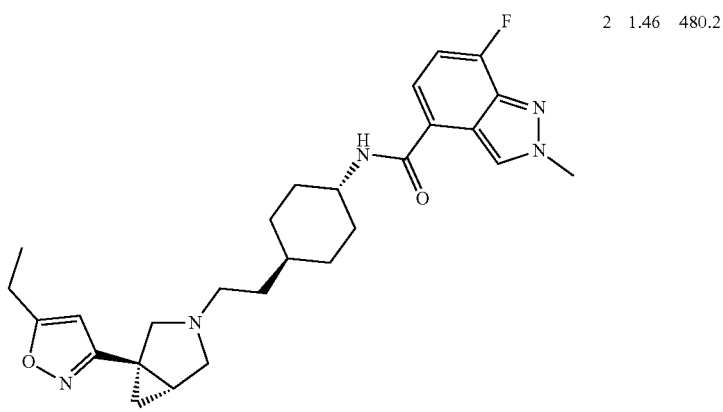 | 2 | 1.46 | 480.2 |
TABLE 9
| I-051 | 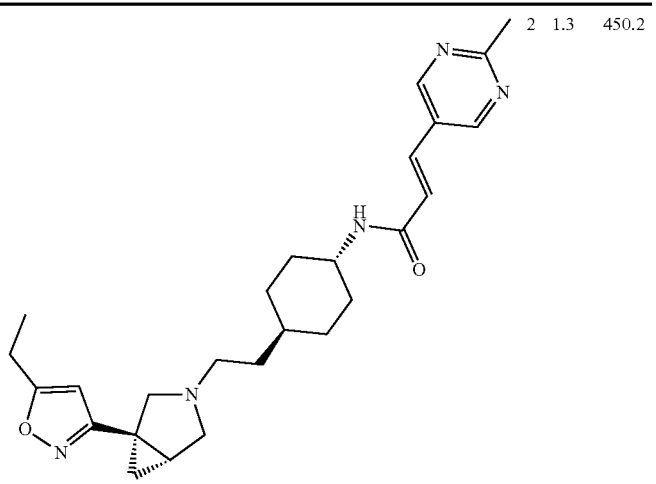 | 2 | 1.3 | 450.2 |

TABLE 9-continued
I-052 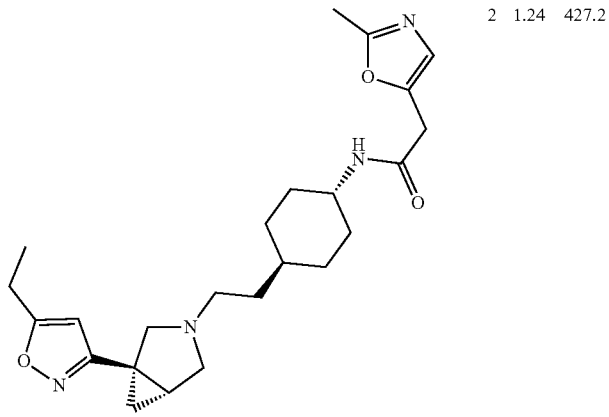 2 1.24 427.2
I-053 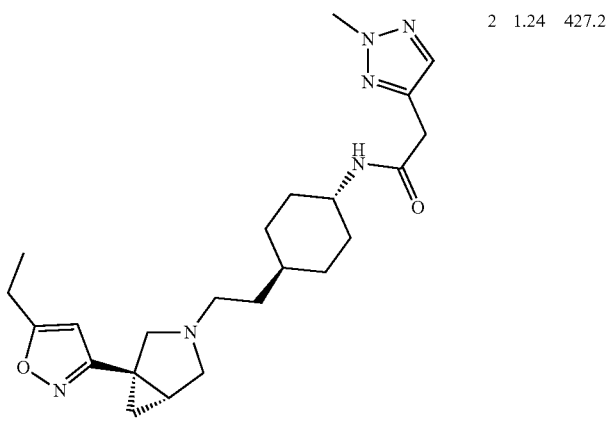 2 1.24 427.2
I-054 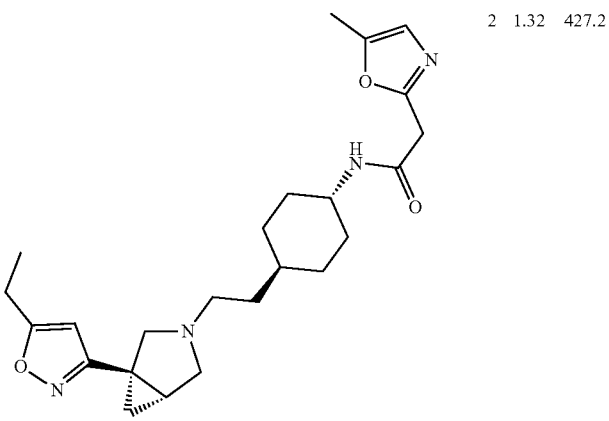 2 1.32 427.2

TABLE 9-continued
| I-055 | 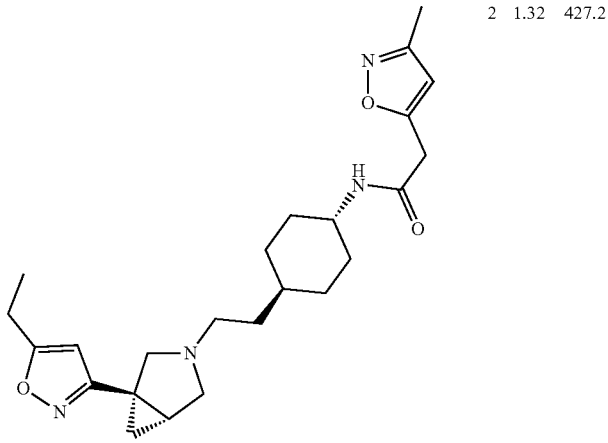 | 2 | 1.32 | 427.2 |
TABLE 10
| I-056 | 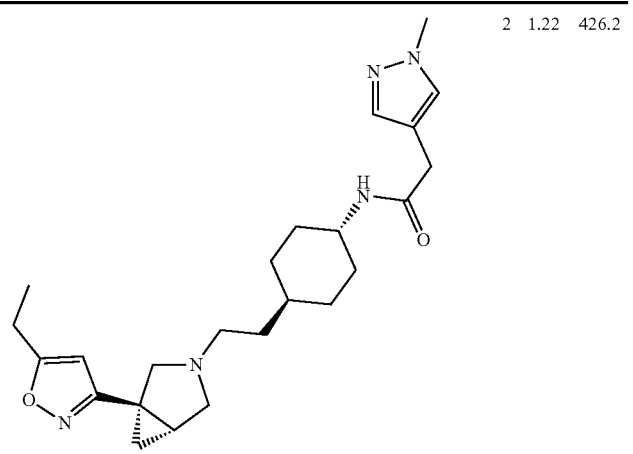 | 2 | 1.22 | 426.2 |
| I-057 | 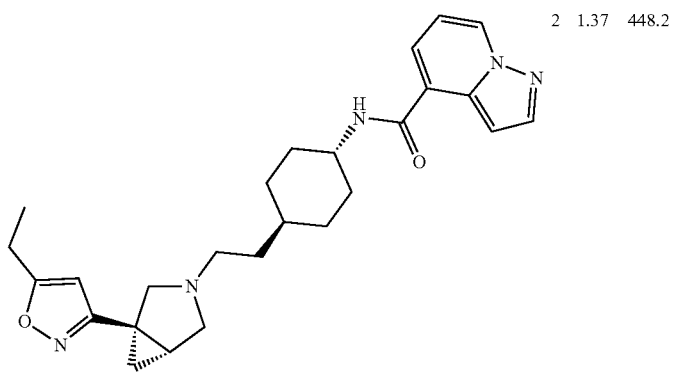 | 2 | 1.37 | 448.2 |

TABLE 10-continued

| Compound No. | Structure | LC-MS method | RT (min) | MS (m/z) |
|---|---|---|---|---|
| I-058 | 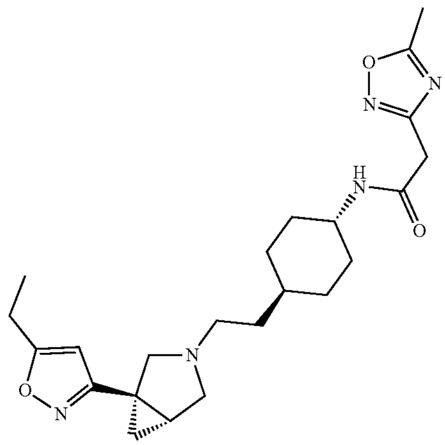 [SMILES: CCc1cc([C@]23C[C@H]2CN(CC[C@H]2CC[C@H](NC(=O)Cc4noc(C)n4)CC2)C3)no1] | 2 | 1.25 | 428.2 |
| I-059 | 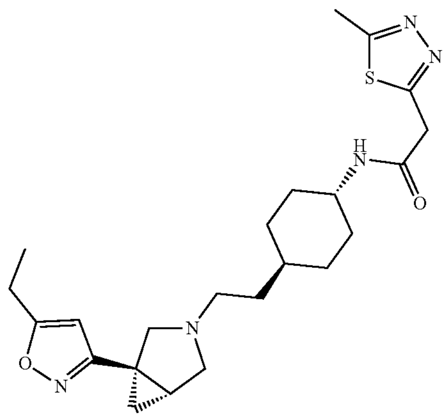 [SMILES: CCc1cc([C@]23C[C@H]2CN(CC[C@H]2CC[C@H](NC(=O)Cc4nnc(C)s4)CC2)C3)no1] | 2 | 1.25 | 444.1 |

TABLE 11

| Compound No. | Structure | LC-MS method | RT (min) | MS (m/z) |
|---|---|---|---|---|
| II-1 | 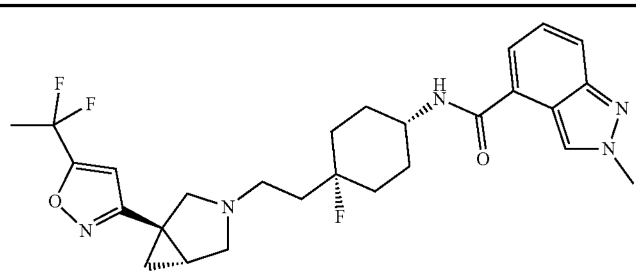 | 2 | 1.48 | 516.2 |
| II-2 | 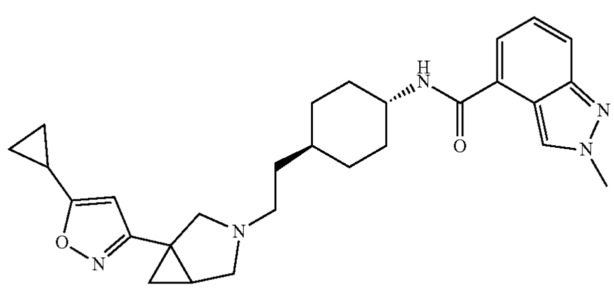 [SMILES: Cn1cc2c(C(=O)N[C@H]3CC[C@H](CCN4CC5CC5(c5cc(C6CC6)on5)C4)CC3)cccc2n1] | 2 | 1.5 | 474 |

TABLE 11-continued

| Compound No. | Structure | LC-MS method | RT (min) | MS (m/z) |
|---|---|---|---|---|
| II-3 | 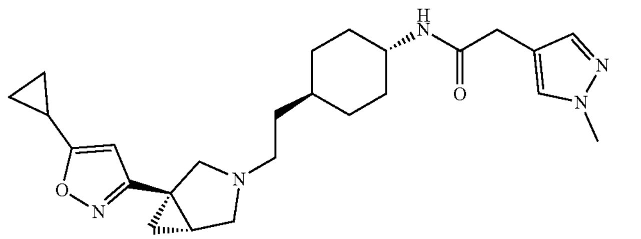 [SMILES: Cn1cc(CC(=O)N[C@H]2CC[C@H](CCN3C[C@@H]4C[C@]4(c4cc(C5CC5)on4)C3)CC2)cn1] | 2 | 1.23 | 438.3 |
| II-4 | 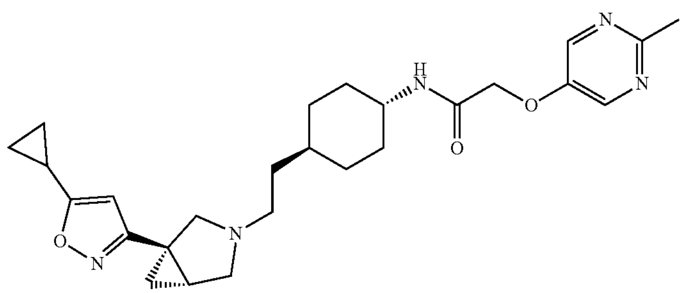 [SMILES: Cc1ncc(OCC(=O)N[C@H]2CC[C@H](CCN3C[C@@H]4C[C@]4(c4cc(C5CC5)on4)C3)CC2)cn1] | 2 | 1.26 | 466.3 |
| II-5 | 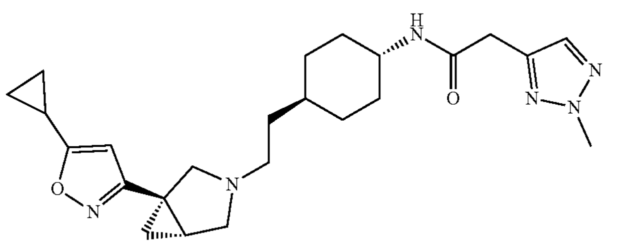 [SMILES: Cn1ncc(CC(=O)N[C@H]2CC[C@H](CCN3C[C@@H]4C[C@]4(c4cc(C5CC5)on4)C3)CC2)n1] | 2 | 1.25 | 439.3 |

Test examples for the compounds of the present invention are described below.

Test Example 1: Test of Binding Inhibition for Dopamine D3 Receptor (Experimental Conditions)

Cell membranes: Jump-In HEK cell membranes expressing human recombinant D3 receptor (4 μg/well)

Buffer solution: 50 mM Tris-HCl (35409-45, Nacalai Tesque) (pH 7.4) containing 120 mM NaCl (31320-05, Nacalai Tesque), 1 mM $MgCl_2 \cdot 6H_2O$ (20909-55, Nacalai Tesque), 5 mM KCl (28514-75, Nacalai Tesque) and 2 mM $CaCl_2$ (067-31, NAKARAI CHEMICALS, LTD.)

Radioligand: (final concentration) 2 nM [$^3$H]-Methylspiperone ([$^3$H—N-methyl-]-Methylspiperone, NET-856, 83.8 Ci/mmol, PerkinElmer)

Non-specific ligand: (final concentration) 10 μM Butaclamol [(+)-Butaclamol Hydrochloride, D033, Sigma]

SPA beads solution: SPA beads [WGA PVT SPA Scintillation Beads, RPNQ0001 (500 mg), RPNQ0060 (2 g), PerkinElmer] (0.2 mg/well)

Incubation time and temperature: 120 min at 25° C.

Kd: 0.321 nM (Preparation of Non-Specific Ligand and the Compounds of the Present Invention)

Butaclamol or the compounds of the present invention were weighed and DMSO was added to make a 10 mM solution. This solution was diluted to each concentration.

(Preparation of Radioligand Solution)

[$^3$H]-Methylspiperone was weighed and the buffer solution was added to make a 6 nM solution.

(Preparation of SPA Beads Solution)

SPA beads were weighed and stirred in water to make a 50 mg/mL solution. Using this solution, a mixture with the cell membranes was prepared.

(Binding Assay of the Compounds of the Present Invention)

225 nL of the solutions of the non-specific ligand or the compounds of the present invention at each concentration (in case of vehicle, final concentration 0.3% DMSO) were added in each well of a 384-well white/clear bottom microplate (3706, Corning). Jump-In HEK Cell membranes (final reaction amount: 4 μg protein/well), the SPA beads solution (final reaction amount: 0.2 mg/well) and the buffer solution were mixed and the mixed solution was left still for 1 hour or more at 4° C. Then, 50 μL of the mixture was added to each well of the plate. In addition, 25 μL of 6 nM [$^3$H]-Methylspiperone (final concentration: 2 nM) was added to each well. The plate was sealed by putting TopSeal-A 96/384 well (6050185, PerkinElmer, Inc.) on the top of the plate, mixed using stirring deaerator (Well Tornado, FK-62, Sakaki-elc.) and incubated for 120 min at 25° C. After incubation, the radioactivity of [$^3$H]-Methylspiperone which was bonded to D3 receptor was determined by liquid scintillation counter (1450 Microbeta, PerkinElmer) in each well. Non-specific binding was calculated based on the radioactivity of [$^3$H]-Methylspiperone in the presence of 10 μM non-labeled Butaclamol. The total binding was calculated using the radioactivity of [$^3$H]-Methylspiperone in the absence of the compounds of the present invention (vehicle). The Ki values were calculated from dose-response curves.

Binding activities of the compounds of the present invention were calculated from the following Binding Inhibition Rate (%):

Inhibition Rate(%)=[1−(c−a)/(b−a)]×100 a: Average cpm of non-specific binding
b: Average cpm of total binding
c: Cpm in the presence of each test compound The test results of the compounds of the present invention are shown in the following tables.

TABLE 12

| Compound No. | hD3_Ki (nM) |
| --- | --- |
| I-001 | 3.3 |
| I-002 | 0.12 |
| I-003 | 0.093 |
| I-004 | 0.6 |
| I-005 | 1.2 |
| I-006 | 4 |
| I-007 | 2.7 |
| I-008 | 0.69 |
| I-009 | 1.9 |
| I-010 | 0.65 |
| I-011 | 0.63 |
| I-012 | 1.9 |
| I-013 | 0.95 |
| I-014 | 0.2 |
| I-015 | 0.13 |
| I-016 | 0.085 |
| I-017 | 0.21 |
| I-018 | 0.22 |
| I-019 | 0.15 |
| I-020 | 0.37 |
| I-021 | 4.8 |
| I-022 | 0.11 |
| I-023 | 0.69 |
| I-024 | 0.082 |
| I-025 | 2.4 |
| I-026 | 0.55 |
| I-027 | 0.3 |
| I-028 | 1.9 |
| I-029 | 2.2 |
| I-030 | 2.9 |
| I-031 | 3.8 |
| I-032 | 0.4 |
| I-033 | 0.77 |
| I-034 | 0.71 |
| I-035 | 0.24 |
| I-036 | 0.25 |
| I-037 | 0.7 |
| I-038 | 0.073 |
| I-039 | 0.39 |
| I-040 | 0.56 |
| I-041 | 0.28 |
| I-042 | 0.061 |
| I-043 | 0.45 |
| I-044 | 0.83 |
| I-045 | 0.13 |
| I-046 | 0.2 |
| I-047 | 1.4 |
| I-048 | 0.71 |
| I-049 | 0.44 |
| I-050 | 0.42 |
| I-051 | 0.3 |
| I-052 | 0.58 |
| I-053 | 0.48 |
| I-054 | 1.2 |
| I-055 | 0.23 |
| I-056 | 0.62 |
| I-057 | 0.47 |
| I-058 | 1.3 |
| I-059 | 0.77 |

TABLE 13

| Compound No. | hD3_Ki (nM) |
| --- | --- |
| II-1 | 0.42 |
| II-2 | 0.2 |
| II-3 | 0.36 |
| II-4 | 0.45 |
| II-5 | 0.71 |

Test Example 2: Test of Binding Inhibition for Dopamine D2 Receptor (Experimental Conditions)

Cell membranes: Jump-In HEK cell membranes expressing human recombinant D2 receptor (2 µg/well)

Buffer solution: 50 mM Tris-HCl (35409-45, Nacalai Tesque) (pH 7.4) containing 120 mM NaCl (31320-05, Nacalai Tesque), 1 mM $MgCl_2 \cdot 6H_2O$ (20909-55, Nacalai Tesque), 5 mM KCl (28514-75, Nacalai Tesque) and 2 mM $CaCl_2$ (067-31, NAKARAI CHEMICALS, LTD.)

Radioligand: (final concentration) 1.2 nM [$^3$H]-Methylspiperone ([$^3$H—N-methyl-]-Methylspiperone, NET-856, 83.8 Ci/mmol, PerkinElmer)

Non-specific ligand: (final concentration) 10 µM Butaclamol [(+)-Butaclamol Hydrochloride, D033; Sigma]

SPA beads solution: SPA beads [WGA PVT SPA Scintillation Beads, RPNQ0001 (500 mg), RPNQ0060 (2 g), PerkinElmer] (0.2 mg/well)

Incubation time and temperature: 120 min at 25° C.

Kd: 0.272 nM (Preparation of Non-Specific Ligand and the Compounds of the Present Invention)

Butaclamol or the compounds of the present invention were weighed and DMSO was added to make a 10 mM solution. This solution was diluted to each concentration.

(Preparation of Radioligand Solution)

[$^3$H]-Methylspiperone was weighed and the buffer solution was added to make a 3.6 nM solution.

(Preparation of SPA Beads Solution)

SPA beads were weighed and stirred in water to make a 50 mg/mL solution. Using this solution, a mixture with the cell membranes was prepared.

(Binding Assay of the Compounds of the Present Invention)

225 nL of the solutions of the non-specific ligand or the compounds of the present invention at each concentration (in case of vehicle, final concentration 0.3% DMSO) were added in each well of a 384-well white/clear bottom microplate (3706, Corning). Jump-In HEK Cell membranes (final reaction amount: 2 µg protein/well), the SPA bead solution (final reaction amount: 0.2 mg/well) and the buffer solution were mixed and the mixed solution was left still for 1 hour or more at 4° C. Then, 50 µL of the mixture was added to each well of the plate. In addition, 25 µL of 3.6 nM [$^3$H]-Methylspiperone (final concentration: 1.2 nM) was added to each well. The plate was sealed by putting TopSeal-A 96/384 well (6050185, PerkinElmer) on the top of the plate, mixed using stirring deaerator (Well Tornado, FK-62, Sakaki-elc.) and incubated for 120 min at 25° C. After incubation, the radioactivity of [$^3$H]-Methylspiperone which was bonded to D2 receptor was determined by liquid scintillation counter (1450 Microbeta, PerkinElmer) in each well. Non-specific binding was calculated based on the radioactivity of [$^3$H]-Methylspiperone in the presence of 10 µM non-labeled Butaclamol. The total binding was calculated using the radioactivity of [³H]-Methylspiperone in the absence of the compounds of the present invention (vehicle). The Ki values were calculated from dose-response curves.

Binding activities of the compounds of the present invention were calculated from the following Binding Inhibition Rate (%):

Inhibition Rate(%)=[1−(c−a)/(b−a)]×100 a: Average cpm of non-specific binding
b: Average cpm of total binding
c: Cpm in the presence of each test compound The test results of the compounds of the present invention are shown in the following table.

TABLE 14

| Compound No. | hD2_Ki (nM) |
|---|---|
| I-001 | >1700 |
| I-002 | 32 |
| I-003 | 36 |
| I-004 | 160 |
| I-005 | 860 |
| I-006 | 1100 |
| I-007 | >1800 |
| I-008 | 350 |
| I-009 | 330 |
| I-010 | 230 |
| I-011 | 380 |
| I-012 | 460 |
| I-013 | 230 |
| I-014 | 88 |
| I-015 | 67 |
| I-016 | 33 |
| I-017 | 52 |
| I-018 | 45 |
| I-019 | 68 |
| I-020 | 310 |
| I-021 | 1700 |
| I-022 | 170 |
| I-023 | 1700 |
| I-024 | 220 |
| I-025 | 1200 |
| I-026 | 250 |
| I-027 | >1800 |
| I-028 | 550 |
| I-029 | 1100 |
| I-030 | >1800 |
| I-031 | >1800 |
| I-032 | 200 |
| I-033 | 550 |
| I-034 | 730 |
| I-035 | 870 |
| I-036 | 190 |
| I-037 | 290 |
| I-038 | 91 |
| I-039 | 300 |
| I-040 | 350 |
| I-041 | 240 |
| I-042 | 1300 |
| I-043 | 270 |
| I-044 | 220 |
| I-045 | 86 |
| I-046 | 330 |
| I-047 | 530 |
| I-048 | 550 |
| I-049 | 830 |
| I-050 | 200 |
| I-051 | 380 |
| I-052 | 920 |
| I-053 | 1100 |
| I-054 | 780 |
| I-055 | 850 |
| I-056 | 1000 |
| I-057 | 230 |
| I-058 | 790 |
| I-059 | 550 |

TABLE 15

| Compound No. | hD2_Ki (nM) |
|---|---|
| II-1 | >2300 |
| II-2 | 380 |
| II-3 | 730 |
| II-4 | 730 |
| II-5 | 860 |

Test Example 3: Effect of Suppressing Impulsivity in Rat

Male Crl: WI rats are obtained at post-natal day 14 and weaning is occurred at post-natal day 21. Starting from then, the rats are housed 2-3 per cage and food-restricted (Day 1). The feeding amount is 5 g/day at post-natal day 21-28 (Day 1-8), 8.5 g/day at post-natal day 29-32 (Day 9-12), and 10 g/day at post-natal day 33-36 (Day 13-16), preventing their body weight from being 60% or less of the weight of the free feeding rats.

Four days after the beginning of the food restriction (Day 5), pellets are put on goal boxes located in the left-side and the right-side of T-maze. Then, the rats are allowed to freely explore the T-maze box for 5 min to get habituated to the T-maze box and learn that the pellets are put on the goal boxes located in the left-side and the right-side. For 4 consecutive days from the next day (Day 6-9), one pellet (20 mg×1) is put in one side of the goal box as a small reward, and 5 pellets (20 mg×5) are put in the other side of the goal box as a large reward, and the rats are trained to learn their positions. Each rat undergoes 10-trial per day trainings. The rats that did not select the large reward more than or equal to 9 times of the 10 trials in the 4 days trainings are given additional training until they select the large reward more than or equal to 9 times of the 10 trials. The evaluations of the drug efficacy are started on Day 12. The compounds of the present invention are dissolved in 0.5% methylcellulose (WAKO) and administered p.o. to the trained rats to attain the dose of 1, 3 or 10 mg/kg. Vehicle control group is administered 0.5% methylcellulose. The administering tests are conducted with 6-8 rats in each group. The administrations are conducted daily over 5 days from Day 12-16. After 60 min from the administration, it is tested whether which of large reward and small reward is selected. When the rat selects the arm leading to the large reward, the rat is shut for 15 seconds in the arm to introduce delay before the rat is allowed to access to the reward. In the arm leading to the small reward, the door is opened immediately and no delay is introduced. These tests are conducted over 5 days from Day 12-16, 10 trials per day. The numbers of choices of the large reward during total 50 trials of 5 days are compared between the vehicle control group and the group which is treated with the compounds of the present invention.

Test Example 4: Rat Dopamine D3/D2 Receptor Occupancy

Five-week-old male Crl WI rats are housed in groups of 4-5 rats after arrival and allowed free access to food and water.

Occupancy is measured by autoradiography with [³H]-(+)-4-propyl-9-hydroxynaphthoxazine ([³H]-(+)-PHNO), a selective radiolabeled ligand for dopamine D3/D2 receptors, at 6 weeks of age (the week following arrival). The compound of the present invention is dissolved in 0.5% methylcellulose. The mixture is orally administered to rats at the dose of 0.3, 1, or 3 mg/kg (the dosage varies for each compound). Vehicle control group is administered 0.5% methylcellulose. The occupancy tests are conducted with 3-4 rats in each group. After a certain time from the oral administration of the compound of the present invention, [$^3$H]-PHNO is administered intravenously. At 30 minutes after the intravenous administration of [$^3$H]-(+)-PHNO, blood collection is performed from the abdominal postcaval vein under isoflurane anesthesia using a syringe treated with heparin. The collected blood is centrifuged to obtain plasma. The rat is sacrificed by decapitation immediately after blood collection, and whole brain is removed, then immediately frozen on dry ice. Frozen brain sections (20 μm each in thickness) are prepared by cryostat. The frozen brain sections are dried thoroughly and exposed to imaging plate for 3H-labeled compound for approximately two weeks. After the exposure, autoradiograms are obtained by scanning the imaging plates with an image analyzer. The regions of interest are set on the striatum, cerebellum, and cerebellar lobes 9 & 10 on each autoradiogram with image analysis software to analyze radioactivity concentrations in each region.

D3 receptor occupancy is calculated as follows, with Cerebellar lobes 9 & 10 as the target region.

Receptor occupancy(%)=[($a-b$)/$a$]×100 a; specific binding ratio of the vehicle control group (mean value)
b; specific binding ratio of the administration group of the compound of the present invention Each specific binding ratio is calculated as follows.

Specific binding ratio=($c-d$)/$d$ c; radioactivity concentrations in Cerebellar lobes 9 & 10
d; radioactivity concentration in cerebellum, a non-specific binding region The D2 receptor occupancy can be calculated in similar manners as described above, using striatum as the target region. Plasma can also be used in the measurement of drug concentrations in plasma at LC/MS/MS.

Test Example 5 CYP Inhibition Test

Using commercially available pooled human liver microsomes, an inhibitory degree of each metabolite production amount by the compound of the present invention is assessed as marker reactions of human main five CYP isoforms (CYP1A2, 2C9, 2C19, 2D6, and 3A4), 7-ethoxyresorufin O-deethylation (CYP1A2), tolbutamide methylhydroxylation (CYP2C9), mephenytoin 4'-hydroxylation (CYP2C19), dextromethorphan O-demethylation (CYP2D6), and terfenedine hydroxylation (CYP3A4).

The reaction conditions are as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenidine (CYP3A4); reaction time, 15 minutes; reaction temperature, 37° C.; enzyme, pooled human liver microsome 0.2 mg protein/mL; concentration of the compound of the present invention, 1, 5, 10, 20 μmol/L (four points).

Each five kinds of substrates, human liver microsomes, and the compound of the present invention in 50 mmol/L Hepes buffer are added as reaction solutions to a 96-well plate at the composition as described above, and NADPH, as a cofactor, is added to initiate the marker metabolism reactions. After the incubation at 37° C. for 15 minutes, a methanol/acetonitrile=1/1 (V/V) solution is added to stop the reaction. After the centrifugation at 3000 rpm for 15 minutes, resorufin (CYP1A2 metabolite) in the supernatant is quantified by a fluorescent multilabel counter or LC/MS/MS and hydroxytolbutamide (CYP2C9 metabolite), 4' hydroxymephenytoin (CYP2C19 metabolite), dextrorphan (CYP2D6 metabolite), and terfenadine alcohol metabolite (CYP3A4 metabolite) are quantified by LC/MS/MS.

The sample adding only DMSO which is a solvent of the compound of the present invention to a reaction system is adopted as a control (100%). Remaining activity (%) is calculated at each concentration of the compound of the present invention compared to the control, and $IC_{50}$ is calculated by reverse presumption by a logistic model using a concentration and an inhibition rate.

Test Example 6: BA Test

Materials and Methods for experiments to evaluate oral absorption
(1) Animals: The SD rats are used
(2) Breeding conditions: The SD rats are allowed to freely take solid food and sterilized tap water.
(3) Dose and grouping: orally or intravenously administered at a predetermined dose. Grouping is set as follows. (Dose can be changed depends on the compound)
Oral administration: 1 mg/kg or 2 μmol/kg (n=2)
Intravenous administration: 0.5 mg/kg or 1 μmol/kg (n=2)
(4) Preparation of dosing solution: for oral administration, in a solution or a suspension state using 0.5% methylcellulose solution or dimethyl sulfoxide/0.5% methylcellulose solution=¼ solution; for intravenous administration, in a solubilized state using dimethylacetamide/propylene glycol=1/1 or dimethyl sulfoxide/propylene glycol=1/1 solvent.
(5) Administration method: in oral administration, forcedly administer into ventriculus with oral probe; in intravenous administration, administer from caudal vein with a needle-equipped syringe.
(6) Evaluation item: blood is collected over time, and the concentration of the compound of the present invention in plasma is measured by LC/MS/MS.
(7) Statistical analysis: regarding the transition of the plasma concentration of the compound of the present invention, the area under the plasma concentration-time curve (AUC) is calculated by non-linear least squares program WinNonlin (registered trademark), and the bioavailability (BA) of the compound of the present invention is calculated from the AUCs of the oral administration group and the intravenous administration group.

Test Example 7: Metabolism Stability Test

Using commercially available pooled human liver microsomes, the compound of the present invention is reacted for a constant time, a remaining rate is calculated by comparing a reacted sample and an unreacted sample, thereby, a degree of metabolism in liver is assessed.

A reaction is performed (oxidative reaction) at 37° C. for 0 minutes or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution is added to 100 μL of a solution of methanol/acetonitrile=1/1 (v/v), mixed and centrifuged at 3000 rpm for 15 minutes. The compound of the present invention in the supernatant is quantified by LC/MS/MS or Solid-Phase Extraction (SPE)/MS, and a remaining amount of the compound of the present invention after the reaction is calculated, letting a compound amount at 0 minute reaction time to be 100%.

Test Example 8: CYP3A4 (MDZ) MBI Test

CYP3A4(MDZ) MBI test is a test of investigating Mechanism based inhibition (MBI) potential on CYP3A4 by the enhancement of inhibitory degree of a metabolic reaction caused by the compound of the present invention. CYP3A4 inhibition is evaluated using pooled human liver microsomes by 1-hydroxylation reaction of midazolam (MDZ) as a marker reaction.

The reaction conditions are as follows: substrate, 10 µmol/L MDZ; pre-reaction time, 0 or 30 minutes; reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention at pre-reaction time, 1, 5, 10, 20 µmol/L (four points).

Pooled human liver microsomes and a solution of the compound of the present invention in 100 mmol/L K-Pi buffer (pH 7.4) as a pre-reaction solution are added to a 96-well plate at the composition of the pre-reaction. A part of pre-reaction solution is transferred to another 96-well plate, and 1/10 diluted by 100 mmol/L K-Pi buffer containing a substrate. NADPH as a co-factor is added to initiate a reaction as a marker reaction (without preincubation). After a predetermined time of a reaction, methanol/acetonitrile=1/1 (V/V) solution is added to stop the reaction. In addition, NADPH is added to a remaining pre-reaction solution to initiate a pre-reaction (with preincubation). After a predetermined time of a pre-reaction, a part is transferred to another well plate, and 1/10 diluted by K-Pi buffer containing a substrate to initiate a reaction as a marker reaction. After a predetermined time of a reaction, a solution of methanol/acetonitrile=1/1 (V/V) is added to stop the reaction. Each plate where the index reaction has been performed is centrifuged at 3000 rpm for 15 minutes. Then, 1-hydroxymidazolam in the centrifugation supernatants is quantified by LC/MS/MS.

The sample adding only DMSO which is a solvent of the compound of the present invention to a reaction system is adopted as a control (100%). Remaining activity (%) is calculated at each concentration of the compound of the present invention compared to control, and IC value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as positive. When a shifted IC is 1.0 or less, this is defined as negative.

Test Example 9: Fluctuation Ames Test

Mutagenicity of the compound of the present invention is evaluated.

A 20 µL of freezing-stored *Salmonella typhimurium* (TA98 strain, TA100 strain) was inoculated on 10 mL of a liquid nutrient medium (2.5% Oxoid nutrient broth No. 2), and this was incubated at 37° C. for 10 hours under shaking. 7.70 to 8.00 mL of a bacterial solution of the TA98 strain is centrifuged (2000×g, 10 minutes) to remove a culturing solution. Bacteria are suspended in a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, and $MgSO_4 \cdot 7H_2O$: 0.1 g/L) with the same volume as that of the culture medium used for centrifugation. The suspension is added to 120 mL of Exposure medium (Micro F buffer containing biotin: 8 µg/mL, histidine: 0.2 µg/mL, and glucose: 8 mg/mL). 3.10 to 3.42 mL of a bacterial solution of the TA100 strain is mixed with 120 to 130 mL of Exposure medium to prepare a test bacterial suspension. Each 12 µL of DMSO solution of the compound of the present invention (several stage dilution from maximum dose 50 mg/mL at 2 to 3 fold ratio), DMSO as a negative control, and 50 µg/mL of 4-nitroquinoline-1-oxide DMSO solution for the TA98 strain and 0.25 µg/mL of 2-(2-furyl)-3-(5-nitro-2-furyl)acrylamide DMSO solution for the TA100 strain in the assay without metabolic activation, 40 µg/mL of 2-aminoanthracene DMSO solution for the TA98 strain and 20 µg/mL of 2-aminoanthracene DMSO solution for the TA100 strain in the assay with metabolic activation as a positive control, and 588 µL of the test bacterial suspension (a mixture of 498 µL of the test bacterial suspension and 90 µL of 89 mix in the case of metabolic activation assay) are mixed, and this is incubated at 37° C. for 90 minutes under shaking. A 460 µL of the mixture is mixed with 2300 µL of Indicator medium (Micro F buffer containing 8 µg/mL biotin, 0.2 µg/mL histidine, 8 mg/mL glucose, 37.5 µg/mL bromocresol purple), each 50 µL is dispensed to microplate 48 wells/dose, and this is incubated at 37° C. for 3 days. Since the wells containing the bacteria which gained growth ability by point mutation in amino acid (histidine) synthesizing enzyme gene turns from purple to yellow due to a pH change, the number of yellow wells in 48 wells is counted per dose, and is compared with the negative control group. (−) and (+) means negative and positive in mutagenicity respectively.

Test Example 10: hERG Test

For the purpose of assessing risk of an electrocardiogram QT interval prolongation of the compound of the present invention, effects of the compound of the present invention on delayed rectifier $K^+$ current ($I_{Kr}$), which plays an important role in the ventricular repolarization process, is studied using CHO cells expressing human ether-a-go-go related gene (hERG) channel.

After a cell is retained at a membrane potential of −80 mV by whole cell patch clamp method using an automated patch clamp system (QPatch; Sophion Bioscience A/S) and given a leak potential of −50 mV, $I_{Kr}$ induced by depolarization pulse stimulation at +20 mV for 2 seconds and, further, repolarization pulse stimulation at −50 mV for 2 seconds, is recorded. After the generated current is stabilized, extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration in the extracellular solution, is applied to the cell at room temperature for 7 minutes or more. From the recording $I_{Kr}$, an absolute value of the tail peak current is measured based on the current value at the resting membrane potential using analysis software (QPatch assay software; Sophion Bioscience A/S). Further, the % inhibition of tail peak current for the compound of the present invention relative to the tail peak current after application of the solution (0.1% dimethyl sulfoxide solution) is calculated to assess influence of the compound of the present invention on $I_{Kr}$.

Test Example 11: Solubility Test

The solubility of the compound of the present invention is determined under 1% DMSO addition conditions. 10 mmol/L solution of the compound is prepared with DMSO. 2 µL of the solution of the compound of the present invention is respectively added to 198 µL of JP-1 fluid or JP-2 fluid, or 6 µL of the solution of the compound of the present invention is respectively added to 594 µL of JP-1 fluid or JP-2 fluid. The mixture is left standing for 16 hours at 25° C. (condition 1) or shaking at room temperature for 3 hours (condition 2), and the mixture is vacuum-filtered. The filtrate is 10- or 100-fold diluted with methanol/water=1/1 (v/v) or acetonitrile/methanol/water=1/1/2 (v/v/v), and the compound concentration in the filtrate is measured with LC/MS or Solid-Phase Extraction (SPE)/MS by the absolute calibration method. The dilution concentration or dilution solvent is changed as necessary.

The composition of the JP-1 fluid is as below.
Water is added to 2.0 g of sodium chloride and 7.0 mL of hydrochloric acid to reach 1000 mL.
The composition of the JP-2 fluid is as below.
Composition 1. 3.40 g of potassium dihydrogen phosphate and 3.55 g of anhydrous disodium hydrogen phosphate are dissolved in water to reach 1000 mL.
Composition 2. 1 volume of water is added to 1 volume of the solution in which 3.40 g of potassium dihydrogen phosphate and 3.55 g of anhydrous disodium hydrogen phosphate are dissolved in water to reach 1000 mL.

Test Example 12: Powder Solubility Test

Appropriate quantity of the compound of the present invention is put in suitable containers. 200 µL of JP-1 fluid (water is added to 2.0 g of sodium chloride and 7.0 mL of hydrochloric acid to reach 1000 mL), 200 µL of JP-2 fluid (500 mL of water is added to 500 mL of pH 6.8 phosphate buffer solution) or 20 mmol/L sodium taurocholate (TCA)/JP-2 fluid (JP-2 fluid is added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 µL of methanol is added to 100 µL of each filtrate to dilute two-fold. The dilution rate or dilution solvent is changed as necessary. After checking that there is no bubble and precipitate, the container is sealed and shaken. The compound of the present invention is measured using HPLC by the absolute calibration curve method.

Test Example 13: Brain Distribution Test

The compound of the present invention is intravenous administered at a dose of 1 µmol/mL/kg or 0.5 mg/mL/kg to rats. After 30 minutes, the rats are killed by exsanguination through whole blood collection from the abdominal aorta under isoflurane anesthesia.

Then, the brain is excised, and 20 to 25% homogenate is prepared with distilled water.

The obtained blood is centrifuged, and plasma is then obtained. Then, control plasma and control brain are added to the brain sample and the plasma sample, respectively, at 1:1, and each sample is assayed using LC/MS/MS. The measured area ratio (blain/plasma) obtained is used as a brain Kp value.

Test Example 14: P-gp Substrate Test

The compound of the present invention was added to one side of Transwell (registered trademark, CORNING) where human MDR1-expressing cells or parent cells have been monolayer-cultured. The cells were reacted for a constant time. The membrane permeability coefficients from the apical side toward the basolateral side (A→B) and from the basolateral side toward the apical side (B→A) were calculated for the MDR1-expressing cells or the parent cells, and the efflux ratio (ER; ratio of the membrane permeability coefficients of B→A and A→B) values of the MDR1-expressing cells and the parent cells were calculated. The efflux ratio (ER) values of the MDR1-expressing cells and the parent cells were compared to confirm whether or not the compound of the present invention would be a P-gp substrate.

The test results of the compounds of the present invention are shown in the following table.

TABLE 16

| Compound No. | P-gp ER ratio |
| --- | --- |
| I-034 | 1.3 |
| I-046 | 1.9 |
| I-052 | 2.4 |
| I-053 | 1.9 |

Test Example 15: mdr1a (−/−) B6 Mouse P-gp Substrate Test

Animals
mdr1a (−/−) B6 mice (knockout mice) or C57BL/6J mice (wild mice)
Method
1. The mice are allowed to freely take solid food and sterilized tap water.
2. The compound of the present invention is administered to 3 animals at each point in time. Blood and brain samples are collected at a predetermined point in time (e.g., 15 minutes, 30 minutes, 1 hour, 2 hours, 4 hours, 6 hours, 8 hours or 24 hours) after administration. The blood (0.3 to 0.7 mL) is collected with a syringe containing anticoagulants (EDTA and heparin). The blood and brain samples are immediately cooled in ice.
3. The blood sample is centrifugated (1780×g, 10 minutes) for removal of cells to obtain plasma. Then, the plasma sample is transferred to a tube, and stored at −70° C.
4. The brain sample is homogenized at a tissue weight: distilled water weight ratio=1:3, transferred to a tube, and stored at −70° C.
5. The plasma and brain samples are deproteinized, and analyzed by LC/M/MS. A calibration curve prepared from blank plasma or blank brain is used in measurement. A sample for quality control is used to confirm measurement trueness and accuracy.
6. Concentrations (ng/mL and ng/g) in the plasma and the brain are analyzed by an appropriate method for determining pharmacokinetic parameters, for example, WinNonlin (registered trademark) pharmacokinetic analysis software program.
Analysis
Kp; brain/plasma concentration ratio
Kp ratio=knockout mouse (KO) Kp value/wild mouse (Wild) Kp value
KO/Wild ratio of brain AUC/plasma AUC={brain AUC/plasma AUC (KO)}/{brain AUC/plasma AUC (Wild)}

Formulation Example

The following Formulation Examples are only exemplified and not intended to limit the scope of the invention.

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Disintegrated Tablets

The compounds of the present invention and microcrystalline cellulose are mixed, granulated and compressed into tablets to give orally disintegrated tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injections.

Formulation Example 7: Infusions

The compounds of the present invention and phosphate buffer are mixed to give infusions.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster are mixed to give patches.

INDUSTRIAL APPLICABILITY

The compound of the present invention can be a medicament useful as a therapeutic and/or preventive agent for diseases associated with D3 receptor.

The invention claimed is:

1. A compound represented by Formula (I):

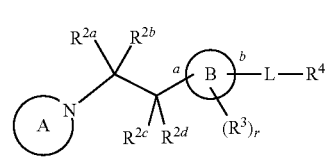

wherein a group represented by:

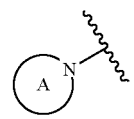

is

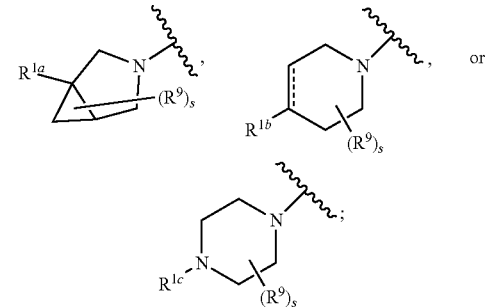

wherein the dashed line represents the presence or absence of a bond;

$R^{1a}$ and $R^{1b}$ are each independently substituted or unsubstituted 5- to 6-membered aromatic heterocyclyl;

$R^{1c}$ is substituted or unsubstituted 5-membered aromatic heterocyclyl;

$R^9$ is each independently halogen, hydroxy, cyano, substituted or unsubstituted alkyl, or substituted or unsubstituted alkyloxy;

two $R^9$ s attached to different ring-constituting atoms may be taken together to form a substituted or unsubstituted (C1-C3) bridge wherein one of carbon atoms constituting the (C1-C3) bridge may be replaced with an oxygen atom or a nitrogen atom;

s is an integer of 0 to 4;

$R^{2a}$ is each independently a hydrogen atom, halogen, hydroxy, cyano, substituted or unsubstituted alkyl, or substituted or unsubstituted alkyloxy;

$R^{2b}$ is each independently a hydrogen atom, halogen, hydroxy, cyano, substituted or unsubstituted alkyl, or substituted or unsubstituted alkyloxy;

$R^{2c}$ and $R^{2d}$ are each independently a hydrogen atom, halogen, hydroxy, cyano, substituted or unsubstituted alkyl, or substituted or unsubstituted alkyloxy;

-L- is —N($R^{10}$)—C(=O)— or —N($R^{10}$)—SO$_2$—;

a bonding hand "a" is bonded to —C$R^{2c}R^{2d}$—;

a bonding hand "b" is bonded to —N($R^{10}$)—;

$R^{10}$ is a hydrogen atom, or substituted or unsubstituted alkyl;

Ring B is a 6-membered non-aromatic carbocycle or a 6-membered non-aromatic heterocycle;

r is an integer of 0 to 4;
$R^3$ is each independently halogen, hydroxy, cyano, substituted or unsubstituted alkyl, or substituted or unsubstituted alkyloxy;
two $R^3$ s attached to different ring-constituting atoms may be taken together to form a bond or a substituted or unsubstituted (C1-C3) bridge wherein one of carbon atoms constituting the (C1-C3) bridge may be replaced with an oxygen atom or a nitrogen atom;
$R^4$ is substituted or unsubstituted aromatic carbocyclyl, substituted or unsubstituted non-aromatic carbocyclyl, substituted or unsubstituted non-aromatic heterocyclyl, substituted or unsubstituted aromatic heterocyclyl, —$CR^{5a}R^{5b}$—$R^6$, or —$CR^{7a}$=$CR^{7b}$—$R^8$;
$R^{5a}$, $R^{5b}$, $R^{7a}$ and $R^{7b}$ are each independently a hydrogen atom, halogen, substituted or unsubstituted C1-C6 alkyl, or substituted or unsubstituted C1-C6 alkyloxy,
$R^6$ is substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy; and
$R^8$ is substituted or unsubstituted non-aromatic carbocyclyl, substituted or unsubstituted aromatic carbocyclyl, substituted or unsubstituted non-aromatic heterocyclyl, or substituted or unsubstituted aromatic heterocyclyl,
or a pharmaceutically acceptable salt thereof.

2. The compound according to claim 1, wherein $R^{1a}$, $R^{1b}$ and $R^{1c}$ are each independently substituted or unsubstituted 5-membered aromatic heterocyclyl, or a pharmaceutically acceptable salt thereof.

3. The compound according to claim 1, wherein $R^{1a}$, $R^{1b}$ and $R^{1c}$ are each independently substituted or unsubstituted isoxazolyl, or a pharmaceutically acceptable salt thereof.

4. The compound according to claim 1,
wherein $R^{1a}$, $R^{1b}$ and $R^{1c}$ are each independently a group represented by:

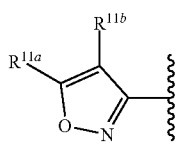

wherein $R^{11a}$ and $R^{11b}$ are each independently a hydrogen atom, halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenyl sulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, provided that $R^{11a}$ and $R^{11b}$ are not simultaneously hydrogen atoms,
or a pharmaceutically acceptable salt thereof.

5. The compound according to claim 1, wherein a group represented by:

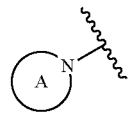

is:

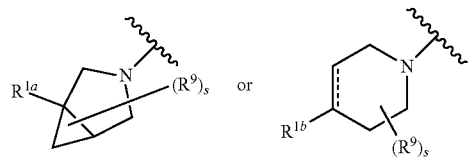

wherein $R^9$ and s are the same as defined in claim 1;
$R^{1a}$ is:

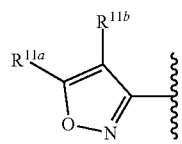

wherein $R^{11a}$ is substituted or unsubstituted alkyl, substituted or unsubstituted non-aromatic carbocyclyl, or substituted or unsubstituted alkylcarbonyl; and $R^{11b}$ is a hydrogen atom; and
$R^{1b}$ is:

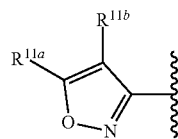

wherein $R^{11a}$ a is a hydrogen atom; and $R^{11b}$ is substituted or unsubstituted aromatic carbocyclyl, substituted or unsubstituted non-aromatic carbocyclyl, or substituted or unsubstituted alkyl,
or a pharmaceutically acceptable salt thereof.

6. The compound according to claim 4, wherein
$R^{11a}$ is C1-C6 alkyl optionally substituted with one or more group(s) selected from the group consisting of monocyclic non-aromatic carbocyclyl substituted with halogen, monocyclic non-aromatic carbocyclyl and halogen, or $R^{11a}$ is monocyclic non-aromatic carbocyclyl optionally substituted with one or more group(s) selected from the group consisting of halogen, C1-C6 alkyl and C1-C6 haloalkyl, and $R^{11b}$ is a hydrogen atom,
or a pharmaceutically acceptable salt thereof.

7. The compound according to claim 1, wherein a group represented by:

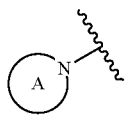

is:

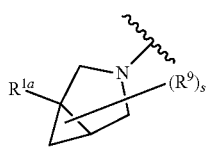

wherein $R^{1a}$, $R^9$ and s are the same as defined in claim 1, or a pharmaceutically acceptable salt thereof.

8. The compound according to claim 1, wherein a group represented by:

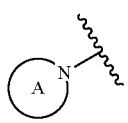

is:

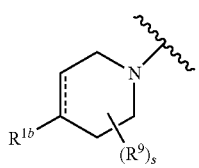

wherein the dashed line, $R^{1b}$, $R^9$ and s are the same as defined in claim 1, or a pharmaceutically acceptable salt thereof.

9. The compound according to claim 1, wherein $R^4$ is substituted or unsubstituted phenyl, substituted or unsubstituted indazolyl, substituted or unsubstituted pyrazolopyridyl, substituted or unsubstituted benzotriazolyl, substituted or unsubstituted pyridyl, substituted or unsubstituted isoindolinyl, substituted or unsubstituted dihydroisoquinolinyl, substituted or unsubstituted dihydropyridyl, —$CR^{5a}R^{5b}$—$R^6$, or —$CR^{7a}$=$CR^{7b}$—$R^8$;

$R^6$ is substituted or unsubstituted oxazolyl, substituted or unsubstituted isoxazolyl, substituted or unsubstituted oxadiazolyl, substituted or unsubstituted pyrazolyl, substituted or unsubstituted triazolyl, substituted or unsubstituted thiazolyl, substituted or unsubstituted thiadiazolyl, substituted or unsubstituted pyrimidinyl, substituted or unsubstituted pyrimidinyloxy, substituted or unsubstituted pyrazinyloxy, or substituted or unsubstituted isoxazolyloxy; and $R^8$ is substituted or unsubstituted pyrimidinyl, or substituted or unsubstituted pyrazolyl, or a pharmaceutically acceptable salt thereof.

10. The compound according to claim 1, wherein
$R^{2a}$, $R^{2b}$, $R^{2c}$, $R^{2d}$, $R^{5a}$, $R^{5b}$, $R^{7a}$, and $R^{7b}$ are hydrogen atoms;
s is 0;
r is 0 or 1; and
-L- is —NH—C(=O)—,
or a pharmaceutically acceptable salt thereof.

11. The compound according to claim 1, wherein the compound is selected from the group consisting of

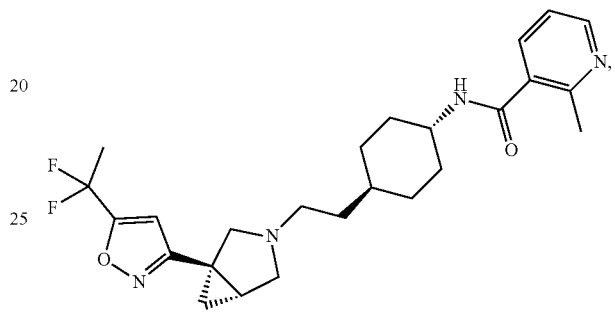

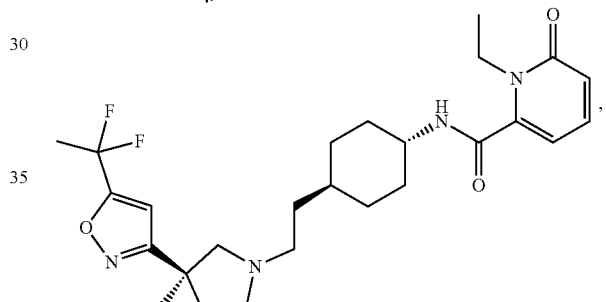

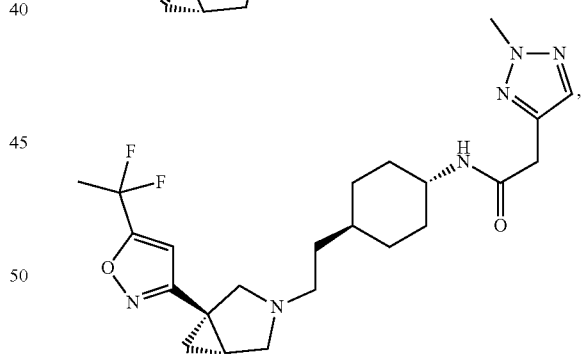

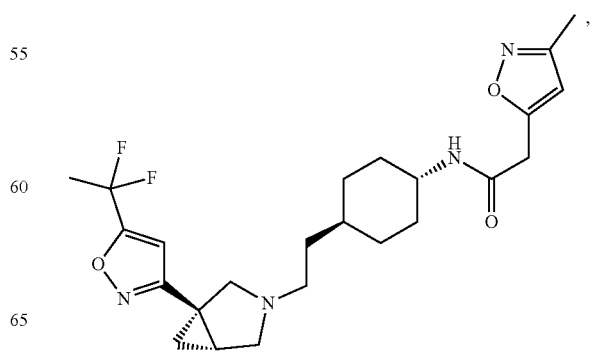

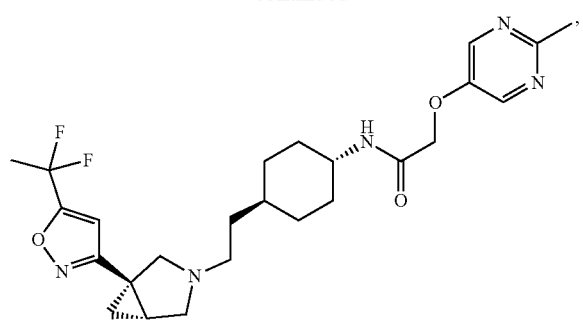
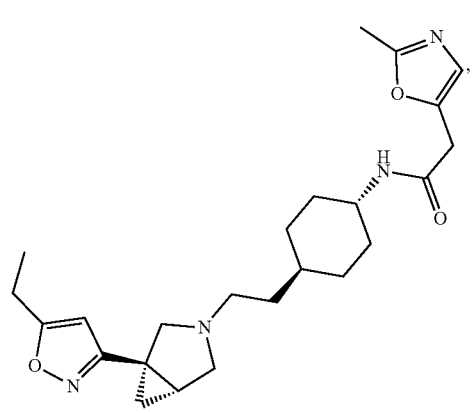
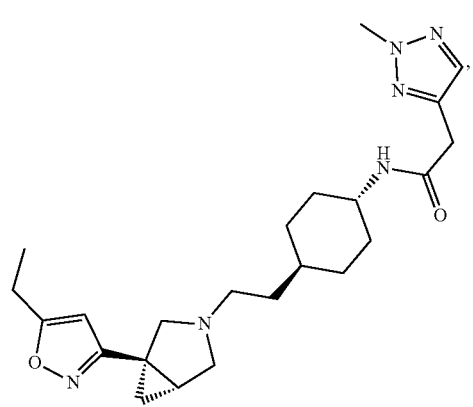
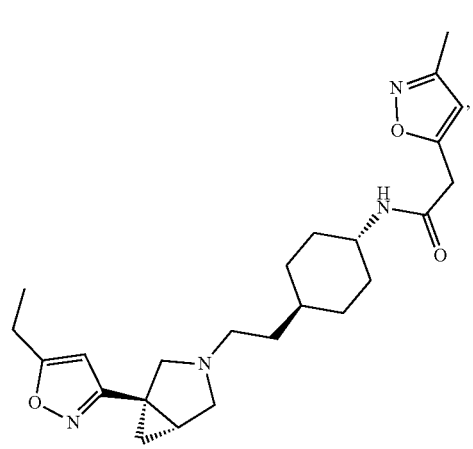
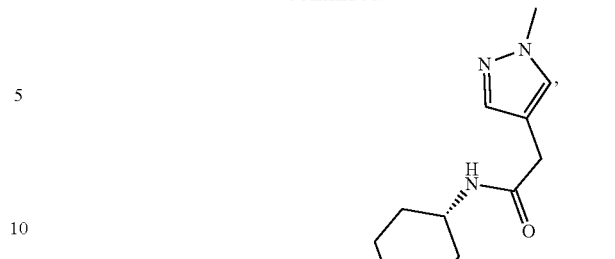
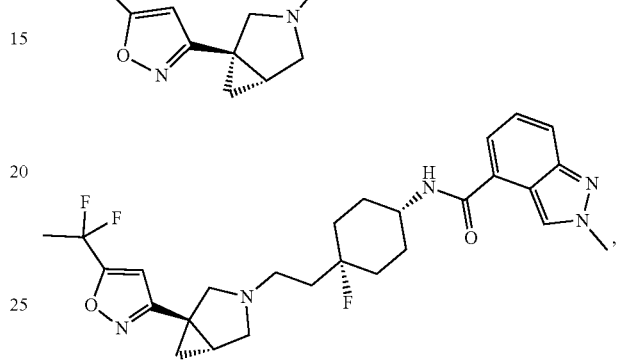
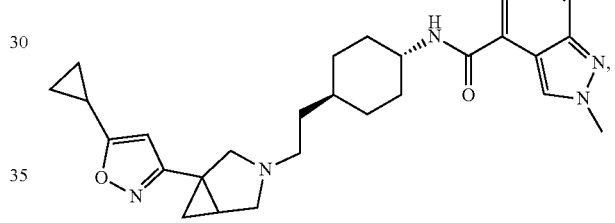
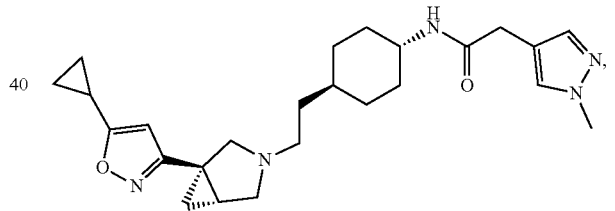
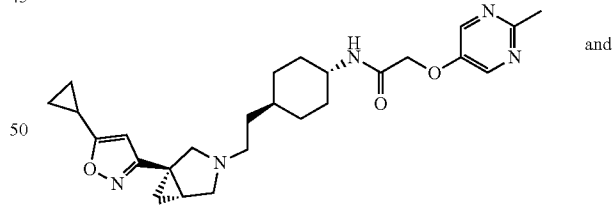
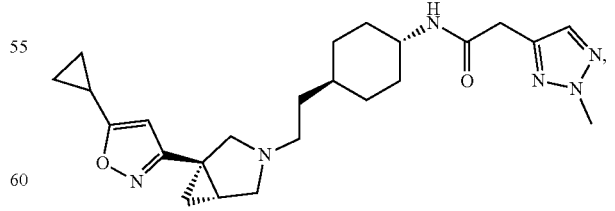
or a pharmaceutically acceptable salt thereof.
12. A pharmaceutical composition comprising the compound according to claim 1, or a pharmaceutically acceptable salt thereof, and a pharmaceutical additive.

13. A dopamine D3 receptor antagonist comprising the compound according to claim 1, or a pharmaceutically acceptable salt thereof, and a pharmaceutical additive.

14. A method for treating and/or preventing a disease associated with a dopamine D3 receptor, comprising administering an effective amount of the compound according to claim 1 or a pharmaceutically acceptable salt thereof to a patient in need thereof.

15. The compound according to claim 1, wherein a group represented by:

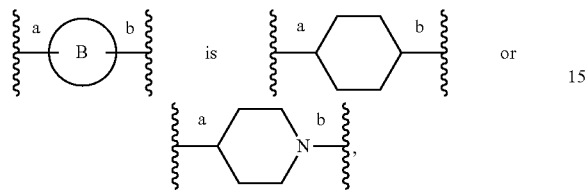

or a pharmaceutically acceptable salt thereof.

* * * * *